(12) United States Patent
Leland

(10) Patent No.: US 10,221,388 B2
(45) Date of Patent: *Mar. 5, 2019

(54) METHOD AND DEVICE FOR PLANKTON SEPARATION

(71) Applicant: Nancy Leland, North Andover, MA (US)

(72) Inventor: Nancy Leland, North Andover, MA (US)

(*) Notice: Subject to any disclaimer, the term of this patent is extended or adjusted under 35 U.S.C. 154(b) by 241 days.

This patent is subject to a terminal disclaimer.

(21) Appl. No.: 15/152,359

(22) Filed: May 11, 2016

(65) Prior Publication Data

US 2016/0312173 A1    Oct. 27, 2016

Related U.S. Application Data

(63) Continuation-in-part of application No. 14/615,110, filed on Feb. 5, 2015, now Pat. No. 9,540,632.

(60) Provisional application No. 61/936,698, filed on Feb. 6, 2014, provisional application No. 62/174,027, filed on Jun. 11, 2015, provisional application No. 62/249,633, filed on Nov. 2, 2015.

(51) Int. Cl.
| | |
|---|---|
| *C12N 1/02* | (2006.01) |
| *C12N 13/00* | (2006.01) |
| *C12N 1/12* | (2006.01) |
| *C12N 1/10* | (2006.01) |
| *C12N 1/20* | (2006.01) |
| *C12M 1/00* | (2006.01) |

(52) U.S. Cl.
CPC ............... *C12M 47/02* (2013.01); *C12N 1/02* (2013.01); *C12N 1/10* (2013.01); *C12N 1/12* (2013.01); *C12N 1/20* (2013.01); *C12N 13/00* (2013.01)

(58) Field of Classification Search
CPC . A01G 33/00; C12N 1/02; C12N 1/12; C12N 1/10; C12N 1/20; C12M 47/02; C02F 3/322; A01K 61/20; A01K 61/90
USPC .............. 47/1.4; 210/767, 167.22; 73/170.29
See application file for complete search history.

(56) References Cited

U.S. PATENT DOCUMENTS

| | | |
|---|---|---|
| 3,838,793 A | 10/1974 | Rochette |
| 5,713,303 A | 2/1998 | Willinsky et al. |
| (Continued) | | |

FOREIGN PATENT DOCUMENTS

| | | |
|---|---|---|
| CN | 201803883 U | 4/2011 |
| CN | 102422828 A | 4/2012 |
| JP | 2001161207 A | 6/2001 |

OTHER PUBLICATIONS

Buchanan, C., et al., "A laboratory method for studying zooplankton swimming behaviors," *Hydrobiologia*, 94: 77-89 (1982).

(Continued)

*Primary Examiner* — Claire A Norris
(74) *Attorney, Agent, or Firm* — Hamilton, Brook, Smith & Reynolds, P.C.

(57) ABSTRACT

Methods, devices and kits for the physical separation of plankton into its component parts utilizing phototactic behavior are described. The methods utilize positive phototactic behavior and negative contrast orientation of the zooplankton for maximal in situ separation of phytoplankton and zooplankton for use in further studies and evaluation of separation efficiency. The devices provide effective conditions for use in the separation of plankton into component parts.

9 Claims, 36 Drawing Sheets

(56) References Cited

U.S. PATENT DOCUMENTS

| | | | |
|---|---|---|---|
| 6,123,858 | A | 9/2000 | Manz |
| 7,000,567 | B1 | 2/2006 | Hsiao |
| 7,201,114 | B2 | 4/2007 | Hsiao |
| 7,820,025 | B2 | 10/2010 | Ciampi et al. |
| 8,580,560 | B1 | 11/2013 | Ellis et al. |
| 9,540,632 | B2 | 1/2017 | Leland |
| 2003/0143752 | A1* | 7/2003 | Feldsine ............... G01N 21/76 436/164 |
| 2012/0125836 | A1 | 5/2012 | Hintz et al. |
| 2013/0233779 | A1 | 9/2013 | Farrish |
| 2017/0067043 | A1 | 3/2017 | Leland |

OTHER PUBLICATIONS

Forward, R., Jr., "Diel Vertical Migration: Zooplankton Photobiology and Behaviour," *Oceanography Marine Biology Annual Review*, 26: 361-393 (1988).

Graham, J., et al., "Guidelines for Design and Sampling for Cyanobacterial Toxin and Taste-and-Odor Studies in Lakes and Reservoirs," *Scientific Investigations Report 2008-5038 of the U.S. Department of the Interior and U.S. Geological Survey.*

Ringelberg, J., "An account of a preliminary mechanistic model of swimming behaviour in *Daphnia*: its use in understanding diel vertical migration," *Hydrobiologia*, 307: 161-165 (1995).

Ringelberg, J., et al., "Contrast Orientation in Daphnia Magna and its Significance for Vertical Plane Orientation in the Pelagic Biotope in General," *Netherlands Journal of Zoology*, 25(4): 454-475 (1975).

Ringelberg, J., "Changes in Light Intensity and Diel Vertical Migration: A Comparison of Marine and Freshwater Environments," *Journal of Marine Biology Association U.K.*, 75: 15-25 (1995).

Ringelberg, J., "The Positively Phototactic Reaction of Daphnia Magna Straus: A Contribution to the Understanding of Diurnal Vertical Migration," *Netherlands Journal of Sea Research*, 2(3): 319-406 (1964).

Schallek, W., "The Vertical Migration of the Copepod Acartia tonsa Under Controlled Illumination," *Biological Laboratories, Harvard University and the Woods Hole Oceanographic Institution*, pp. 112-126 (1942).

"Scientific Assessment of Freshwater Harmful Algal Blooms," *Interagency Working Group on Harmful Algal Blooms, Hypoxia, and Human Health* (2008).

United States Environmental Protection Agency (2012) "Cyanobacteria and Cyanotoxins: Information for Drinking Water Systems," (EPA-810F11001).

Capron, S. "Occurrence of Microcystins Produced by Microcystis Aeruginosa (Blue-Green Algae) and Accumulation in Zooplankton," Thesis, University of New Hampshire (1995).

Johnson, K., "Microcystins in New Hampshire Lakes and Bioaccumulation in Zooplankton," Thesis, University of New Hampshire (1999).

Hathaway, Richard., II., "Bioaccumulation of Microcystin in Crayfish and Mussels Within New Hampshire Lakes and Their Potential as Biomonitors," Thesis, B.A. State of University of New York at Plattsburgh (2001).

Cai, Haiyuan et al., "Bacterial Community Composition of Size-Fractioned Aggregates within the Phycosphere of Cyanobacterial Blooms in a Eutrophic Freshwater Lake," *PLOS ONE*, 9(8): 1-11 (Aug. 2014).

Cyanobacteria (Blue-green Algae) Guidance for Vermont Communities, Vermont Department of Health, 40 pp. (Aug. 2015).

Kromkamp, Jacco C. and Luuc R. Mur, "Buoyant density changes in the cyanobactcrium *Microcystis aeruginosa* due to changes in the cellular carbohydrate content," *FEMS Microbiology Letters*, 25: 105-109 (1984).

Kromkamp, Jacco C. and Anthony E. Walsby, "A computer model of buoyancy and vertical migration in cyanobacteria," *Journal of Plankton Research*, 12(1): 161-183 (1990).

Nakamura, Takahiko et al., "Flotation and Sedimentation of a Single *Microcystis* Floc Collected from Surface Bloom," *Wat. Res.*, 27(6): 979-983 (1993).

Oliver, Roderick Lewis, "Floating and Sinking in Gas-vacuolate Cyanobacteria," *Journal of Phycology*, 30: 161-173 (1994).

Reynolds, Colin S. et al. "Cyanobacterial dominance: the role of buoyancy regulation in dynamic lake environments," *New Zealand Journal of Marine and Freshwater Research*, 21: 379-390 (1987).

Rowe, M.D. et al., "Vertical distribution of buoyant *Microcystis* blooms in a Lagrangian particle tracking model for short-term forecasts in Lake Erie," *Journal of Geophysical Research: Oceans*, Research Article, 10.1002/2016JC011720: pp. 1-19 (2016).

Thomas, R.H. and A.E. Walsby, "Buoyancy Regulation in a Strain of *Microcystis,*" *Journal of General Microbiology*, 131: 799-809 (1985).

Van Rijn, Jaap and Moshe Shilo, "Carbohydrate fluctuations, gas vacuolation, and vertical migration of scum-forming cyanobacteria in fishponds," *Limnol. Oceanogr.*, 30(6): 1219-1228 (1985).

Office Action, U.S. Appl. No. 15/345,823, filed Nov. 8, 2016, entitled "Method and Device for Plankton Separation", dated Jun. 11, 2018.

* cited by examiner

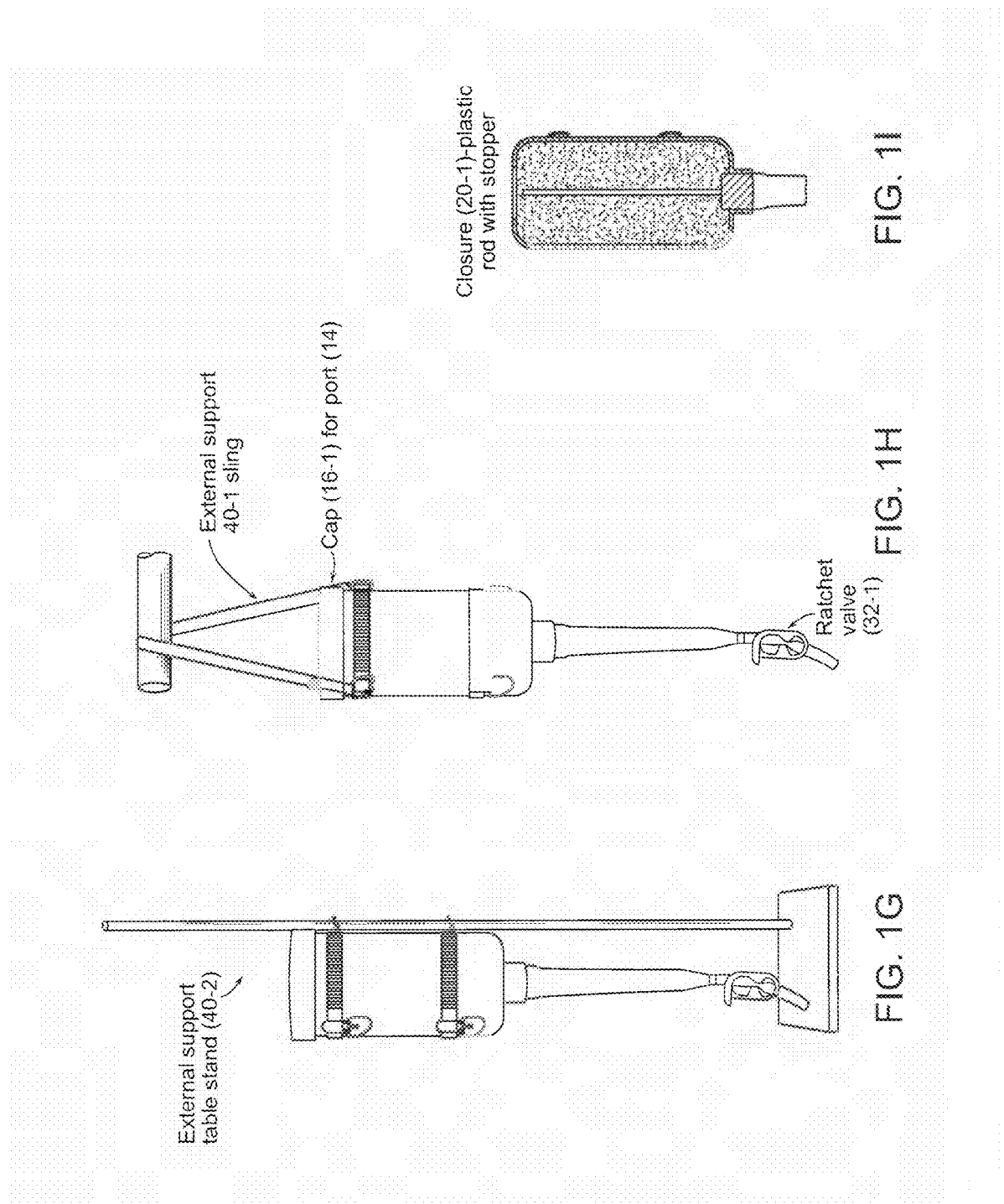

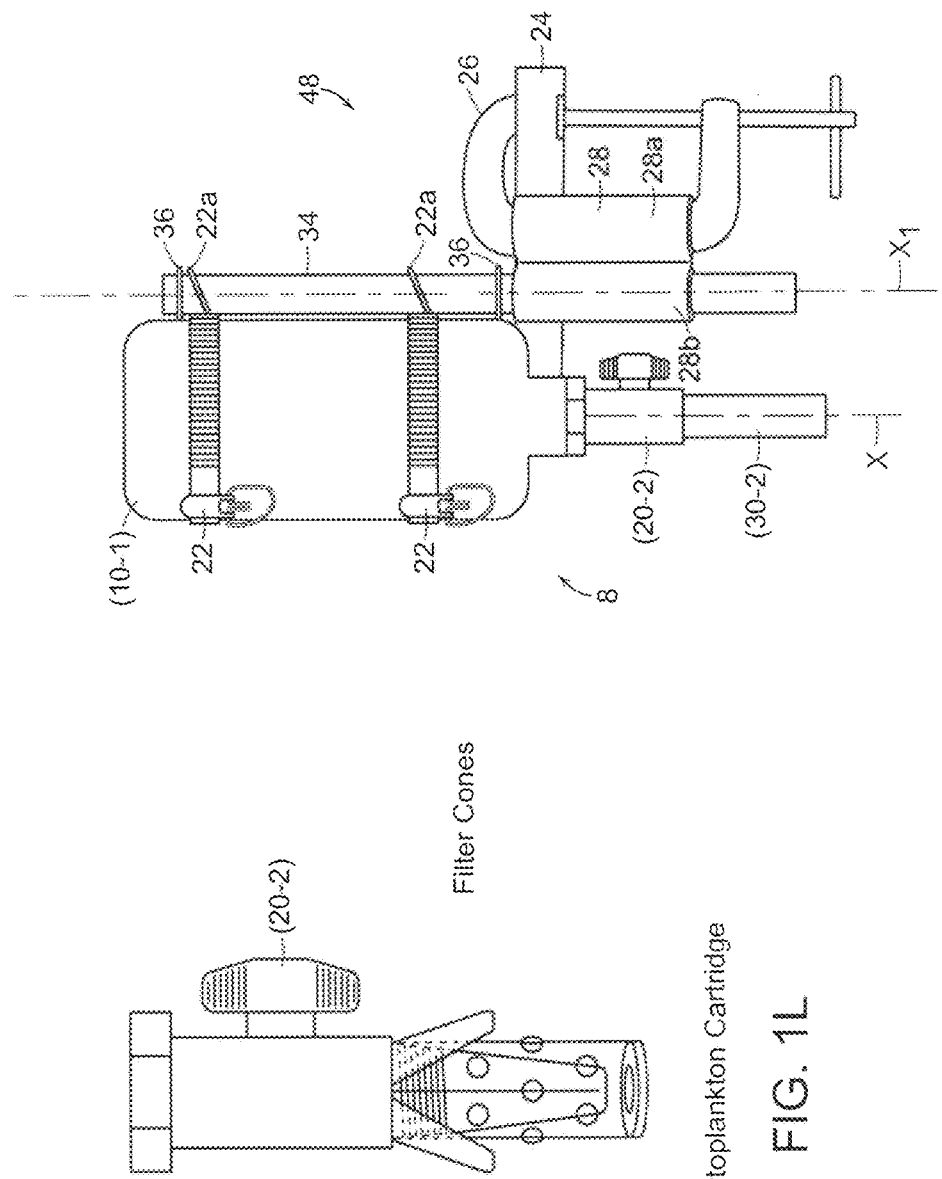

Separation efficiency curves for macrozooplankton biomass (solid lines) versus microcystic equivalents (dashes) (A) and chlorophyll(a) (B) (dots) in Lake Cochichcwick 4 Sep 2013 and 10 Oct 2013

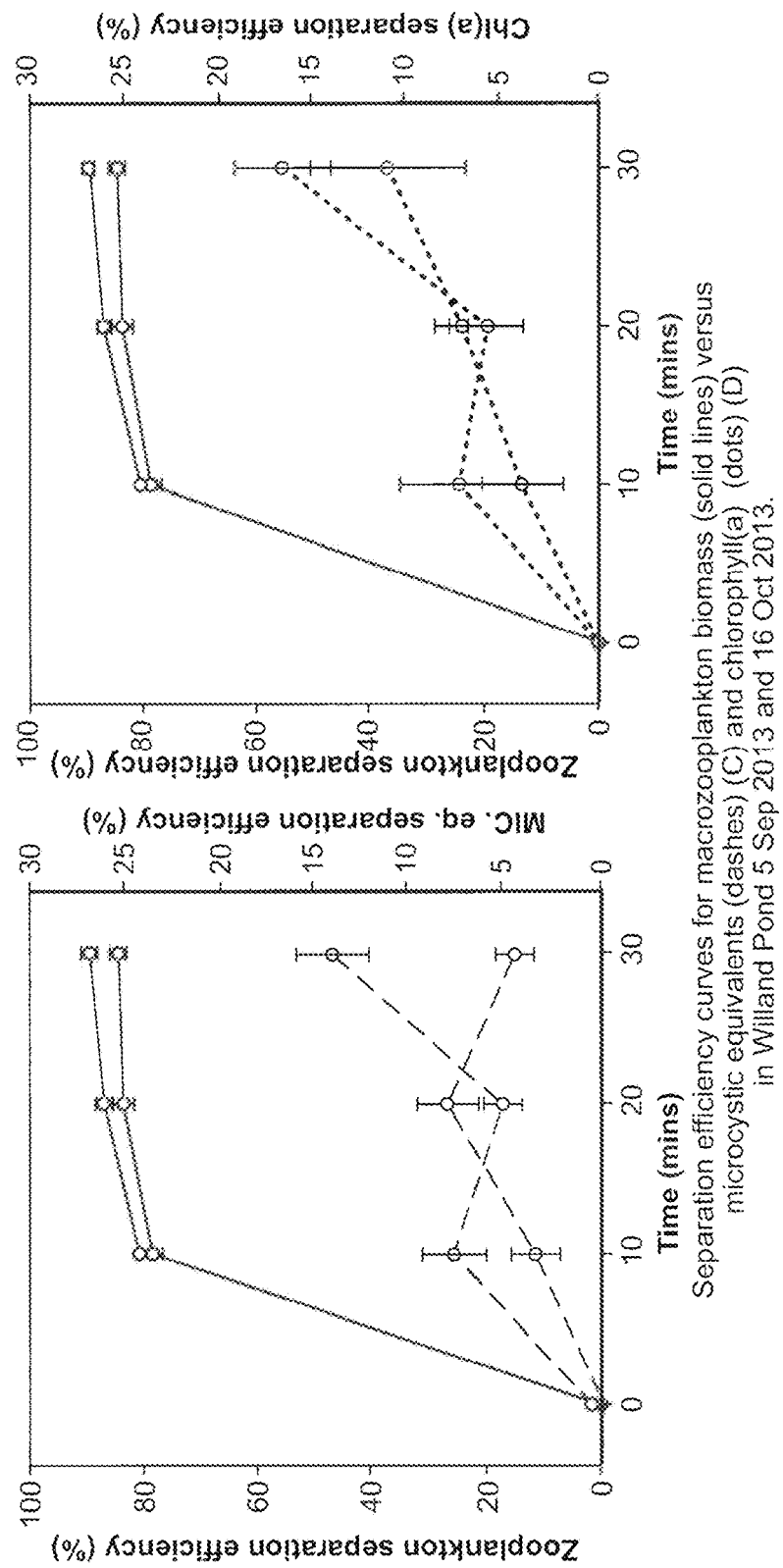

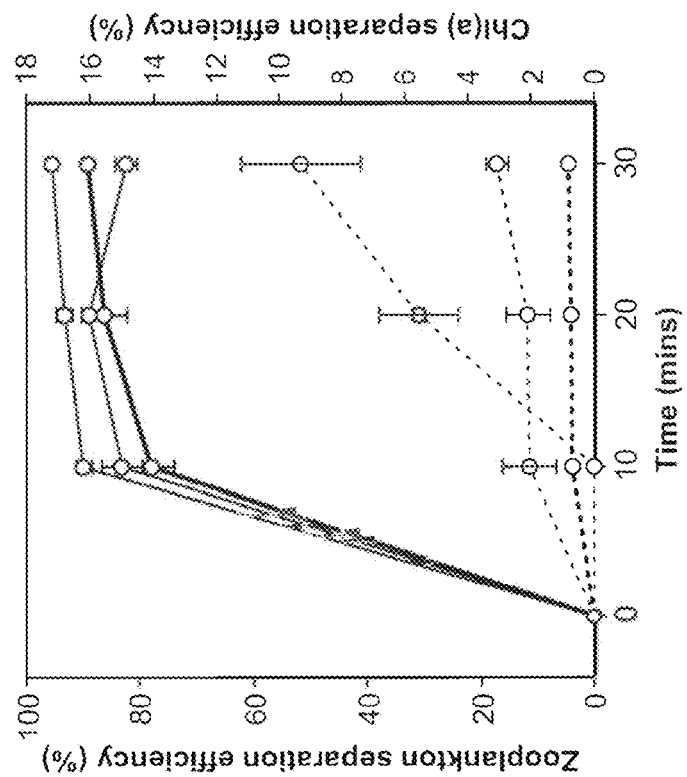
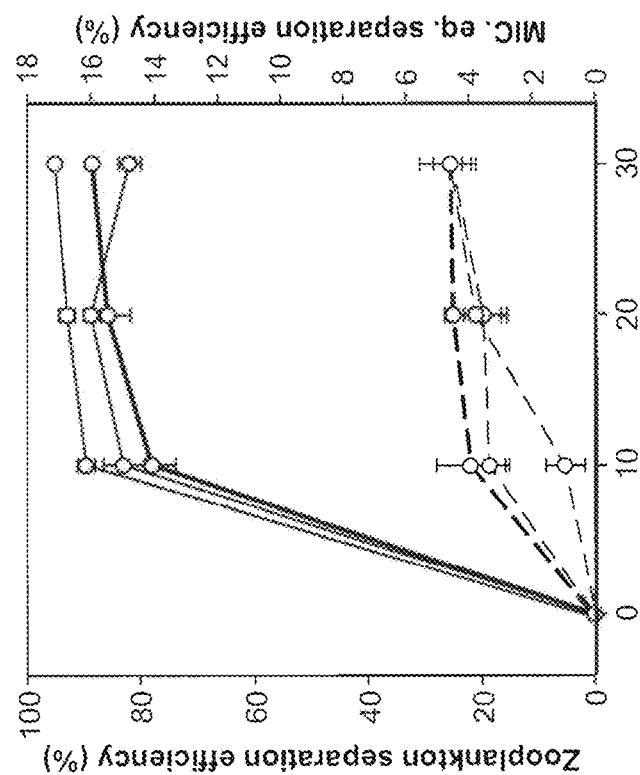
FIG. 8A / FIG. 8B
Separation efficiency curves for macrozooplankton biomass (solid lines) versus microcystic equivalents (dashes) (A) and chlorophyll(a) (B) (dots) in Lake Cochichewick 4 Sep 2013, 10 Oct 2013 (———) and 29 Oct 2014 (— - —).

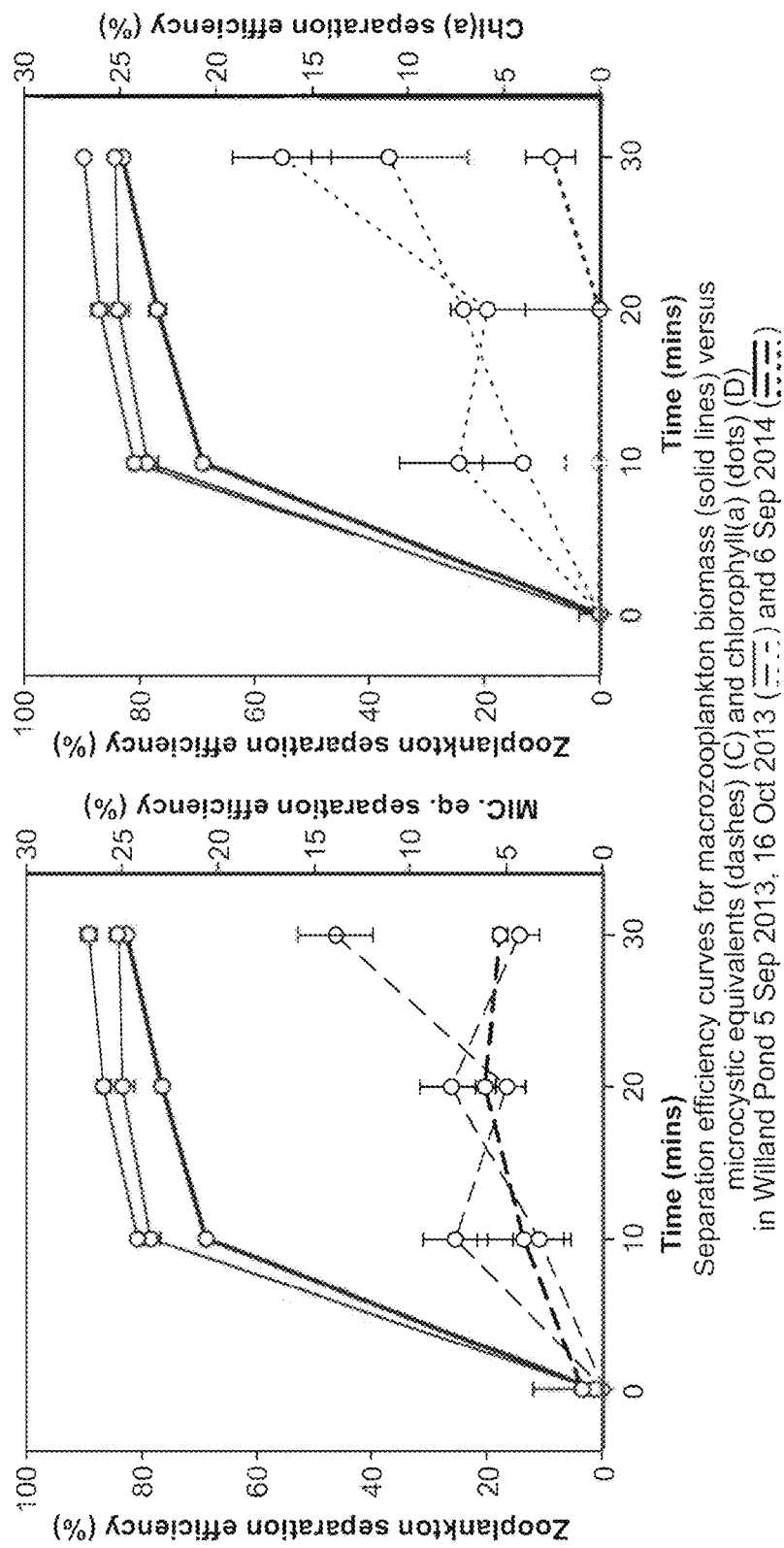

Effect of minimum diameter on separation efficiency of macrozooplankton in Lake Cochichewick 29 October 2014 with standard errors for each shown. Ambient (t–3.54, df–4, p–.024), Artificial (t–4.90, df–4, p–.008)

Separation efficiencies for individual zooplankters from Lake Cochichewick (29 October 2014) and Willard Pond (6 September 2014).

FIG. 11

Table 1. Separation efficiencies for zooplankton biomass as observed in Lake Cochichewick 2013-2014. Mean values with standard error of the mean.

| | *Daphnia mendotae* | | | | *Daphnia ambigua* | | | | *Diaphanosoma brachyurum* | | | | | |
|---|---|---|---|---|---|---|---|---|---|---|---|---|---|---|
| | 29-Oct-14 | | 29-Oct-14 | | | | | | 4-Sep-13 | | 10-Oct-13 | | 29-Oct-14 | |
| | Mean | SEM | Mean | SEM | | | | | Mean | SEM | Mean | SEM | Mean | SEM |
| T=10 | 70.1 | 2.8 | 50.3 | 9.0 | | | | | 81.4 | 2.3 | 66.6 | 7.1 | 40.6 | 9.8 |
| T=20 | 72.2 | 10.7 | 59.4 | 7.8 | | | | | 84.7 | 3.6 | 74.7 | 8.4 | 77 | 11.6 |
| T=30 | 78.2 | 2.4 | 61.6 | 2.4 | | | | | 86.8 | 4.7 | 78.7 | 6.0 | 89.4 | 5.5 |

| | *Microcyclops rubellus* | | | | | | | | *Diaptomus spp.* | | | | | |
|---|---|---|---|---|---|---|---|---|---|---|---|---|---|---|
| | 4-Sep-13 | | 10-Oct-13 | | 29-Oct-14 | | | | 4-Sep-13 | | 10-Oct-13 | | 29-Oct-14 | |
| | Mean | SEM | Mean | SEM | Mean | SEM | | | Mean | SEM | Mean | SEM | Mean | SEM |
| T=10 | 94.6 | 2.8 | 83.3 | 5.1 | 74.1 | 2.2 | | | 89.7 | 1.3 | 83.4 | 5.1 | 83.5 | 5.7 |
| T=20 | 100 | 0.0 | 82.5 | 3.5 | 85.6 | 6.6 | | | 93.4 | 1.1 | 91.3 | 0.8 | 94.7 | 1.1 |
| T=30 | 100 | 0.0 | 87.3 | 4.5 | 88.4 | 3.1 | | | 95.1 | 0.3 | 80.9 | 3.1 | 95.7 | 1.4 |

| | Copepodites | | | | | | | | Nauplii | | | | | |
|---|---|---|---|---|---|---|---|---|---|---|---|---|---|---|
| | 4-Sep-13 | | 10-Oct-13 | | 29-Oct-14 | | | | 4-Sep-13 | | 10-Oct-13 | | 29-Oct-14 | |
| | Mean | SEM | Mean | SEM | Mean | SEM | | | Mean | SEM | Mean | SEM | Mean | SEM |
| T=10 | 83.7 | 1.4 | 56.9 | 5.1 | 47.6 | 6.2 | | | 44.9 | 8.4 | 11.3 | 5.8 | 6.26 | 0.8 |
| T=20 | 82 | 3.9 | 50.1 | 1.5 | 69.3 | 2.7 | | | 47.2 | 5.4 | 29.8 | 9.1 | 9.79 | 0.9 |
| T=30 | 90.2 | 1.5 | 45.2 | 10.1 | 64.9 | 3.6 | | | 54.2 | 3.1 | 20.7 | 8.3 | 9.35 | 1.1 |

FIG. 12

Table 2. Separation efficiencies for zooplankton biomass as observed in Willand Pond 2013-2014. Mean values with standard error of the mean.

*Daphnia catawba*

|  | 5-Sep-13 | | 16-Oct-13 | | 6-Sep-14 | |
|---|---|---|---|---|---|---|
|  | Mean | SEM | Mean | SEM | Mean | SEM |
| T=10 | 90.1 | 1.3 | 80.7 | 1.5 | 69.9 | 7.0 |
| T=20 | 92.1 | 1.8 | 88.9 | 0.5 | 76.2 | 9.6 |
| T=30 | 94.6 | 1.0 | 90.7 | 2.6 | 83.6 | 6.3 |

*Daphnia ambigua*

|  | 5-Sep-13 | | 16-Oct-13 | | 6-Sep-14 | |
|---|---|---|---|---|---|---|
|  | Mean | SEM | Mean | SEM | Mean | SEM |
| T=10 | 80.9 | 5.8 | 63.8 | 9.0 | 50 | 5.2 |
| T=20 | 89.8 | 2.1 | 77.2 | 11.6 | 59 | 6.1 |
| T=30 | 87.9 | 1.1 | 92.3 | 7.7 | 67 | 2.6 |

*Mesocyclops edax*

|  | 5-Sep-13 | | 16-Oct-13 | | 6-Sep-14 | |
|---|---|---|---|---|---|---|
|  | Mean | SEM | Mean | SEM | Mean | SEM |
| T=10 | 67.3 | 1.7 | 63.9 | 3.5 | 60.5 | 1.9 |
| T=20 | 74.2 | 4.7 | 77.3 | 1.3 | 84 | 4.1 |
| T=30 | 82.5 | 3.1 | 87.9 | 2.4 | 88.1 | 3.5 |

*Diaptomus spp.*

|  | 5-Sep-13 | | 16-Oct-13 | | 6-Sep-14 | |
|---|---|---|---|---|---|---|
|  | Mean | SEM | Mean | SEM | Mean | SEM |
| T=10 | 75.3 | 2.2 | 82 | 2.3 | 61.8 | 8.3 |
| T=20 | 88.5 | 6.7 | 81.2 | 4.2 | 76.6 | 5.4 |
| T=30 | 81.9 | 8.5 | 76.3 | 1.8 | 88.6 | 3.6 |

Copepodites

|  | 5-Sep-13 | | 16-Oct-13 | | 6-Sep-14 | |
|---|---|---|---|---|---|---|
|  | Mean | SEM | Mean | SEM | Mean | SEM |
| T=10 | 40.8 | 4.4 | 38.3 | 2.1 | 28.9 | 3.4 |
| T=20 | 39 | 3.4 | 40.7 | 1.5 | 44 | 4.7 |
| T=30 | 44.7 | 8.7 | 47.5 | 4.7 | 42.4 | 1.4 |

Nauplii

|  | 5-Sep-13 | | 16-Oct-13 | | 6-Sep-14 | |
|---|---|---|---|---|---|---|
|  | Mean | SEM | Mean | SEM | Mean | SEM |
| T=10 | 16.6 | 0.8 | 12.7 | 3.2 | 13.1 | 1.3 |
| T=20 | 18.3 | 1.1 | 10.6 | 0.6 | 13.3 | 2.4 |
| T=30 | 22.7 | 1.7 | 10.2 | 2.7 | 16.9 | 2.2 |

Lake Attitach Sep 29, 2015 Vertical Profiles (3 ml horizons)
T=30 minutes

IT = Integrated Tube Sample    160X = Net Plankton Sample

METHOD AND DEVICE FOR PLANKTON SEPARATION

RELATED APPLICATIONS

This application is a continuation-in-part of U.S. application Ser. No. 14/615,110, filed on Feb. 5, 2015, which claims the benefit of U.S. Provisional Application No. 61/936,698, filed on Feb. 6, 2014. This application also claims the benefit of U.S. Provisional Application No. 62/174,027, filed on Jun. 11, 2015 and U.S. Provisional Application No. 62/249,633, filed on Nov. 2, 2015. The entire teachings of the above-identified applications are incorporated herein by reference.

BACKGROUND OF THE INVENTION

Under certain conditions, algae, bacteria and other organisms create health hazards for humans and animals through the production of toxins or bioactive compounds and/or cause deterioration of water quality from production of high biomass. For example, the presence of toxins in recreational and drinking water can produce many deleterious effects in humans, including but not limited to fever, headache, muscle and joint pain, blisters, stomach cramps, diarrhea, vomiting, mouth ulcers and allergic reactions. In severe cases, seizures, liver failure and respiratory arrest may occur. Therefore, increased occurrence of these organisms and resultant problems is of great concern.

Improving monitoring techniques for surveillance programs and ecological risk assessments would aid in determining how best to manage these aquatic ecosystems, thus, helping to ensure that the waterways are properly managed to maintain their aesthetic, economic, ecological and recreational value.

SUMMARY OF THE INVENTION

The methods and devices of the invention allow the researcher to collect and separate plankton samples for surveillance programs and ecological risk assessments. Fast, easy and cost effective methods and devices are described herein that overcome existing limitations associated with the collection, separation and analysis of samples from waterways. Such limitations can include, for example, spatial and temporal variability, toxigenicity, and varying sample quality.

Methods, devices (e.g., apparatuses) and kits for separating a plankton sample into its component parts utilizing phototactic behavior are described. Specifically, the methods and devices of the claimed invention provide the conditions necessary to initiate, direct and reinforce the movement (e.g., migration) of zooplankton away from phytoplankton in a sample, for use in research requiring separation of plankton samples, for example, to provide measures of phytoplankton and zooplankton biomass. The separated plankton samples can yield measures of biomass in different trophic levels. These samples and measurements can be used for various analyses, including bioaccumulation measurement or evaluation of biological community associations.

In one aspect of the invention, a plankton separating device is described, comprising: a darkened chamber and a collection cartridge (e.g., tube) attached to the chamber for allowing entry of highly directional ambient light, wherein the collection tube is of sufficient length to reinforce migration of the zooplankton, thereby separating the plankton into its component parts.

In one aspect of the invention, a plankton separating device is described, comprising: a darkened chamber having at least one port, wherein the port has a closure; and a collection tube attached to the port of the chamber for allowing entry of highly directional ambient light, wherein the collection tube is of sufficient length to reinforce migration of the zooplankton, thereby separating the plankton into its component parts.

In some embodiments, the closure is a stopper or valve. In particular embodiments, the darkened chamber can be configured to be positioned above the transparent collection tube for operation. The darkened chamber can have an outer perimeter surrounding a central axis. The collection tube can be elongate and extend from the darkened chamber along the central axis, starting beyond a point that makes about a 48° angle to the central axis while extending to the nearest location of maximum outer perimeter dimension of the darkened chamber. This can form a contrast shadow relative to the transparent collection tube, simulating a predator to the zooplankton, minimizing the likelihood that zooplankton that have migrated into the collection tube will migrate back into the darkened chamber. In this way, the zooplankton migration into the tube can be reinforced. Therefore, the collection tube should be of sufficient length to reinforce this negative contrast orientation, and, thus, migration of the zooplankton.

In some embodiments, the collection tube can be transparent and can have one of tapered or straight side walls. The outer perimeter of the darkened chamber and the side walls of the transparent collection tube can be generally round. The transparent collection tube can extend away from the darkened chamber beyond a point that makes about a 20°±2° angle to the central axis while extending to the nearest location of maximum outer perimeter dimension of the darkened chamber. The about 20° angle can continue to form a contrast shadow relative to the transparent collection tube that simulates a predator to plankton. At least about 40% of the length of the transparent collection tube can extend beyond the point that makes the about a 20° angle. The darkened chamber and the transparent collection tube can have outer diameters with a darkened chamber $OD_b$ to transparent collection tube $OD_t$ ratio of about 3-3.5 to 1. The transparent collection tube can have a length with a transparent collection tube length to $OD_t$ ratio of about 3.9-5.2 to 1. These ratios can provide a contrast shadow relative to the transparent collection tube, simulating a predator to zooplankton, and sufficient length in the transparent collection tube for zooplankton to migrate and move away from the darkened chamber to minimize zooplankton collected in the transparent collection tube from migrating back into the darkened chamber.

The device and methods can utilize ambient light and are able to be used in situ. In other words, the devices and methods do not require the use of a light source other than ambient light (e.g., bulb, LED or other illumination). Thus, in some embodiments, the light is ambient. In some embodiments, the device does not include an artificial light source or filter. In some embodiments the device comprises a reflective surface, such as a mirror or foil. In some embodiments, the level of introduced light must be of a sufficient level to initiate positive phototactic movement of the zooplankton to the fluid-filled collection tube. In one aspect, the change in light intensity is sudden. In some embodiments, the stimulus beam of light can be approximately 2 cm, e.g., 21.5 nm or 20 mm.

In some embodiments, the collection tube comprises (e.g., is filled with) a fluid, preferably water, such as filtered water, e.g., in situ filtered water. In some embodiments, the diluent is in situ filtered water to maintain thermal and chemical equilibrium of the environment for the zooplankton.

In some embodiments, the collection tube is transparent, i.e., entirely transparent. In another embodiment, most (for example, approximately at least 85%, e.g., at least 90%, e.g., at least 95%) or all of the tube is transparent, and the remainder of the tube is translucent or opaque. In another embodiment, most (for example, approximately at least 85%, e.g., at least 90%, e.g., at least 95%) or all of the tube is translucent.

In some embodiments, the darkened chamber can have a capacity of at least about one liter, and the collection tube can have a capacity of at least about 50 ml. The opening between the darkened chamber and the transparent collection tube can be, for example, in the range of about 19 mm to 22 mm across. The transparent collection tube can have an inner diameter, with at least a portion of which being about 20 mm to 26 mm. The length of the transparent collection tube can be at least about 110 mm. The ratio of the length of dark region (e.g., darkened chamber) to collection tube length can be about 1-3 to 1.

In one embodiment of the invention, a method for separating plankton is described, comprising acclimating a plankton sample comprising zooplankton and phytoplankton in a darkened chamber for a sufficient amount of time to facilitate a response to a change in light intensity; introducing light at a sufficient level to initiate phototactic movement to a collection tube filled with a fluid (e.g., water, for example, filtered water, such as in situ filtered water), wherein the zooplankton is separated from the phytoplankton; collecting a zooplankton sample from the device; and collecting a phytoplankton sample from the device, wherein the plankton is separated to zooplankton and phytoplankton. In particular embodiments, the plankton sample can be a concentrated sample. The concentrated sample can be diluted.

In another embodiment of the invention, a method for separating plankton is described, comprising acclimating a plankton sample comprising zooplankton and phytoplankton in a darkened chamber for a sufficient amount of time to facilitate a response to a change in light intensity; introducing light at a sufficient level to initiate positive phototactic movement of the zooplankton to a fluid-filled collection tube, said tube being of sufficient length to reinforce negative contrast orientation, wherein zooplankton is separated from phytoplankton, collecting a zooplankton sample from the collection tube; and collecting a phytoplankton sample from the collection tube, wherein the plankton is separated to zooplankton and phytoplankton. In one embodiment of the first aspect, the method further includes analyzing (e.g., studying) the sample. In some embodiments, analysis can comprise, e.g., identification, enumeration, and/or quantification of biomass, quantification of pigment fluorescence, etc.

In some embodiments, the invention relates to a method for separating plankton, comprising placing a plankton sample comprising zooplankton and phytoplankton in a darkened chamber; acclimating the plankton for a sufficient amount of time to facilitate a response by the zooplankton to a change in light intensity; and introducing ambient light to the chamber to initiate phototactic movement of the zooplankton to a collection tube filled with water, the phototactic movement into the collection tube separating the zooplankton from the phytoplankton. In some embodiments, the collection tube is of sufficient length to reinforce contrast orientation. In some embodiments, collection tube is transparent. In some embodiments, the collection tube is located below the darkened chamber at a 90° angle relative to a horizontal base of the darkened chamber. In some embodiments, the collection tube has a length sufficient to ensure that an angle of 48° to normal can be achieved by the zooplankton. In some embodiments, the plankton is acclimated for 20 minutes or less.

In some embodiments, the invention relates to a plankton separation method comprising introducing a plankton sample comprising zooplankton and phytoplankton to a darkened chamber of the devices described herein, acclimating the sample for a sufficient amount of time to facilitate a response to a sudden change in light intensity; introducing highly directional ambient light at a sufficient level to initiate phototactic movement to a collection tube filled with water, said tube of sufficient length to reinforce negative contrast orientation, wherein the zooplankton is separated from the phytoplankton, collecting zooplankton from the collection tube; and collecting phytoplankton from the collection tube, wherein the plankton is separated to zooplankton and phytoplankton samples.

In some embodiments, the invention relates to a plankton separating device comprising a darkened chamber having a port, wherein the port has a closure; and a collection tube attached to the port of the chamber for allowing highly directional ambient light, wherein the collection tube is of sufficient length to reinforce migration of the zooplankton, thereby separating plankton into its component parts, wherein the closure is configured to be changed from a closed state to an open state with the collection tube attached to the port. In some embodiments, the closure is a stopper or valve. In some embodiments, the chamber is configured to be positioned above the collection tube during operation, the chamber having an outer perimeter surrounding a central axis, the collection tube being elongated and extending from the darkened chamber along the central axis, starting beyond a point that makes about a 48° angle to the central axis while extending to the nearest location of maximum outer perimeter dimension of the darkened chamber. In some embodiments, the outer perimeter of the darkened chamber and the side walls of the collection tube are generally round.

In some embodiments of the methods, devices and kits described herein, the collection cartridge (tube) is of sufficient length to reinforce contrast orientation. In some embodiments, collection tube is transparent. In some embodiments, the collection tube is located below the darkened chamber at a 90° angle relative to a horizontal base of the darkened chamber. In some embodiments, the collection tube has a length sufficient to ensure that an angle of 48° to normal can be achieved by the zooplankton. In some embodiments, the collection tube is of a sufficient length to reinforce migration. In some embodiments, the collection tube has one of tapered or straight side walls.

In some embodiments, the collection tube extends away from the darkened chamber beyond a point that makes about a 20°±2° angle to the central axis while extending to the nearest location of maximum outer perimeter dimension of the darkened chamber. In some embodiments, at least about 40% of length of the collection tube extends beyond said point that makes said about a 20° angle. In some embodiments, the darkened chamber and the collection tube have outer diameters with a darkened chamber ODb to transparent collection tube ODt ratio of about 3-3.5 to 1, the transparent collection tube having a length with a transparent collection tube length to ODt ratio of about 3.9-5.2 to 1, thereby providing a contrast shadow relative to the transparent collection tube simulating a predator to plankton, and sufficient length in the transparent collection tube for plankton to migrate from and move away from the darkened chamber to minimize plankton collected in the transparent collection tube from migrating back into the darkened chamber. In some embodiments, the darkened chamber has a capacity of at least about one liter, and the collection tube has a capacity of at least about 50 ml. In some embodiments, the opening between the darkened chamber and the collection tube is in the range of about 19 to about 22 mm across. In some embodiments, the collection tube has an inner diameter, at least a portion of which being about 20 mm to about 26 mm. In some embodiments, the length of the collection tube is at least about 110 mm.

In another aspect, a plankton separation method is described using a device of the invention, the method comprising acclimation of a plankton sample comprising zooplankton and phytoplankton in a darkened chamber of the device for a sufficient amount of time to facilitate a response to a change (e.g., a sudden change) in light intensity; introducing highly directional ambient light for phototactic movement of zooplankton from the darkened chamber to a fluid-filled collection tube of sufficient length to reinforce negative contrast orientation; collecting zooplankton from the collection tube; and collecting phytoplankton from the collection tube, wherein the plankton is separated to zooplankton and phytoplankton.

In another aspect, kits are described. In one embodiment, a kit comprising a plankton separation device of the invention and instructions for using the device is described. In another embodiment, the kit can comprise a darkened chamber and a collection tube. In another embodiment, the kit further comprises filtered water. Educational materials can be included in with kits. Educational materials can include, but are not limited to, any materials which serve to impart knowledge, information, or skills, including, but not limited to, instructions for how to use the device; information regarding how to analyze the samples; information regarding water quality, water studies, and/or plankton; and suggestions for age and/or ability appropriate activities and lab exercises, including for those in age group K-12.

In another aspect, the invention encompasses methods of measurement and assays of plankton and plankton related materials using the methods and devices described herein. For example, in one embodiment, the measurement is a measurement of planktonic biomass.

The present invention can also provide a plankton separation or separating device including a darkened chamber having an outer perimeter surrounding a central axis and a first inner width. A darkened transitional area can extend from the darkened chamber along the central axis and have a second inner width that is smaller than the first inner width. A transparent collection container can extend from the darkened transitional area along the central axis for allowing entrance of light therein. The transparent collection container can be of sufficient length to reinforce migration of plankton for separation, and extend beyond a point that makes about a 48° angle to the central axis while extending to the nearest location of maximum outer perimeter dimension of the darkened chamber, and extending away beyond a point that makes about a 20°±2° angle to the central axis while extending to the nearest location of the maximum outer perimeter dimension of the darkened chamber. The transparent collection container can collect zooplankton so that samples of separated zooplankton and/or phytoplankton can be collected.

In particular embodiments, the darkened chamber can have a port. The darkened transitional area can be a darkened transitional adapter coupled to the port of the darkened chamber. The transparent collection container can be a transparent collection tube coupled to the darkened transitional adapter, and have a third inner width that is smaller than the second inner width. The darkened chamber can be generally cylindrical with about a 28 mm inner diameter, a height of about 109 mm, and a volume of about 50 mls. The darkened transitional adapter can have about a 19 mm diameter, a height of about 30 mm, and a volume of about 9 mls. The collection tube can have a initial inner diameter of about 16 mm, and a volume of about 8 mls. In another embodiment, the transparent collection container can be a transparent collection cartridge associated with at least the darkened transitional area. The darkened chamber can be generally cylindrical with about a 25 mm inner diameter, a height of about 100 mm, and a volume of about 50 mls. The darkened transitional area can have about a 19 mm inner diameter, a height of about 5 mm, and a volume of about 1 ml. The transparent collection cartridge can have an inner width or diameter extending from inside the inner diameter of the darkened transitional area and have a volume of about 6 mls.

In some embodiments, the transparent collection cartridge can be a disposable cartridge having a body extending along a central longitudinal axis including an upper body portion positioned in the darkened chamber, and a lower body portion extending from the upper body portion below the darkened chamber. The transparent collection cartridge can be formed of at least one of molded polymer and polymer film. The upper body portion can include a narrowed wall portion for concentrating floating Cyanobacteria into a narrow water column.

In some embodiments, the darkened chamber can be generally cylindrical with about a 25-30 mm inner diameter, and a height of about 100-110 mm, the darkened transitional area can have about a 20 mm±2 mm inner diameter, and a height of about 3-30 mm, and the transparent collection container can have an initial inner diameter of about 16-20 mm and a length of about 44-70 mm.

The present invention can also provide a collection cartridge for a plankton separating device that can be disposable. The cartridge can have a body extending along a central longitudinal axis including an upper body portion for insertion and positioning in a darkened chamber of the plankton separating device. An upper region of the upper body portion can have a narrowed wall portion for concentrating floating Cyanobacteria into a narrow water column. A lower transparent body portion that is narrower than the upper body portion can extend from the upper body portion for allowing entrance of light therein forming a transparent collection container. The transparent collection container can have sufficient length to reinforce migration of plankton for separation.

In particular embodiments, the body of the collection cartridge can include a polymer film tube having upper right and left heat seal lines in the upper region of the upper body portion inwardly from respective right and left sides of the polymer film tube, forming the narrowed wall portion. Lower right, bottom and left heat seal lines can be in the lower transparent body portion inwardly from respective right, bottom and left sides of the polymer film tube, forming a transparent collection container.

The present invention can also provide a method for separating plankton including placing a plankton sample comprising water, zooplankton and phytoplankton in a separation or separating device. The separating device can include a darkened chamber having an outer perimeter surrounding a central axis and a first inner width, a darkened transitional area extending from the darkened chamber along the central axis having a second inner width that is smaller than the first inner width, and a transparent collection container extending from the darkened transitional area along the central axis for allowing entrance of light therein. The transparent collection container can be of sufficient length to reinforce migration of plankton for separation, and extending beyond a point that makes about a 48° angle to the central axis while extending to the nearest location of maximum outer perimeter dimension of the darkened chamber, and extending away beyond a point that makes about a 20°±2° angle to the central axis while extending to the nearest location of the maximum outer perimeter dimension. Light can be introduced to the separation device to initiate phototactic movement of the zooplankton to the transparent collection container. Separated zooplankton and/or phytoplankton samples can be collected from the separation device.

In particular embodiments, the darkened chamber comprises a port. The darkened transitional area can be a darkened transitional adapter coupled to the port of the darkened chamber. The transparent collection container can be a transparent collection tube coupled to the darkened transitional adapter and have a third inner width that is smaller than second inner width. The darkened chamber can have a generally cylindrical shape having about a 28 mm inner diameter, a height of about 109 mm, the volume of about 50 mls. The darkened transitional adapter can have about a 19 mm inner diameter, a height of about 30 mm, and a volume of about 9 mls. The collection tube can have an initial diameter of about 16 mm, and a volume of about 8 mls. In another embodiment, the transparent collection container can have a transparent collection cartridge associated with at least the darkened transitional area. The darkened chamber can have a generally cylindrical shape having about a 25 mm inner diameter, a height of about 100 mm, and a volume of about 50 mls. The darkened transitional area can have about a 19 mm inner diameter, a height of about 5 mm, and a volume of about 1 ml. The transparent collection cartridge can have an inner diameter extending from inside the inner diameter of the darkened transitional area, and a volume of about 6 mls.

In some embodiments, the transparent collection cartridge can be a disposable cartridge having a body extending along a central longitudinal axis with an upper body portion for insertion and positioning in the darkened chamber, and a lower body portion extending from the upper body portion below the darkened chamber. The transparent collection cartridge can be formed from at least one of molded polymer and polymer film. The upper body portion can comprise a narrowed wall portion for concentrating floating Cyanobacteria into a narrow water column.

In some embodiments, the darkened chamber can have a generally cylindrical shape having about a 25-30 mm inner diameter, and a height of about 100-110 mm, the darkened transitional area can have about a 20 mm±2 mm inner diameter, and a height of about 3-30 mm, and the transparent collection container can have an initial inner diameter of about 16-20 mm and a length of about 44-70 mm.

The plankton sample can be maintained in a darkened state for about 2 hours, and the zooplankton can be separated from the phytoplankton for about 30 minutes while illuminated with light, such as ambient light. The plankton separating device can be oriented in an upright position with the darkened chamber being above the transparent collection container. The plankton sample can comprise Cyanobacteria, and the phytoplankton can be concentrated in the darkened chamber. The Cyanobacteria can be concentrated in an upper 3-5 mls of the darkened chamber and removed. Openable closure devices can be on the top of the darkened chamber and on a distal end of the transparent collection container, allowing for the introduction and removal of samples.

The present invention can also provide a method of concentrating cyanobacteria including collecting a concentrated Cyanobacteria sample through the use of a mesh plankton net, wherein the collecting is performed in a manner that enables the sample to reduce in volume to completely fill a cod end of the plankton net. The sample can be placed in a dark and cool environment. The sample can be kept in the environment for a minimum holding period of about 2 hours. Conditions are provided so that the sample can be separated in an additional 30 minute separation period following the holding period, for example in light, such as ambient light, wherein the conditions allow for removal of zooplankton from the Cyanobacteria sample and allow the cyanobacteria to achieve positive buoyancy.

In particular embodiments, the mesh plankton net is about a 50 um mesh plankton net. The Cyanobacteria sample can be allowed to undergo a process of respiration while in the dark and cool environment for about 2 hours, thereby allowing the consumption of carbohydrates within the Cyanobacteria, decreasing the weight of the carbohydrate ballast within the Cyanobacteria and increasing the relative buoyancy of the Cyanobacteria causing the Cyanobacteria to float in water. The sample can be placed in the plankton separating device previously described after the sample is collected, and such as after the process of respiration.

The present invention can also provide a method of assembling a collection cartridge in a plankton separating device including providing the collection cartridge with a body extending along a central longitudinal axis having an upper body portion. An upper region of the upper body portion can have a narrowed wall portion. A lower transparent body portion that is narrower than the upper body portion can extend from the upper body portion. The upper body portion and the narrowed wall portion can be inserted and positioned into a darkened chamber of the plankton separating device. The narrowed wall portion can concentrate floating Cyanobacteria into a narrow water column. The lower transparent body portion can extend out from the darkened chamber for allowing entrance of light therein forming a transparent collection container of sufficient length to reinforce migration of plankton for separation.

In particular embodiments, the collection cartridge can be provided with a body that includes a polymer film tube having upper right and left heat seal lines in the upper region of the upper body portion inwardly from respective right and left sides of the polymer film tube, forming the narrowed wall portion. Lower right, bottom and left heat seal lines in the lower transparent body portion inwardly from the respective right, bottom and left sides of the polymer film tube, can form the transparent collection container.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 1G-1I show further embodiments of the separation device.

FIG. 1L is a front view of a ball valve connected to a filter cone and cartridge.

FIG. 1M is a side view of an embodiment of a separation device in the present invention including a securement arrangement.

FIGS. 7C and 7D are graphs showing separation efficiency curves for macrozooplankton biomass versus microcystis equivalents and chlorophyll in Willand Pond Sep. 5, 2013 and Oct. 16, 2013.

FIGS. 8A and 8B are graphs showing separation efficiency curves for macrozooplankton biomass versus microcystis equivalents and chlorophyll in Lake Cochichewick Sep. 4, 2013, Oct. 10, 2013, and Oct. 29, 2014.

FIGS. 8C and 8D are graphs showing separation efficiency curves for macrozooplankton biomass versus microcystis equivalents and chlorophyll in Willand Pond Sep. 5, 2013, Oct. 16, 2013 and Sep. 6, 2014.

FIG. 11 is a table of separation efficiencies for zooplankton biomass as observed in Lake Cochichewick 2013-2014.

FIG. 12 is a table of separation efficiencies for zooplankton biomass as observed in Willand Pond 2013-2014.

DETAILED DESCRIPTION OF THE INVENTION

Figure 1A:
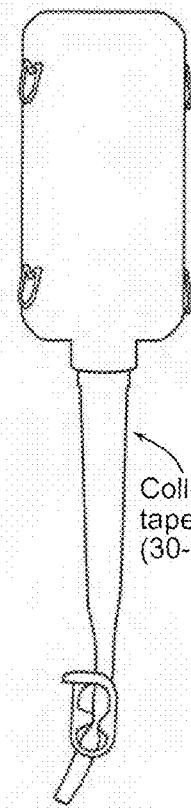
FIGS. 1A-1C show an embodiment of the separation device, having a darkened chamber (10-1; amber bottle), closure for temporary physical separation (20-1, stopper), collection tube (30-1; tube with tapered end) and optional external support (40-1; sling support).
Figure 1B:
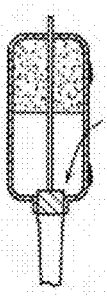
Figure 1C:
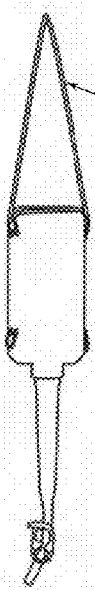

A description of example embodiments of the invention follows.

Described herein are methods and devices for limnological studies using plankton separation, for analysis, bioaccumulation selectivity and evaluation of biological community associations. It was found that the methods and devices of the invention allow the researcher to rapidly collect samples for improved routine surveillance programs and ecological risk assessments in situ.

The structure of planktonic populations in the aquatic ecosystems is dynamic and constantly changing in species composition and biomass distribution. Changes in species composition and biomass distribution may affect separation efficiency.

Plankton, particularly phytoplankton, have long been used as an indicator of water quality. Because of their short life spans, plankton responds quickly to environmental changes. Some species are very sensitive to organic and/or chemical wastes. Some species have also been associated with noxious blooms causing toxic conditions apart from taste and odor problems. The presence of toxins and potential for bioaccumulation threaten fresh water ecosystems, humans and animals.

The physical and chemical characteristics of water affect the abundance, species composition, stability and productivity of indigenous populations of aquatic organisms. The biological methods used for analyzing (e.g., assessing) water quality include, but are not limited to, collection, counting and identification of aquatic organisms; biomass measurements; measurements of metabolic activity rates; toxicity tests; potential for bioaccumulation of pollutants; and processing and interpretation of biological data. The work involving plankton analysis aids in the explanation of the cause of color and turbidity and the presence of objectionable odor, tastes and visible particles in waters; the interpretation of chemical analyse; and the identification of the nature, extent and biological effects of pollution. It also provides data on the status of an aquatic system on a regular basis. The process of plankton separation provides a sample of adequate size and improved quality for postanalytical techniques that include, but are not limited to, assays such as enzyme-linked immunosorbent assay (ELISA), inhibition assays and radioassays.

Numerous studies have been conducted on the occurrence of the Cyanobacteria and the toxins that they produce (Carmichael and Falconer 1993, Yoo et al., 1995, Carmichael 1997). Many studies have been conducted to further our understanding of the complex dynamics of Cyanobacterial abundance and community composition as they are affected by water temperature, solar irradiance, hydrology, nutrient supply and meteorological conditions. A report (Lopez et al. 2008) outlines current and future efforts that would support and expand understanding of the Cyanobacteria, cyanotoxins, ecological impacts, human health effects and management techniques. In the report, the need to improve monitoring techniques was recommended for surveillance programs and ecological risk assessments. For example, routine surveillance programs can be improved with the use of the cost-effective methods and devices described herein to determine the relative contribution of the Cyanobacteria to the phytoplankton assemblage. Additionally, the toxicity of the Cyanobacterial community can be assessed with a rapid, cost effective method to obtain samples that yield precise measures of phytoplankton biomass and weight specific toxicity. This information can be used to determine trends in the ecological integrity of the aquatic systems and support the decision making process regarding use attainment. Ecological risk assessments of bioaccumulation in zooplankton (i.e., bulk zooplankton, macrozooplankton) can be simplified and improved with a rapid, cost effective method to obtain samples that yield precise measures of zooplankton biomass and weight specific toxicity.

Sampling and monitoring of waterways is largely done by state and federal agencies with assistance from volunteers. Methods and devices that are easy to use and do not require expensive or complex systems or parts for obtaining samples are needed. The methods and devices of the present invention meet these needs. Routine surveillance programs are benefited by the cost effective methods and devices described herein that can assess the toxigenicity of the Cyanobacterial community. This information can be used to determine trends in ecological integrity and support the decision making process regarding use attainment. The calculation of dry weight biomass and weight specific toxicity is simplified and improved with the methods of the invention for separating plankton samples into its component parts. Routine surveillance programs using biological community associations can be enhanced with a rapid method for collection of samples for analysis. Furthermore, ecological risk assessments are improved using the methods and devices for the evaluation of toxin in different trophic levels, including quantification of cyanotoxins in phytoplankton and the resulting accumulation in zooplankton.

Previous studies have utilized phototactic behavior to separate plankton into its components to quantify cyanotoxins in the phytoplankton and subsequent transfer to the zooplankton (Capron 1995, Johnson 1999, Hathaway 2001, Larsson et al. 2001, Jonasson et al., 2010, Haney 2013, Jonasson, 2013). Phototactic behavior (swimming) is a stimulus response that requires a velocity (kinesis) and a direction (orientation). To take advantage of this naturally occurring phenomenon, the researcher must establish a set of necessary conditions before the phenomenon occurs (Nagel 1974). A hierarchy of response (Loose 1993) to stimulus would include the relative change in light intensity (Ringelberg 1964) which would exceed the rheobase (Ringelberg, 1964, Daan and Ringelberg, 1969) necessary to initiate a swimming response. A positive phototactic response could be anticipated as a result of exposure to a narrow stimulus beam (Forward 1988) (highly directional light) with an angular light distribution that approximates 0° (Schallek 1942). Body axis orientation would result from dorsal beam contrast (45° or less) (Ringelberg 1964) (Ringelberg, Flik and Buis 1975) that would control the direction of movement in the vertical plane. The orientation of the device (darkened above, light below) serves to reinforce body axis orientation as a flight response from predators. The swimming velocity (Daan and Ringelberg, 1969) would have to be sufficient to migrate the distance in the time allowed. Any barriers such as spatial requirements, temperature, pressure, angular light distribution, and other environmental conditions would have to be overcome. In previous studies as noted, the necessary conditions for the phenomenon to occur were met with each researcher modifying the conditions somewhat (spatial requirements, light source, time, distance and temperature). For example, previous researchers provided illumination, followed by waiting 2 hours, five (5) minutes, 15 minutes and twenty (20) minutes before collecting their respective zooplankton samples. In addition, various volumes were collected. These methods resulted in reduced separation efficiency.

The methods and devices of the invention allow for the qualitative and quantitative analysis of plankton. Such studies can monitor the impact of environmental changes on ecological integrity. The methodology and devices simplify and reduce costs associated with monitoring programs while improving the accuracy of the data collected. The device and methods described herein utilize phototactic behavior and contrast orientation for maximal in situ separation of phytoplankton and zooplankton. Further, gathering quantitative data on separation efficiencies, the development of conditions necessary for a desired result based on research objectives can be achieved.

As used herein, "plankton" refers to a diverse group of organisms that live in fresh or salt water. Plankton is usually free floating, suspended in water, nonmotile or insufficiently motile to overcome transport by water currents. Plankton includes phytoplankton and zooplankton.

Phytoplankton generally live near the water surface where there is sufficient light to support photosynthesis. Examples of phytoplankton include, for example, algae, diatoms, Cyanobacteria, dinoflagellates and coccolithophores. Phytoplankton can be, for example, unicellular, colonial or filamentous, and is autotrophic (primarily photosynthetic) and can be eaten by zooplankton and other organisms occurring in the same environment.

Cyanobacteria is photosynthetic bacteria found in freshwater and marine environments, including lakes, streams, ponds, the ocean and other surface waters. Cyanobacteria can include planktonic cells or phototrophic biofilms. It can reproduce exponentially to form extensive and highly visible blooms. This blooming Cyanobacteria can produce cyanotoxins in such concentrations that they poison and even kill animals and humans. Cyanotoxins can also accumulate in other animals such as fish and shellfish, and cause poisonings such as shellfish poisoning. Among cyanotoxins are some of the most powerful natural poisons known, including poisons which can cause death by respiratory failure. The toxins include neurotoxins, cytotoxins, hepatotoxins, and endotoxins.

Zooplankton include, for example, microscopic protozoans, rotifers, cladocerans and copepods and other aquatic organisms. The species assemblage of zooplankton also may be useful in assessing water quality. Zooplankton can be further separated into size classes, such as macrozooplankton and microzooplankton. Macrozooplankton include, but are not limited to, microcrustaceans larger than 63 ums (microns), including but not limited to Cladocerans: *Bosmina* spp., *Chydorineae* spp., *Ceriodaphnia* spp., *Daphnia* spp., *Diaphanosoma* spp.; and Copepods: Calanoids—female, Calanoids—male (*Diaptomus* spp.), *Microcyclops* spp., *Mesocyclops* spp., and all stages of copepodites. Microzooplankton include, but are not limited to, microcrustacean nauplii and rotifers larger than 20 um, such as 20-63 microns, including, but not limited to: *Keratella* spp., *Kellicottia* spp., *Trichocera* spp., *Asplancha* spp., and *Ascomorpha* spp.

As used herein, "phototaxis" refers to locomotory movement that occurs when a whole organism moves responds to a relative change in light intensity. This can be advantageous for phototrophic organisms as they can orient themselves most efficiently to receive light for photosynthesis. Phototaxis is positive if the movement is in the direction of increasing light intensity and negative if the direction is opposite. The variables that initiate phototactic behavior and maximize migration in the present disclosure include but are not limited to, the relative change in light intensity (e.g., without the use of an artificial light source or filter(s)).

As used herein, "contrast orientation" refers to locomotory movements that occur when a whole organism responds to a spatial change in light intensity. This is advantageous to phototactic organisms as they can orient themselves most efficiently to respond to light/dark boundaries that may indicate the presence or absence of predators. Contrast orientation can be positive or negative.

In some embodiments, the plankton is acclimated in the chamber. Acclimation for a "sufficient amount of time" means a sufficient amount of time to facilitate a response by the plankton to a change in light intensity, for example, between about 20 and about 45 minutes. In one embodiment, the time is about 20 minutes or less, e.g., about 20 minutes.

The selection of plankton separation times can be based on a number of factors, including, for example, the potential for reverse migration by the zooplankton (for example, about 0-60 minutes, e.g., 1 hr.) and phytoplankton contamination of the zooplankton portion as a result of gravity. The desirable phytoplankton "contamination" level typically does not exceed 5%.

As used herein, "sampling" refers to collecting a sample, e.g., a water sample, comprising plankton for monitoring. As used herein, "migration potential" is the distance traveled by an organism in a desired timeframe.

As used herein, "plankton net" refers to a type of field equipment used to trap plankton. It typically has a polyethylene filter of a defined mesh size and a graduated measuring jar attached to the other end. A handle or ring can hold the net. The mesh size of the net determines the size range of the plankton trapped. For example, a mesh of 50 ums can be used for collecting samples.

Example devices are shown in FIGS. 1A-1I. The chamber (10-1) can be of a dark color (e.g., black, amber) and constructed of a durable material, in some embodiments with a conical shape and smooth walled. The chamber is constructed so that light is prevented from entering the chamber during the separation phase. For example, the chamber can have at least one port (12) with a closure for temporary separation (20) (e.g., stopper with plastic rod (20-1), valve, ball valve (20-2) screw cap, or other mechanism to stop fluid communication as needed). In another aspect, the chamber has one or more additional sample port(s) (14) for introduction of the water and/or sample. In certain embodiments, the sample port is located at the top of the chamber and can be of a sufficient size for introduction of sample. The sample port (opening) includes a closure (16), for example a cap (16-1). The port (14) can act as a sample port if there is only one port. The port can have openings to the interior of the chamber that further have a closure.

During the separation phase, the internal chamber is darkened and a temporary physical separation (e.g., a closure) between the chamber and a collection tube (30) is removed. The collection tube is of a sufficient size and material to facilitate migration of the zooplankton. The collection tube is attached to the chamber (10-1) via a port (12) and is transparent or translucent or can become transparent for allowing a sufficient amount of highly directional ambient light to enter and facilitate collection of zooplankton.

In a certain embodiment, the collection tube is conical in shape to facilitate the collection of zooplankton. The length of the collection tube can be selected so that the zooplankton can migrate past a 48° angle to the normal within the tube. The collection tube optionally includes a valve (32) e.g., a ratchet valve (32-1), or clamp to permit or stop flow of the zooplankton. The collection tube can be a tapered tube. In alternative embodiments, the tube has a screw cap on one end and blunt end with cap on the other. The collection tube is of sufficient length for migration and separation of the components of the plankton. In certain embodiments, the separation chamber includes an external support to the device (40) for example, a bridle/sling (40-1) assembly and/or external rings, for positioning the chamber for use with a table stand (40-2) or a clamping device (40-3).

Figures 1D, 1E, 1F:
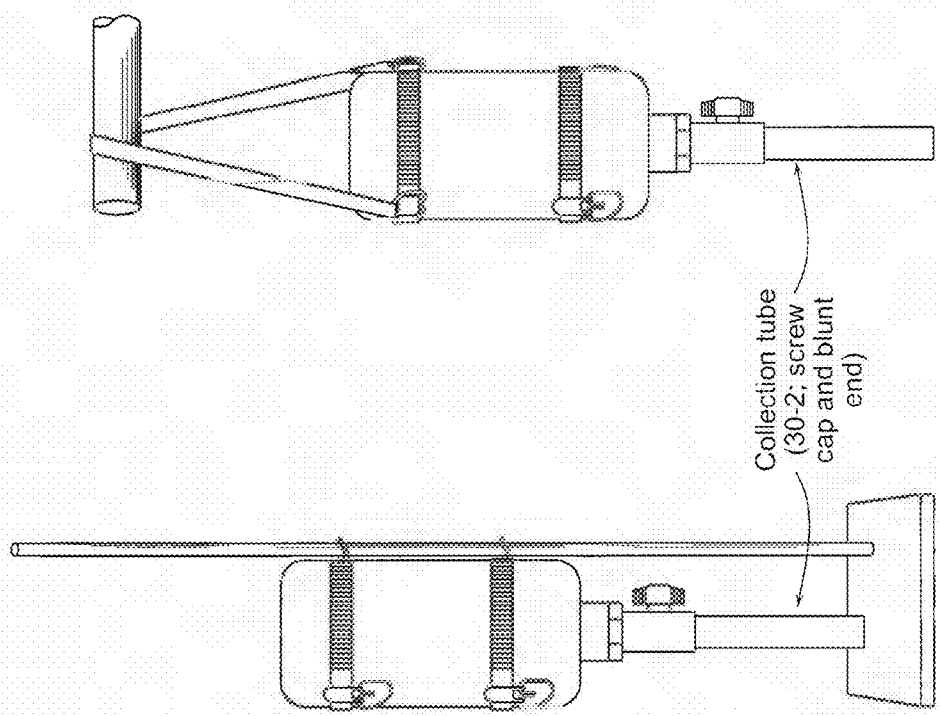
FIGS. 1D-1F show other embodiments of the device, with external support of rings, a table support, and a c-clamp system.
Figure 1J:
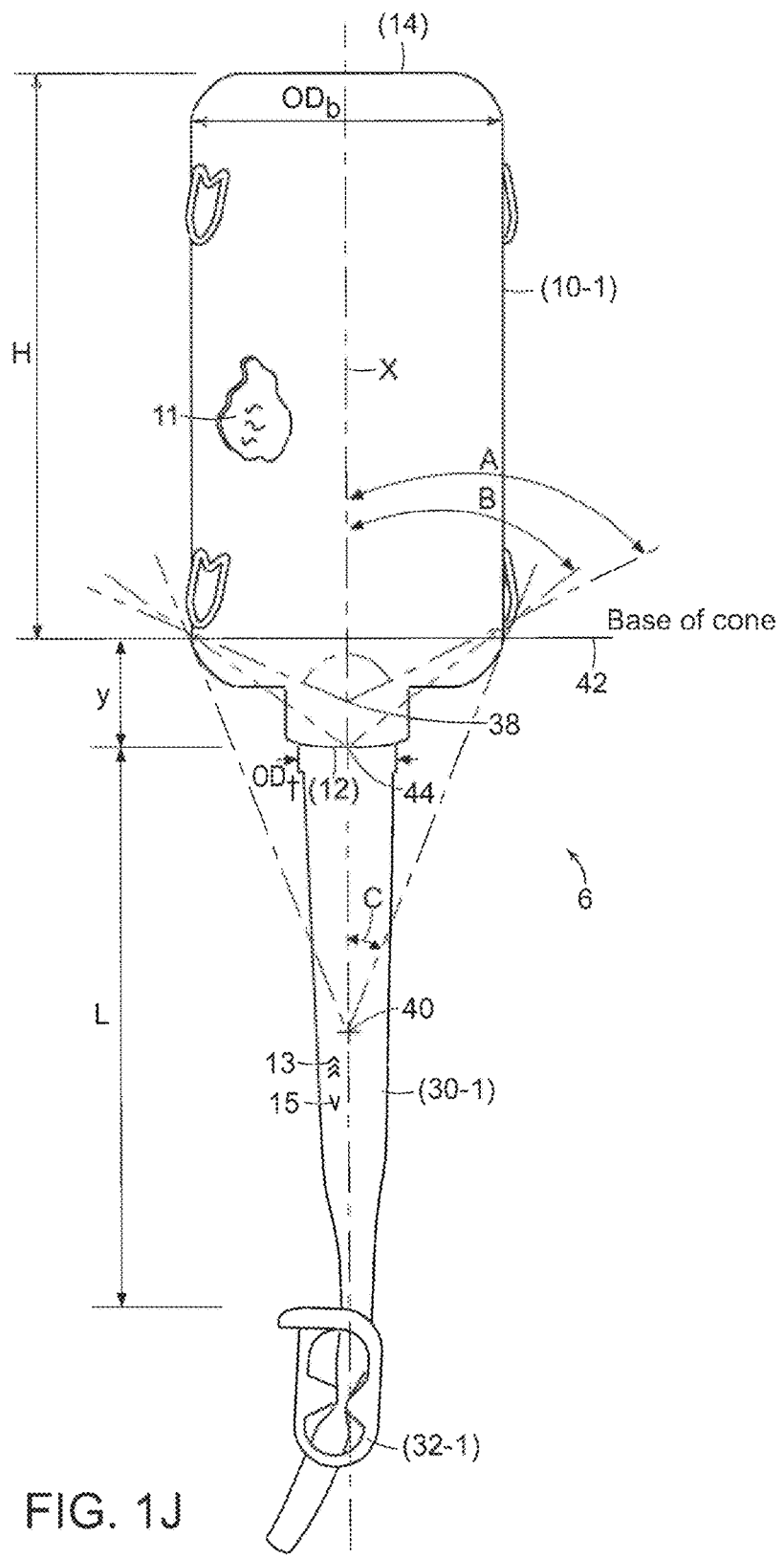
FIG. 1J is a front view of the embodiment of FIG. 1A with annotations.

Referring to FIG. 1J, the darkened container or chamber (10-1) of separating device 6 for containing a sample 11 of water and plankton for separation, can be a generally cylindrical bottle with a circular or round outer perimeter or side wall, and have a height H with a generally constant outer diameter $OD_b$ that concentrically surrounds a longitudinal central axis X. The collection chamber, region, container or tube (30-1) for containing filtered water 13 into which desired plankton 15 can be collected, can be connected to and sealed to the darkened chamber (10-1) at a central outlet, opening or port (12). The collection tube (30-1) can extend in a straight manner from the darkened chamber (10-1) along or aligned with the longitudinal central axis X. The collection tube (30-1) is typically transparent and typically operates with existing ambient light, and can have a tapered shape or side walls, being widest at port (12) and narrowest at ratchet clamp or valve (32-1). In some embodiments, the device comprises a single port.

The separating device 6 can be configured to be used in operation with the darkened chamber (10-1) being positioned above the transparent collection tube (30-1), for example with the longitudinal central axis X being vertical or near vertical. This can allow plankton such as phototactic zooplankton that are attracted to light, such as ambient light on, within or illuminating the transparent collection tube (30-1), to move or swim vertically downwardly from darkened chamber (10-1) with gravity into the transparent collection tube (30-1). Higher percentages of such plankton tend to swim vertically downwardly with gravity to light, in comparison to swimming to light horizontally or laterally, or vertically upwardly against gravity. Therefore, positioning the transparent collection tube (30-1) vertically below the darkened chamber (10-1) can maximize desired plankton migration toward light to obtain maximum or high separation efficiencies. In addition, the port (12) between the darkened chamber (10-1) and the transparent collection tube (30-1) can have a small opening in comparison to the outer perimeter diameter $OD_b$ (about ⅓ in size), which produces a narrow defined circular beam or spot of light with high contrast from the transparent collection tube (30-1) vertically upwardly from below along longitudinal axis X into darkened chamber (10-1), which draws phototactic plankton 15 downwardly vertically into the transparent collection tube (30-1). If the port (12) is too large, too much light can diffuse into the bottom of the darkened chamber (10-1), and not provide enough contrast or definition between dark and light to cause the plankton 15 to migrate into the transparent collection tube (30-1).

The 48° to normal cone angle, is the angle A which is measured 48° relative to the longitudinal central axis X and a line extending from a point 38 along longitudinal axis X that intersects or passes through a horizontal or lateral base line 42 at the widest or maximum perimeter or diameter side wall dimension location of darkened chamber (10-1) that is closest to the transparent collection tube (30-1). The longitudinal axis X is normal to lateral line 42. A shadow of an object such as darkened chamber (10-1) above plankton 15 (such as zooplankton that have migrated into transparent collection tube (30-1)), at a cone angle of 48° or less, can form a concentric contrast shadow relative to the plankton 15 within the interior of the transparent collection tube (30-1). That contrast shadow can simulate a predator to the plankton 15, which tends to cause the plankton 15 to swim downwardly within the transparent collection tube (30-1) away from the darkened chamber (10-1) to maintain separation of the plankton in separating device 6. If angle A is larger than 48°, the shadow of the darkened chamber (10-1) typically does not provide enough contrast between light and dark to the plankton 15 to simulate a predator, and some of the plankton 15 within the transparent collection tube (30-1) tends to migrate back into the darkened chamber (10-1). As can be seen in FIG. 1J, the 48° angle A is located within the darkened chamber (10-1), and the cone angle B measured relative to longitudinal axis X and a line extending from a point 44 along longitudinal axis X, at the transition between the darkened chamber (10-1) and the transparent collection tube (30-1), to the outer perimeter of darkened chamber (10-1) on base line 42, is less than 48°. Angle B is the angle that plankton 15 can migrate past and view the concentric contrast shadow of the darkened chamber (10-1). This angle B is less than 48°, such as 41° in some embodiments, and forms a concentric angle and contrast shadow simulating a predator in all directions when the darkened chamber (10-1) and the transparent collection tube (30-1) are both round, that drives the plankton within the transparent collection tube (30-1) downwardly away from the darkened chamber (10-1). The transparent collection tube (30-1) is sufficiently long enough to allow the plankton 15 to swim far enough downwardly away from the darkened chamber (10-1) with gravity to not migrate upwardly back into the darkened chamber (10-1) against gravity.

In some embodiments, the darkened chamber (10-1) can be a light impermeable plastic, glass or metal bottle for holding a sample 11 of about 1 liter, and the transparent collection tube (30-1) can be a clear or transparent tapered elongate plastic or glass tube for holding or containing about 50 ml of filtered water 13 and collected plankton 15. The darkened chamber (10-1) can have a height H of about 166 mm (6.5 in) with a maximum outer perimeter diameter $OD_b$ portion of about 94 mm (3.7 in) that is constant until reaching the top of the darkened chamber (10-1). The darkened chamber (10-1) can narrow down from the outer perimeter diameter $OD_b$ of 94 mm at line 42 to about 30 mm (1.2 in) at port (12) over a distance Y that can be about 50 mm (2 in). The transparent collection tube (30-1) can have a length L of about 150 mm (5.9 in) between port (12) and ratchet valve (32-1). The transparent collection tube (30-1) can be round and have a maximum outer diameter $OD_t$ at port (12) of about 29.5 mm (1.2 in) with a corresponding inner diameter $1D_t$ of about 21.5 mm (0.85 in). The opening into the transparent collection tube (30-1) from darkened chamber (10-1) can be about 21 mm±2 mm (0.83 in ±0.08 in). It has been found that smaller openings into the transparent collection tube (30-1), such as 13 mm, hinder the migration of phototactic plankton and result in lower separation efficiencies. At the ratchet valve (32-1) at the bottom, the outer diameter can taper to about 10 mm (0.4 in) with a corresponding inner diameter of about 7 mm (0.3 in). Port (14) at the top of darkened chamber (10-1) can have a diameter of about 69 mm (2.7 in). Angle B can be about 41°±2°. The transparent collection tube (30-1) can form a narrow circular or round tapering column of water exposed to ambient light, extending downwardly concentrically from darkened chamber (10-1), starting with about ⅓ the diameter of the darkened chamber (10-1).

A cone angle C of about 20°±2°, such as 19°, can extend relative to the longitudinal axis X and a line extending from point 40 along longitudinal axis X within transparent collection tube (30-1) to the maximum outer perimeter diameter $OD_b$ at base line 42. Plankton 15 migrating past cone angle C will not tend to migrate back into the darkened chamber (10-1). About 40% of the length of transparent collection tube (30-1) can extend downwardly below the 19° angle C. This provides enough downwardly vertical space within transparent collection tube (30-1) past angle C where collected plankton 15 can swim downwardly far enough away from darkened chamber (10-1) in response to the simulated predatory contrast shadow produced, where the plankton will not migrate back into the darkened chamber (10-1). The darkened chamber outer diameter $OD_b$ and the transparent collection tube outer diameter $OD_t$ can have an $OD_b$ to $OD_t$ ratio of about 3-3.3 to 1, such as about 3.2 to 1, and there can also be an $OD_b$ to transparent collection tube inner diameter $ID_t$ ratio, $OD_b$ to $ID_t$ ratio of about 4.2-4.6 to 1, such as about 4.4 to 1. The transparent collection tube (30-1) can have a length L to outer diameter $OD_t$ ratio of about 5-5.2 to 1, such as 5.1 to 1, and a L to $1D_t$ ratio of about 6.8-7.2 to 1, such as about 6.9 to 1. The ratio of the dark region length of darkened chamber (10-1) to transparent collection tube length L can be about 1.2-1.6 to 1 such as about 1.4 to 1. Such configurations, dimensions and ratios can maximize separation efficiencies of plankton separation, by using plankton's migration responses to light and predators.

Figure 1K:
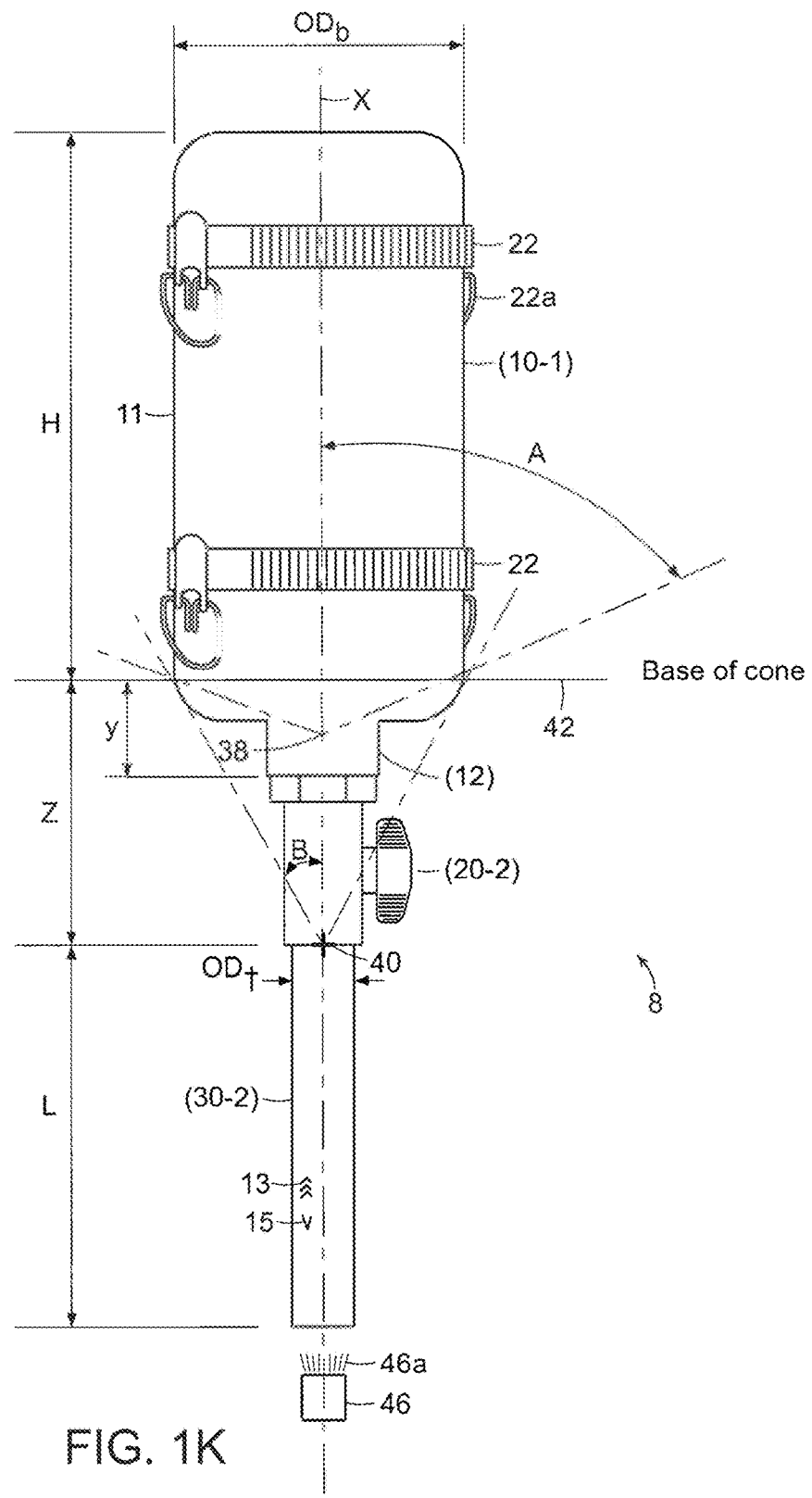
FIG. 1K is a front view of the embodiment of FIG. 1D with annotations.

Referring to FIG. 1K, the darkened chamber (10-1) of separating device 8 can be similar to that in separating device 6, and can have similar construction, shape and dimensions as previously discussed. Separating device 8 can differ in that instead of having a closure stopper (20-1) for initially separating the sample 11 within the darkened chamber (10-1) from the transparent collection tube (30-1), a valve (20-2) such as a ball valve, can be mounted or connected to port (12) of the darkened chamber (10-1), and a transparent collection chamber, region, container or tube (30-2) for typically operating in ambient light, can be connected to the bottom or lower end or outlet of valve (20-2). The location of base line 42 and the 48° cone angle A relative to darkened chamber (10-1) are similar to that in separating device 6. However, the valve (20-2), which can be dark or light impermeable, forms a longer darkened region relative to base line 42 along longitudinal axis X, before reaching transparent collection tube (30-2), that can have a distance Z of about 135 mm (5.3 in). The valve (20-2) can have an opening therethrough with an inner diameter of about 20 mm (0.78 in)±2 mm (0.08 in). The valve (20-2) connected to the darkened chamber (10-1) can form a narrow circular dark column extending concentrically downward from darkened chamber (10-1) before reaching transparent collection tube (30-2), that can be about 121 mm (4.8 in) long. The transparent collection tube (30-2) can extend in a straight manner from valve (20-2) along longitudinal axis X, a length of about 111 mm (4.4 in), and can be round or cylindrical with a side wall having a constant outer diameter $OD_t$ of about 28 mm (1.1 in) and an inner diameter $1D_t$ of about 25 mm (0.98 in). The collection tube (30-2) can form narrow circular, round or cylindrical column of water 13 exposed to ambient light, extending downwardly concentrically from darkened chamber (10-1) and valve (20-2), having about ⅓ the diameter of darkened chamber (10-1).

The transparent collection tube (30-2) can be used for containing about 50 ml of filtered water 13 and collected plankton 15. The use of the ball valve (20-2) instead of closure stopper (20-1) can provide separating device 8 with more consistent separation results than with separating device 6. The ball valve (20-2) can open the path or port (12) between the darkened chamber (10-1) and the transparent collection tube (30-2) in a repetitive smooth consistent manner, with a twist of a knob. With regard to closure stopper (20-1) in separating device 6, a stopper is pushed into or pulled from port (12) by a stick or rod. Cone angle B is measured relative to longitudinal axis X and a line extending from a point 40 along longitudinal axis X at the transition between the darkened valve (20-2) and the transparent collection tube (30-2), that intersects the outer diameter $OD_b$ at base line 42, and is less than 48°. In some embodiments, angle B can be about 20°±2°, such as 19° and can form a concentric contrast shadow of the darkened chamber (10-1) relative to the plankton 15 within the interior of the transparent collection tube (30-2) that effectively simulates a predator to the plankton 15. This can cause the plankton 15 to swim downwardly with gravity within transparent collection tube (30-2) away from the darkened chamber (10-1) to maintain separation of desired plankton. Although a 19° angle B is less than half that of 48°, the 19° angle is very effective to prevent plankton 15 within transparent collection tube (30-1) from migrating back into darkened chamber (10-1) against gravity, and the full length L of transparent collection tube (30-2) extends below point 40 of the 19° angle B to allow plenty of room for the plankton 15 to migrate downwardly away from darkened chamber (10-1) and valve (20-2) with gravity. The darkened chamber outer diameter $OD_b$ and the transparent collection tube outer diameter $OD_t$ can have an $OD_b$ to $OD_t$ ratio of about 3.3-3.5 to 1, such as 3.4 to 1, and there can also be an $OD_b$ to transparent collection tube inner diameter $ID_t$ ratio, $OD_b$ to $ID_t$ ratio of about 3.5-4 to 1, such as 3.8 to 1. The transparent collection tube (30-2) can have a length L to outer diameter $OD_t$ ratio of about 3.9-4.2 to 1, such as 4 to 1, and a L to $1D_t$ ratio of about 4.2 to 4.6 to 1, such as 4.4 to 1. The ratio of the dark region length consisting of darkened chamber (10-1) and valve (20-2) to transparent collection tube length L can be about 2.5-2.9 to 1, such as 2.7 to 1. About 40% of the darkened region can be a narrow or circular column extending through valve (20-2). These configurations, dimensions and ratios can also maximize separation efficiencies of plankton separation, and also uses plankton's migration responses to light and predators. Although separating devices 6 and 8 typically make use of ambient light entering transparent collection tubes (30-1) and (30-2). If desired, a reflector or a light source 46 can be used and positioned below or to the side of the devices 6 and 8 for directing light 46a upwardly into collection tubes (30-1) and (30-2).

The separation devices 6 and 8 are able to obtain higher separation efficiencies of plankton than prior devices. The stopper (20-1) or valve (20-2) can keep the sample 11 to be separated, both physically and phototactically isolated within the darkened chamber (10-1) from the transparent collection tubes (30-1) and (30-2), until opened. The vertical orientation of the darkened chamber (10-1) being above the transparent collection tubes (30-1) and (30-2) with a circular beam or spot of light being directed vertically upward through a relatively small port (12) in the darkened chamber (10-1) provides defined light to dark contrast that promotes initial migration of phototactic plankton 15 downwardly toward the light while assisted by and in the direction of gravity. The opening between the darkened chamber (10-1) and the transparent collection tube is sized small enough to provide an attractive defined high contrast beam of light, while large enough not to impede plankton migration. An opening that is too large can let too much light into the darkened chamber (10-1) so there is not a sufficient light to dark contrast, and not promote migration. The transparent collection tubes extend straight down from the darkened chamber (10-1) so that migrating plankton 15 can swim past a 48° angle or less to the longitudinal axis X as described above, such as beyond a 41° point or a 19° or 20° point, within the transparent collection tube. The plankton 15 view the concentric contrast shadow of the darkened chamber (10-1) as a predator and tend to move downwardly with gravity, and not migrate back into the darkened chamber (10-1) against gravity. By having a large enough collection sample, such as at least 50 mls, the transparent collection tube can have a length that is long enough for the plankton 15 to swim far enough downwardly away from the darkened chamber (10-1) and not to migrate back in. The transparent collection tube can extend at least about 40% of the length L of the transparent collection tube beyond the point that makes about a 20°±2° angle to the longitudinal axis X as previously described. In separating device 8, the whole length L of transparent collection tube (30-2) extends beyond the point of the 19° or 20° angle. By having a relatively narrow diameter transparent collection tube, the contrast shadow that the plankton 15 therein sees, can have a relatively consistent viewing angle in all directions. Although particular dimensions have been given, the dimensions can vary, for example, larger darkened chambers and transparent collection tubes can be used.

Referring to FIG. 1L, valve (20-2) can be connected to a phytoplankton cartridge and filter cones for processing, as desired.

Figure 1N:
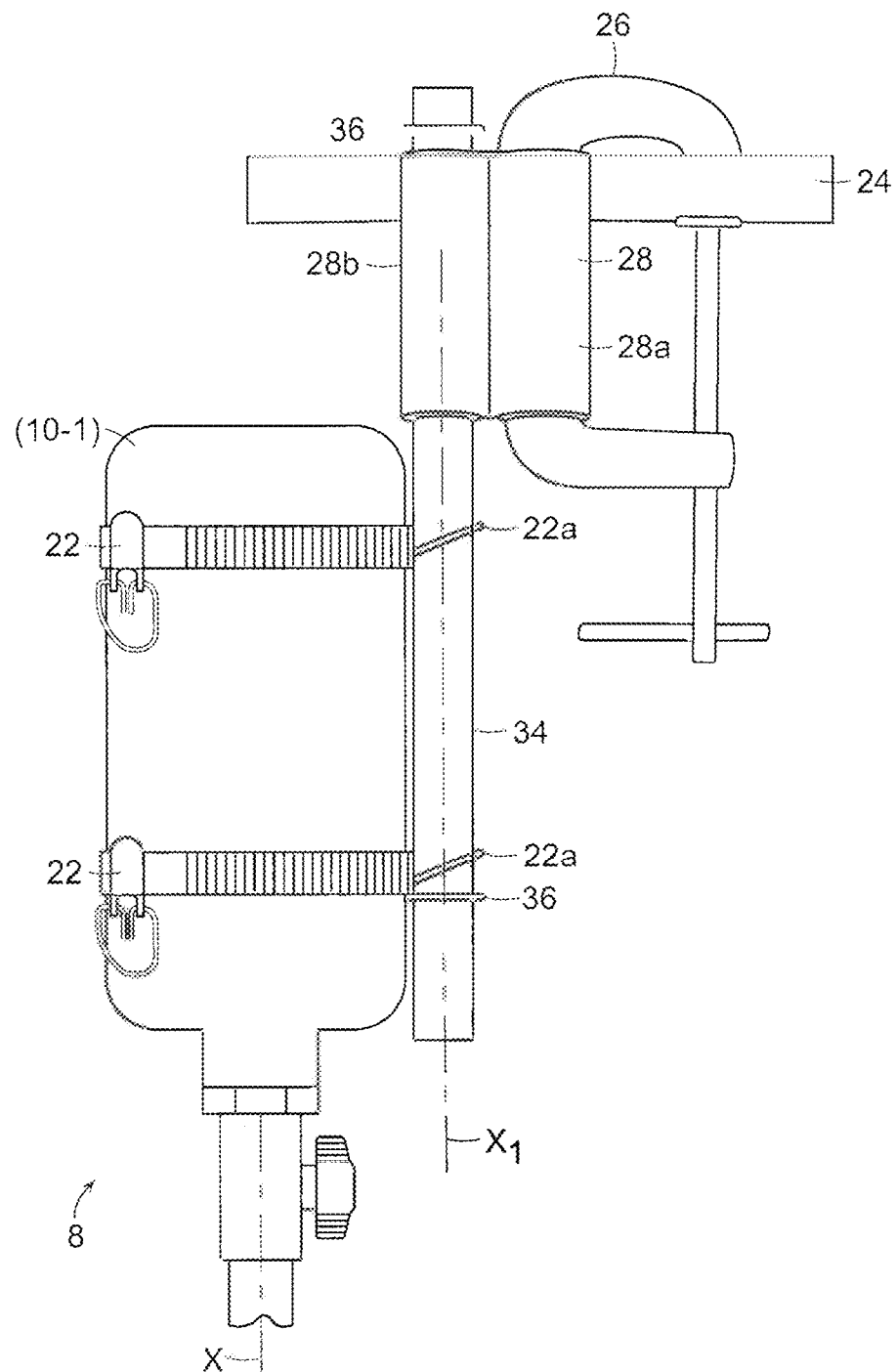
FIG. 1N is a side view showing another configuration of the securement arrangement of FIG. 1M.

Referring to FIG. 1M, separating device 8 can be mounted by a mounting device bracket or arrangement 48, for example, to a surface or rail, such as on a boat or canoe for use or testing on the water. The mounting device 48 can have a C-clamp 26 for securement to the desired surface or rail 24. A bracket body 28 can have a portion 28a secured to or around a vertical member of the C-clamp 26, and a portion 28b for rotatably or pivotably mounting a pivot rod 34 therein about a vertical axis $X_1$. The separating device 8 can have two spaced securement bands 22 around the darkened chamber (10-1) with securement fixtures 22a that secure the separating device 8 to the pivot rod 34. The pivot rod 34 can have stop members 36. The pivot rod 34 can allow the separating device 8 to be pivotably adjusted about axis $X_1$. The separating device 8 can be positioned to extend above C-clamp 26 as shown in FIG. 1M, or below as seen in FIG. 1N.

The devices, methods and kits can be used together or separately to obtain of well-separated samples of phytoplankton and/or zooplankton. One of skill in the art will recognize that modifications and adjustments to the device, kits and methods are encompassed by the scope of the invention described herein.

EXAMPLES

Devices were developed that provide the conditions necessary to initiate and direct the movement of zooplankton. Experiments were conducted in Lake Cochichewick and Willand Pond to evaluate separation efficiency for zooplankton and phytoplankton as measured by zooplankton biomass, microcystis equivalents and chlorophyll (a). The evaluation included an original design (2013) and an improved design (2014). There was no significant difference in zooplankton separation efficiencies for either lake between sampling years. Significant reduction in amount and variability of microcystis equivalents and chlorophyll(a) was observed in 2014. The methods and devices allow for the rapid collection of samples for surveillance programs and ecological risk assessments. This is part of an ongoing study to evaluate the device and method in different conditions and over seasonal cycles, and in other environments where questions regarding the presence of toxic substances and their potential for bioaccumulation exist.

Example 1

Materials and Procedures
Collection and Processing of Plankton Samples

The study sites included Lake Cochichewick in North Andover, Mass. (August-October 2013) and Willand Pond in Dover, N.H. (September-October, 2013). Lake Cochichewick is classified as a mesotrophic system and Willand Pond is classified as an oligotrophic system. Concentrated plankton samples for testing were collected from the deep sites between the hours of 10 AM-2 PM using a vertical tow by lowering a 50 nm nylon mesh 30 cm open ring conical plankton net fitted with a 50 um mesh bucket to a depth of 5 m (volume filtered=350 L) and raising vertically at a speed approximating 0.5 m/s. The total number of plankton samples collected depended upon the number of trials to be conducted that day. For example, if twelve (12) trials are conducted, twelve (12) samples are collected. The concentrated plankton samples were placed together in one (1) L. darkened HDPE bottles. Typically, eight (8) to ten (10) concentrated samples are collected in a single bottle, and two bottles of concentrate collected for testing.

Whole lake water was collected in 1 liter darkened HDPE bottles as a surface grab sample to be used as diluent for the concentrate, and as supply for filtered lake water. The concentrated samples were combined in a 5 liter container, mixed, and split using a Folsom plankton splitter until 100 ml aliquots were obtained. The whole lake water (diluent) was combined in a series of 5 liter containers and split using a Folsom plankton splitter until 850 ml aliquots were obtained. The individual concentrate portions (100 mls) were combined with the individual diluent portions (850 mls) for a total of 950 mls of plankton sample, and placed into darkened HDPE bottles. Typically 24 bottles of plankton were prepared in this manner. Filtered lake water was prepared by filtering 1 liter of whole lake water through a 50 um mesh ring net and placing it in a 1 liter beaker. Prior to use in the separation device, filtered lake water samples were analyzed following quantification.

Plankton Separation Efficiency:

Step 1. A separation device was suspended using a sling apparatus. The collection tube was closed off using the ratchet clamp, and filled with filtered lake water. The collection tube was then physically separated from the chamber with the use of a black rubber stopper attached to a plastic rod. The plankton sample was then poured into the chamber. When volume series, time series or calibration series were conducted, as many separation devices as needed were prepared in this manner concurrently. For example, when a time series for 0, 10, 20 and 30 minutes was conducted, four (4) separation devices were prepared. The rubber stopper was removed, the lid placed on top of the chamber and the timer set for the desired time interval.

Collection of Zooplankton and Phytoplankton

Step 2. At the desired time interval, the desired volume of sample was released from the collection tube by opening the ratchet clamp, dispensing the sample into an appropriate container, and then closing the ratchet clamp. This sample was marked as the "Z" (zooplankton) portion. The remainder of the sample was released from the collection tube by opening the ratchet clamp and dispensing the sample into a 1 L. carboy. This sample was marked as the "P" (phytoplankton) portion.

Quantification

Step 3. Phycocyanin (PC) and Chlorophyll (a) (Chla) for the "Z" portion and "P" portion were quantified in vivo, using intact cells without filtration or extraction, using a two-channel hand held AquaFluor fluorometer (Turner Designs, Sunnyvale, Calif.). Using a disposable pipette, 5 mls of each "Z" portion and each "P" portion was placed into a Turner Design methacrylate cuvette. Large specimens of zooplankton were removed from the cuvette using a small tipped disposable pipette prior to analysis. The filled cuvette was placed in the fluorometer and, using channel A, the relative fluorescence units for PC were recorded. Without removing the cuvette from the instrument, channel B was selected and relative fluorescence units for Chla were recorded. PC (excitation at 595 run, emission at 670 nm) was standardized ($R2=0.99$, $p<0.0000$, Microcystis equivalents (MIC eq.)=1369 (x)+4245) using *M. aeruginosa* 2385. Chlorophyll a (excitation at 460 nm, emission >665 nm) was standardized ($R2=0.99$, $p<0.000$, Chla=8624 (x)-120812) with solid secondary standard (No. 8000-952, Turner Designs). The PC and Chla value of the "Z" portion was adjusted (Adj. Z) to account for the background in the filtered water. The MIC (eq.) and Chl(a) concentration/ml were adjusted to reflect volumes collected. The proportion of MIC (eq.) or Chl(a) (separation efficiency) in the "Z" portion for each sample was calculated as follows:

$$(Adj.\ Mic.\ eq.\ "Z")/(Adj.\ Mic.\ eq.\ "Z")+(Mic.\ eq.\ "P")$$

=Separation efficiency for Cyanobacteria     Eq. 1

$$(Adj.\ Chl(a)"Z")/(Adj.\ Chl(a)"Z")+(Chl(a)"P")$$

=Separation efficiency for phytoplankton     Eq. 2

Step 4. The "Z" portion was preserved using 5% formalin/sucrose. See Haney, J. F. & D. J. Hall, 1973, "Sugar coated *Daphnia*: A preservation technique for Cladocera," *Limnol. Oceanogr.* 16: 970-977. The "P" portion was filtered through a 50 um mesh ring net, backwashed and brought to an appropriate volume using filtered lake water, and preserved using 5% formalin/sucrose.

Identification and Counting

Step 5. Zooplankton in each "Z" and "P" sample were identified, enumerated and measured. A minimum of 200 individuals were counted in a known subsample volume. The body length (and width as needed) of the first 20 individuals encountered for each genus and/or species was measured. If needed, the count data of the "P" portion was adjusted (Adj. P) to reflect the proportions of sample removed above to quantify phycocyanin and Chlorophyll (a). The count data for the "Z" and "P" portion were adjusted to reflect total sample volume. Dry weight estimates for *Daphnia* spp. *Diaphanosoma* spp., Copepods and *Bosmina* spp. were calculated according to Bottrell, H.H., A. Duncan, Z. M. Gliwicz, E. Grygierek, A. Herzig, A Hillbricht-Ilkowska, H. Kurosawa, P. Larsson, and T. Weglenska, 1976, "A review of some problems in zooplankton production studies," *Norw. J. Zool.*, 24:419-456, *Chydorus* spp. was calculated according to Dumont, H. J., I. van de Velde, and Dumont, S., 1975, "The dry weight estimate of biomass in a selection of Cladocera, Copepoda and Rotifera from the plankton, periphyton and benthos of continental waters," *Oecologia*, 19:75-97. Rotifers were calculated according to EPA Great Lakes National Program Office, 2003, "Standard operating procedure for zooplankton analysis," *LG*403, Revision 3 Feb. 2003, and nauplii were assigned a constant dry weight of 0.40 ug. The proportion of zooplankton biomass (separation efficiency) in the "Z" portion for each sample was calculated as follows:

$$(Dry\ wt.\ "Z")/(Dry\ wt.\ "Z")+(Dry\ wt.\ (Adj.)"P")$$

=Biomass separation efficiency for zooplankton     Eq. 3

The proportionate values were arcsine transformed (Zar, Jerrold H., *Biostatistical Analysis*, Prentice-Hall, Inc. New Jersey, 1974 ed.) and appropriate statistical analysis performed.

Assessment:

The desired volume of the darkened chamber was one (1) liter. The physical requirements of the collection tube (transparent, preferably conical and allowing migrating animals to exceed 48° to the normal) suggested a long, narrow tube or tubing. A tube which measured 1"(D)×8"(L), had a maximum volume of 75 mls, and exceeded the 48° angular criteria at a volume of approximately 50 mls was used. In this embodiment, a stopper was used to provide a temporary physical separation between the chamber and the collection tube. The separation time and volume of the zooplankton and/or phytoplankton samples to be collected were undetermined. Experiments were designed to evaluate the device performance for separation of zooplankton with samples from Lake Cochichewick (August 1) using the methods described in Steps 1-2 and Steps 4-5.

First Experiment

The first experiment (August 1) was designed to evaluate separation efficiencies for zooplankton using the methods described in Steps 1-2 and 4-5.

Figure 2:
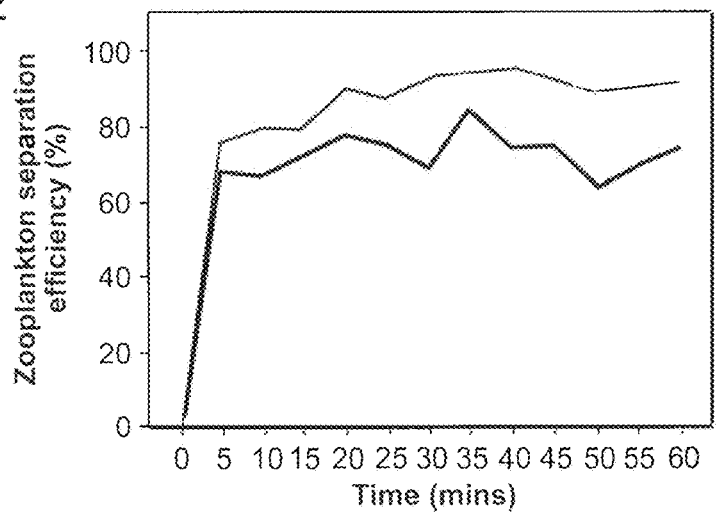
FIG. 2 is a plot showing the separation efficiency for macrozooplankton (top line) and microzooplankton (bottom line) on Aug. 1, 2013 (Experiment 1) "Z"=zooplankton, 50 mls., "P"=phytoplankton, 900 mls.

The results in FIG. 2 indicate that the greatest separation efficiency occurred at T=40 minutes for macrozooplankton and microzooplankton. Separation efficiencies greater than 90% occurred at T=20 minutes for macrozooplankton.

Second Experiment

Figure 3A:
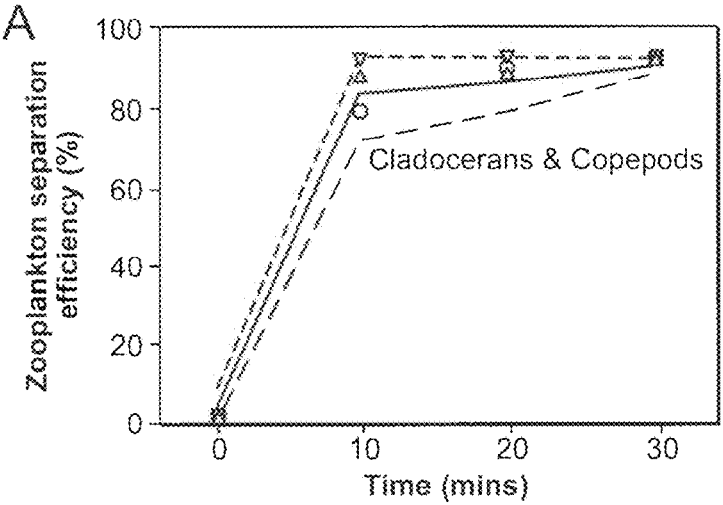
FIG. 3A and FIG. 3B are plots showing mean separation efficiencies for macrozooplankton and microzooplankton in Lake Cochichewick (A) and Willand Pond (B) on Sep. 4 and Sep. 5, 2013, respectively.
Figure 3B:
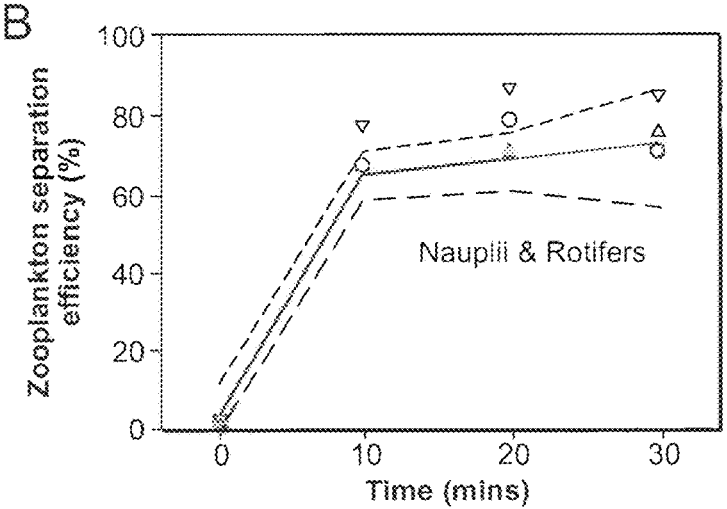

The experimental design was modified to evaluate separation efficiencies using the methods described in Steps 1-5. Additional experiments were conducted using samples from Lake Cochichewick (September 4) and Willand Pond (September 5) with the results shown in FIG. 3A and FIG. 3B. The macrozooplankton consistently had the highest mean separation efficiency for both lakes. The macrozooplankton comprised 89% of the biomass in Lake Cochichewick and 71% of the biomass in Willand Pond.

Figure 4A:
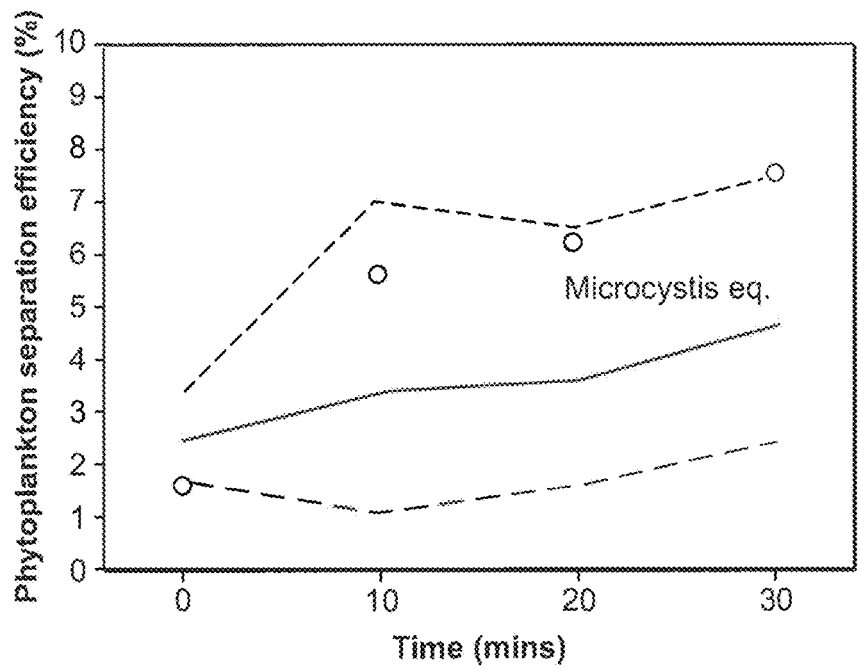
FIG. 4A and FIG. 4B are plots showing calibration curves for macrozooplankton (solid line), Cyanobacteria (dashed line), and all phytoplankton (dotted line) for Lake Cochichewick (A) and Willand Pond (B) on Sep. 4 and Sep. 5, 2013, respectively. Confidence intervals (95%) shown as gray lines. Df=4. "Z"=zooplankton, 50 mls, "P"=phytoplankton, 900 mls.
Figure 4B:
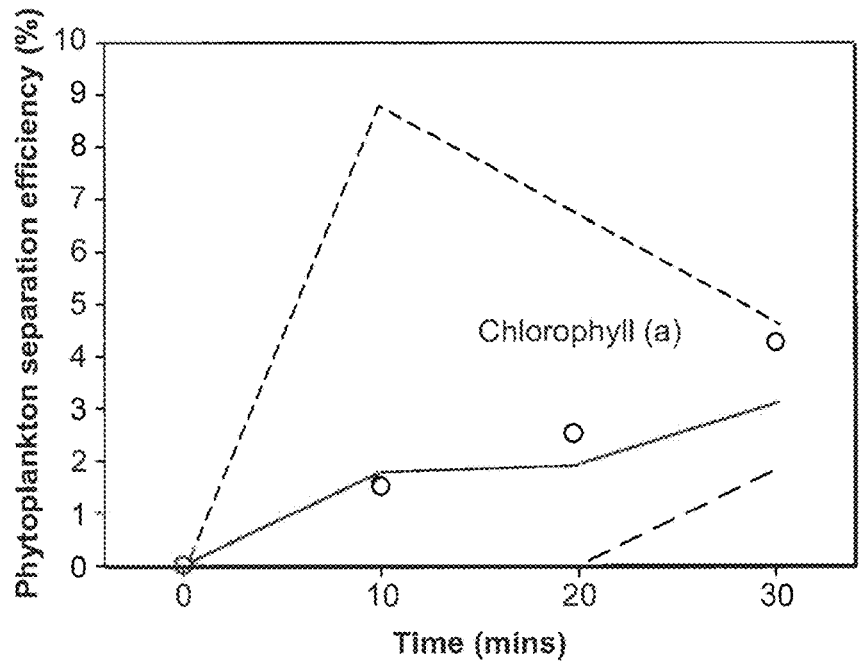

FIG. 4A and FIG. 4B are plots showing calibration curve for macrozooplankton (solid line), Cyanobacteria (dashed line), and all phytoplankton (dotted line) for Lake Cochichewick (A) and Willand Pond (B) on Sep. 4 and Sep. 5, 2013, respectively. Confidence intervals are shown in gray.

Figure 5A:
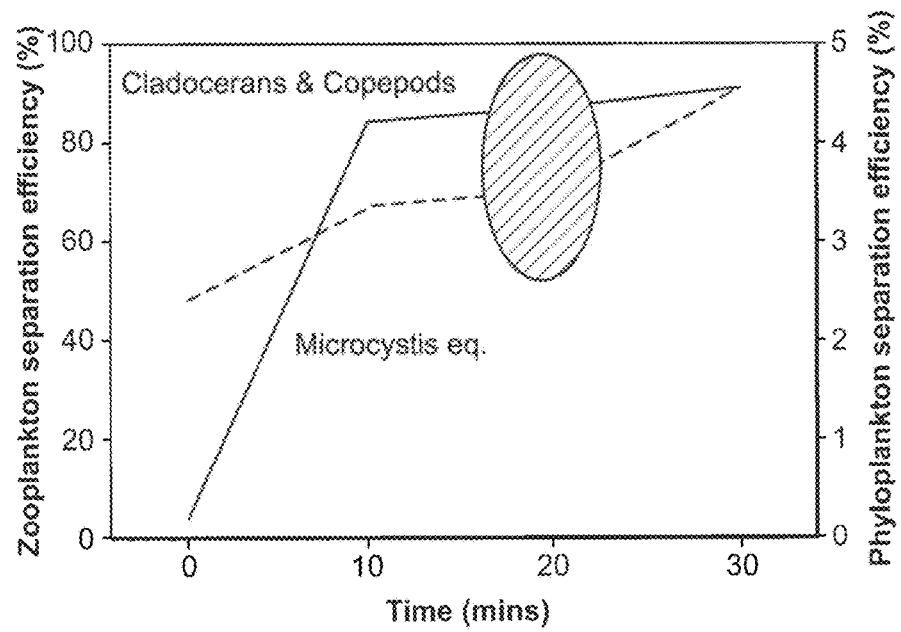
FIG. 5A and FIG. 5B are plots showing calibration curves for macrozooplankton (solid line) and Cyanobacteria (dashed line) for Lake Cochichewick (A) and Willand Pond (B) compared with data from Oct. 10 and Oct. 16, 2013, respectively.
Figure 5B:
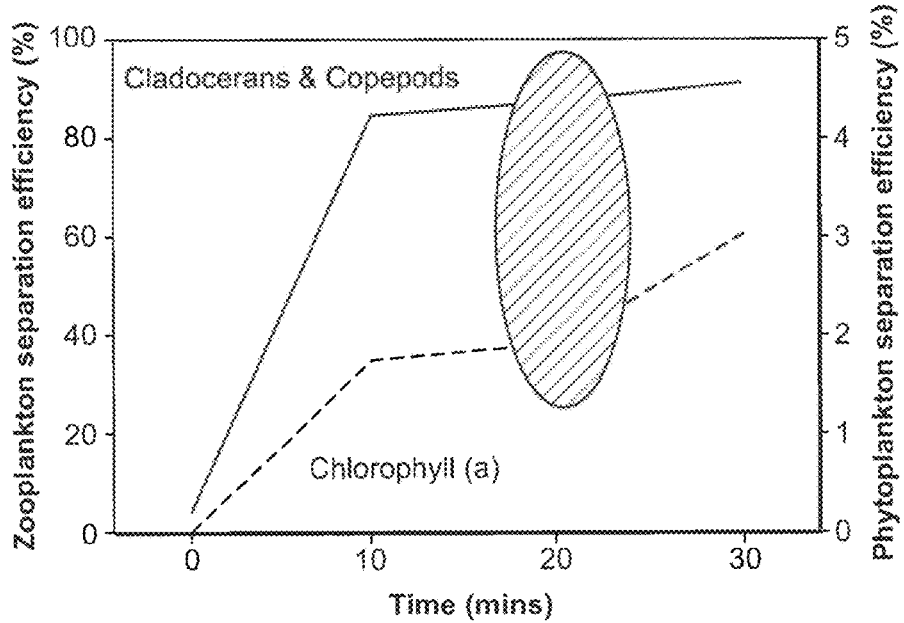
Figure 6:
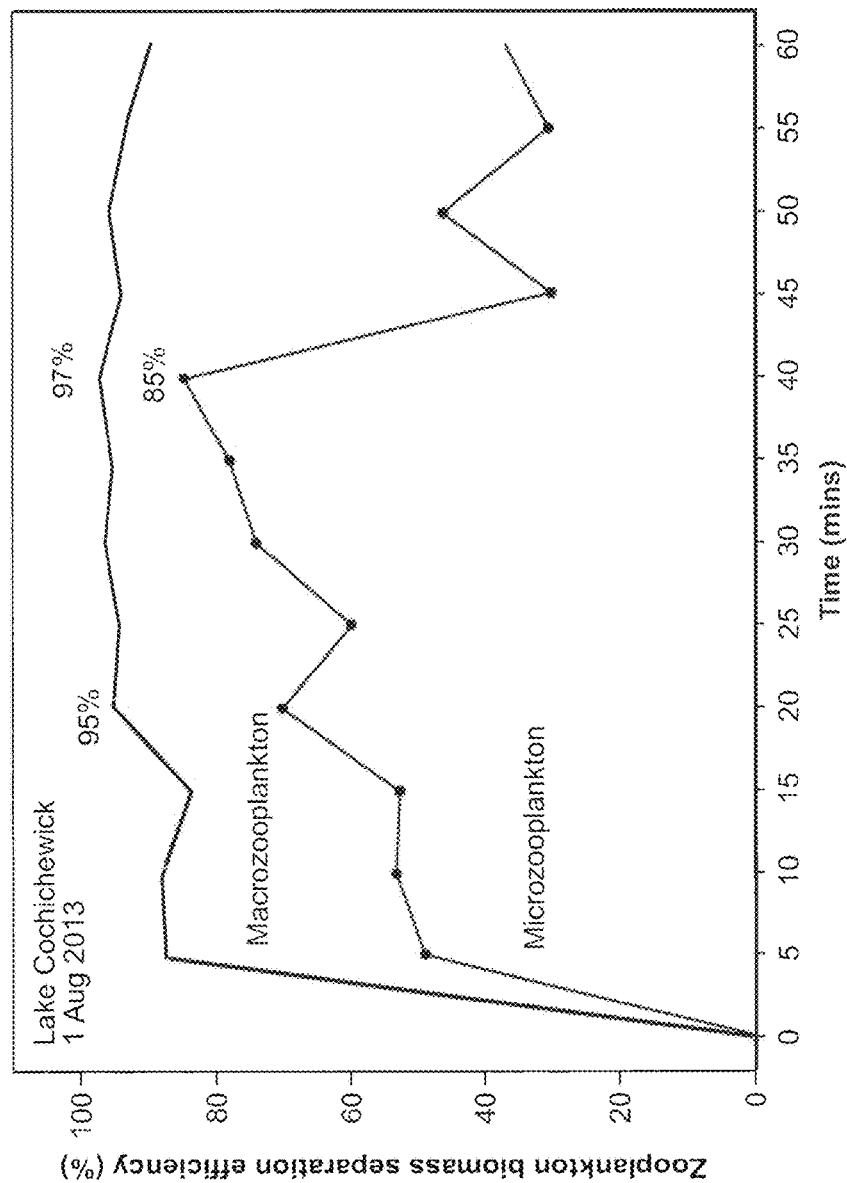
FIG. 6 is a graph showing separation efficiency curves for Lake Cochichewick on Aug. 1, 2013. Macrozooplankton (solid line) and microzooplankton (solid gray line). Z"=50 mls, "P"=950 mls.

FIG. 5A and FIG. 5B compare the September calibration curves with data from samples taken in October for Lake Cochichewick (FIG. 5A) and Willand Pond (FIG. 5B). The macrozooplankton comprised 93% of the biomass in Lake Cochichewick and 91% of the biomass in Willand Pond.

The calibration curves suggest that the researcher could select a variety of times to allow for the separation of the zooplankton and the phytoplankton depending on project objectives. For this study, the objective was to collect a known volume at a specific time that would contain the greatest biomass of macrozooplankton with the least biomass of Cyanobacteria. FIGS. 4A and 4B suggest that, in this context, the researcher should wait 30 minutes before the collection of a 50 ml zooplankton sample, and then collect the remaining 900 mls for a Cyanobacterial sample.

Discussion

The results from this study suggest that a rapid method can be used in the field to separate plankton into the component parts. The data suggest that similar results may be obtained when the researcher follows the standard operating procedure and uses a device having design elements sufficient to facilitate a positive phototactic response.

Ambient light was used to simulate the spectral distribution of irradiance in the natural system. Filtered lake water was used to address issues related to dissolved substances and the response of the zooplankton to rapid changes in water temperature.

The design of the separation device with the completely darkened chamber and a transparent collection tube located at a 90 degree vertical position allows for direct illumination which has an angular distribution that approximates 0 (zero).

The design of the separation device with a completely darkened chamber and transparent collection tube provides the conditions to initiate a positive phototactic response to a sudden change in light intensity (Buchanan, C. B. Goldberg and R. McCartney 1982, "A laboratory method for studying zooplankton swimming behaviors," Hydrobiologic 94, 77-89). Although measurements of the light intensity were not taken during these experiments, it was assumed that the light intensity exceeds the threshold for instantaneous relative change in light intensity of 0.2 uE m-2 s-1 (the rheobase) necessary for photobehavior to occur. The orientation of the device (darkened above, light below) serves to facilitate and reinforce body axis orientation which results from a response to the spatial change in light intensity (light/dark boundaries, contrast and shadows). *Daphnia magna* have been shown to orient their movements away from overhead shadows as a flight response from predators.

The length of the separation device and the volume of the zooplankton sample to be collected are determined for migration potential and contrast orientation. By creating a sudden stimulus of dark to light to maximize migration rates, the maximum migration distance of 42 cm was achieved within a specified time. Additionally, by leveraging the influence of contrast orientation by driving the zooplankton past the angle of 48° to the normal, optimal conditions were achieved. The optimum volume to be collected using this collection tube was determined to be 50 mls.

In addition to facilitating migration and contrast orientation, the incidental collection of phytoplankton in the zooplankton sample and the zooplankton in the phytoplankton was considered. Optimizing the separation and collection for each portion of the plankton was achieved. Separation efficiency using a method collecting a 50 ml sample versus an alternative method collecting a 250 ml sample demonstrated the superior quality of the samples obtained using the method described herein.

In spite of achieving separation efficiencies that exceeded our expectations, it is still necessary to account for the variability we observed. In regard to the zooplankton, it is possible that the composition and distribution of the biomass had an influence on the separation efficiencies that was observed. It is also possible that lake trophic status exerts a significant influence on separation efficiency. We remain somewhat puzzled at the level of incidental capture of the phytoplankton, specifically the Cyanobacteria, in the zooplankton samples and the variability of the results. The calibration curves suggest that after 30 minutes, the levels obtained would be no different than levels obtained from a completely mixed sample. It is unknown whether the incidental capture is from a process of sinking or the combined influence of entrainment and convectional streaming. Since Cyanobacteria typically contain gas vacuoles, the phenomenon of sinking does not appear to be the answer.

Example 2

In further examples, data is presented from two separation devices.

Prototype #1 Design elements: The device contained design elements as shown in FIG. 1A. The darkened chamber was smooth walled and conical in shape, with a volume of 1 L. The chamber was constructed to prevent light from entering the chamber during the separation phase (tight fitting lid as needed). There was a temporary darkened physical separation between the chamber and collection tube with a diameter of approximately 21.5 mm. This diameter was large enough to allow for a narrow stimulus beam of light to be refracted at an angle approximating 45° (or less) to the vertical plane and to meet the spatial needs of the migrating zooplankton. A stopper was used to provide a temporary physical separation between the chamber and the collection tube. The transparent collection tube allowed for the maximum amount of illumination and was conical in shape to facilitate the collection of zooplankton. The length of the collection tube was such that the zooplankton could migrate past a 45° angle to the vertical plane within the tube. A tube was used with maximum diameter (21.5 mm), minimum diameter (5 mm), length of 150 mm and a maximum volume of 75 mls with rubber tubing (diameter 7 mm) and a clamp. External support to the device was provided via external rings and a sling device.

Prototype #2 design elements: The device contained design elements as shown in FIG. 1D. The design was modified to reduce the variability in separation efficiency and to simplify sample handling. It was assumed there was potential for leakage around the rubber stopper and mixing during its removal, thereby increasing the amount of phytoplankton found in the zooplankton sample. To improve the design, an adapter with a minimum diameter of 20 mm was used as the temporary darkened physical separation. This was a diameter sufficient to allow for a narrow stimulus beam of light to be refracted at an angle approximating 45° (or less) to the vertical plane and to meet the spatial needs of the migrating zooplankton. The conical collection tube, rubber tubing and clamp was replaced with a cylindrical collection cartridge (25 mm diameter) that would continue to meet the spatial needs of the migrating zooplankton and simplify sample handling. Rings were added to provide options for external support.

Collection and processing of plankton samples: The two study sites included Lake Cochichewick in North Andover, Mass., USA (42° 19.7'N: 71° 54.9'W) and Willand Pond in Dover, N.H., USA (43° 43.2'N: 70° 29.6'W). Lake Cochichewick is classified as a mesotrophic system and Willand Pond is classified as an oligotrophic system (Carlson, 1977). The deep sites were accessed by kayak. Concentrated plankton samples were collected between the hours of 10 AM-2 PM using a vertical tow by lowering a 50 um nylon mesh 30 cm open ring conical plankton net fitted with a 50 um mesh bucket to a depth of 5 m (total volume filtered=350 L) and raising vertically at a speed approximating 0.5 m/s. The total number of samples collected depended upon the number of trials to be conducted that day. For example, if 12 trials were to be conducted, 12 samples would be collected. The concentrated plankton samples were placed together in 1 L darkened HDPE (high density polyethylene) bottles. Typically 8-10 concentrated samples would be collected in a single bottle, and 2 bottles of concentrate collected for testing. Whole lake water was collected in 1 L darkened HDPE bottles as a surface grab sample to be used as diluent for the concentrate and as a supply for filtered lake water. The concentrated samples were combined in a 5 L container, mixed, and split using a Folsom plankton splitter until 100 ml aliquots were obtained. The whole lake water (diluent) was combined in a series of 5 L containers and split using a Folsom plankton splitter until 900 ml aliquots were obtained. The individual concentrate portions (100 mls)

were combined with the individual diluent portions (900 mls) for a total of 1 L of plankton sample, and placed into 1 L darkened HDPE bottles. Typically, 24 bottles of plankton were prepared in this manner. Filtered lake water was prepared by filtering 1 L of whole lake water through a 50 um mesh ring net and placing it in a 1 L beaker. Prior to use in the separation device, filtered lake water samples were analyzed following Step 3 below.

Plankton Separation—Step 1.

Protoype #1. The separation device was suspended using a sling apparatus. The collection tube was closed off using the ratchet clamp, and filled with filtered lake water. The collection tube was physically separated from the chamber with the use of a black rubber stopper attached to a plastic rod. The plankton sample was poured into the chamber. The rubber stopper was removed, the lid placed on top of the chamber and the timer set for the desired time interval. When volume series, time series or calibration series were conducted, as many separation devices as needed were prepared in this manner concurrently. For example, when a time series for 0, 10, 20 and 30 minutes was conducted, 4 separation devices were prepared.

Prototype #2: The collection cartridge was attached to the end of the adapter, filled with filtered lake water and then closed. The plankton sample was placed into the chamber. The adapter/collection tube was screwed onto the chamber, which was then suspended with a sling. The adapter was opened and the timer set for the desired time interval.

Plankton Separation—Step 2.

Prototype #1. At the desired time interval, the desired volume of sample was released from the collection tube by opening the ratchet clamp, dispensing the sample into a 100 ml sample jar, and then closing the ratchet clamp. This sample was marked as the "Z" (zooplankton) portion. The remainder of the sample was released from the collection tube by opening the ratchet clamp and dispensing the sample into a 1 L carboy. This sample was marked as the "P" (phytoplankton) portion Prototype #2. At the desired time interval, the adapter was closed and the collection cartridge removed from the bottom of the adapter. The sample was dispensed into a 100 ml sample jar and marked as the "Z" (zooplankton) portion. The chamber was then inverted and the adapter removed. This sample was marked as the "P" (phytoplankton) portion.

Plankton Separation—Step 3.

Phycocyanin (PC) and Chlorophyll (a) (Chla) for the "Z" portion and "P" portion were quantified using a two-channel hand held AquaFluor fluorometer (Turner Designs). Using a disposable pipette 5 mls of each "Z" portion and "P" portion was placed into a 5 ml vial, frozen and then thawed. The thawed sample was placed into a methacrylate cuvette. The filled cuvette was placed in the fluorometer and using channel A, the relative fluorescence units for PC were recorded. Without removing the cuvette from the instrument, channel B was selected and relative fluorescence units for Chla were recorded. PC (excitation at 595 nm, emission at 670 nm) was standardized ($R^2$=0.99, p<0.0000, Microcystis equivalents (MIC eq.)=1369 (x)+4245) using *M. aeruginosa* 2385. Chla (excitation at 460 nm, emission >665 nm) was standardized ($R^2$=0.99, p<0.000, Chla=8624 (x)-120812) with solid secondary standard (No. 8000-952, Turner Designs). The PC and Chla value of the "Z" portion was adjusted (Adj. Z) to account for the background in the filtered water. The MIC eq. and Chla concentrations/ml were adjusted to reflect the volumes collected. The proportion of MIC eq. or Chla (separation efficiency) in the "Z" portion for each sample was calculated as follows:

$$\text{Adj. MIC eq. "Z"/Adj. MIC eq. "Z"+MIC eq.} \text{ "P"=Separation efficiency for Cyanobacteria} \quad (1)$$

$$\text{Adj. Chla "Z"/Adj. Chla "Z"+Chla "P"=Separation efficiency for phytoplankton} \quad (2)$$

Plankton Separation—Step 4.

The remaining "Z" portion was preserved using 5% formalin/sucrose (Haney & Hall, 1973). The remaining "P" portion was filtered through a 50 um mesh ring net, backwashed with a wash bottle filled with filtered lake water, brought to an appropriate volume using filtered lake water, and preserved using 5% formalin/sucrose.

Plankton Separation—Step 5.

Zooplankton in each "Z" and "P" sample were identified, enumerated and measured using an Amscope T370B-9M compound microscope, a 9.1 megapixel USB 2.0 digital camera, Amscope Version 3.7 digital imaging software and an IBM Think pad. A minimum of 200 individuals were counted in a known subsample volume. The body length (and width as needed) of the first 20 individuals for each genus and/or species was measured. If needed, the count data of the "P" portion was adjusted (Adj. P) to reflect the proportions of sample removed in Step 3 to quantify phycocyanin and Chlorophyll (a). The count data for the "Z" and "P" portion were adjusted to reflect the total sample volume. Dry weight estimates of biomass for cladocerans (*Daphnia* spp., *Diaphanosoma* and *Bosmina*) and copepods and were calculated according to Bottrell (1976). Dry weight estimates of biomass for the cladoceran *Chydorus sphericus*. was calculated according to Dumont (1975). All nauplii were assigned a constant dry weight of 0.40 ug. Dry weight estimates of biomass for rotifers were calculated according to EPA (2003). Values recorded included "Macrozooplankton" and "Microzooplankton". Zooplankton included as "Macrozooplankton" considered the findings of Lampert, W. and B. E. Taylor, 1985, "Zoooplankton grazing in a eutrophic lake: Implication of vertical migration," *Ecology* 66:68-92, Lampert, W., W. Fleckner, H. Rai and B. E. Taylor, 1986, "Phytoplankton control by grazing zooplankton: A study on the spring clear-water phase," *Limnol. Oceanogr.* 31(3): 478-490, Watras, C. J. and N. Bloom, 1992, "Mercury and methylmercury in individual zooplankton: Implications for bioaccumulation," *Limnol. Oceanogr.*, 37(6):1313-1318, and Back, R. C., V. Visman, and C. J. Watras, 1995, "Microhomogenization of individual zooplankton species improves mercury and methylmercury determinations," *Can. J. Fish. Aquat. Sci.*, 52: 2470-2475 and included any genus and/or species which comprised greater than 1.0% of the total biomass of the sample.

The zooplankton biomass separation efficiency for each sample was calculated as follows:

$$\text{Dry wt."Z"/Dry wt."Z"+Dry wt.} \text{Adj."P"=Zooplankton biomass separation efficiency} \quad (3)$$

All proportionate values were arcsine transformed (Zar, Jerrold H., "Biostatistical Analysis," Prentice-Hall, Inc. New Jersey. 1974 ed.). Studentized T-tests and analysis of variance (ANOVA) were conducted using SigmaPlot V. 12.5.

Assessment

An experiment in Lake Cochichewick (1 Aug. 2013) using prototype #1 was designed to evaluate separation efficiencies for zooplankton using the methods described in Steps 1-2 and Steps 4-5. Separation efficiency curves as shown in FIG. 2 indicate that the maximum separation efficiency occurred at T=40 minutes for Macrozooplankton (97%) and Microzooplankton (85%). Separation efficiencies greater than 90% occurred at T=20 minutes for Macrozooplankton (95%).

Figure 7A:
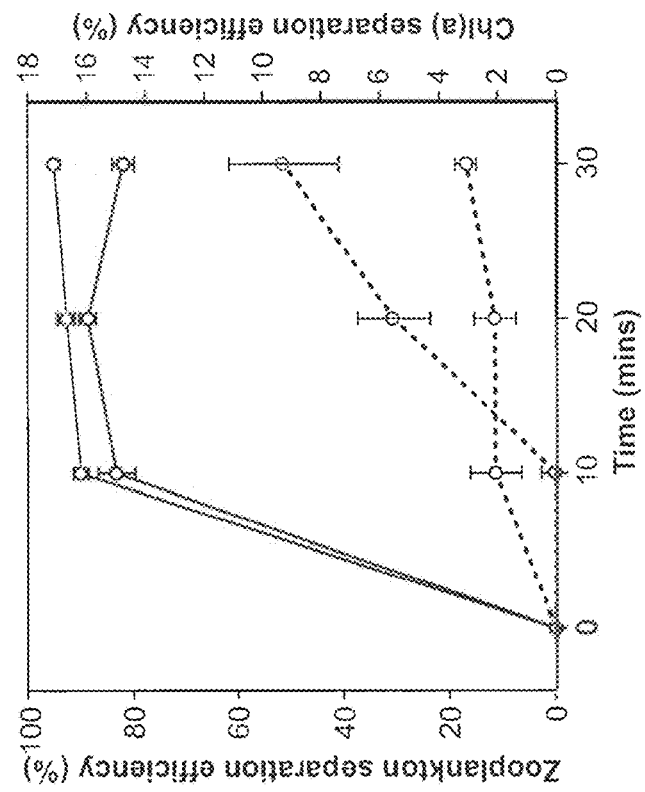
FIGS. 7A and 7B are graphs showing separation efficiency curves for macrozooplankton biomass versus microcystis equivalents and chlorophyll in Lake Cochichewick on Sep. 4, 2013 and Oct. 10, 2013.
Figure 7B:
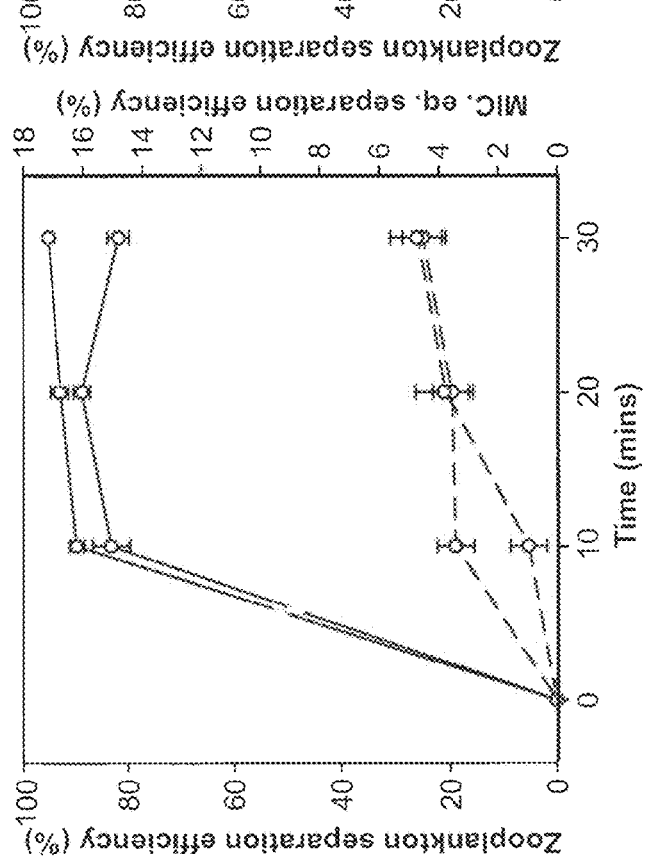

The experimental design was modified to evaluate separation efficiencies for zooplankton and phytoplankton using the methods described in Steps 1-5. This would allow determination of the optimal separation time that would provide samples with the greatest amount of zooplankton biomass (with minimal phytoplankton) and phytoplankton biomass (with minimal zooplankton). Experiments were conducted using samples from Lake Cochichewick (4 Sep. 2013, 10 Oct. 2013) and Willand Pond (5 Sep. 2013, 16 Oct. 2013). FIGS. 7A and 7B show the separations for macrozooplankton, microcystis equivalents and chlorophyll(a) for Lake Cochichewick. The mean values for macrozooplankton ranged between 90-95% (September) and 82-89% (October). The mean values for microcystis equivalents ranged between 3-5% (September) and 1-5% (October), while the chlorophyll(a) values ranged from 2-3% (September) and 6-9% (October). The macrozooplankton found in Lake Cochichewick in September and October included *Diaphanosoma brachyurum*, *Diaptomus* spp. and *Microcyclops rubellus*. FIGS. 7C and 7D show the separations for macrozooplankton, microcystis equivalents and chlorophyll(a) for Willand Pond. The mean values for macrozooplankton ranged between 81-89% (September) and 79-84% (October). The mean values for microcystis equivalents ranged between 3-8% (September) and 5-14% (October), while the chlorophyll(a) values ranged from 3-11% (September) and 6-17% (October). The macrozooplankton found in Willand Pond in September and October included *Daphnia ambigua*, *Daphnia catawba*, *Diaptomus* spp. and *Mesocyclops* edax.

The experiments were repeated for Lake Cochichewick (29 Oct. 2014) and Willand Pond (6 Sep. 2014) using prototype #2. FIGS. 8A, 8B, 8C and 8D offer a comparison of the 2013 and 2014 experiments. In Lake Cochichewick, separation efficiencies for macrozooplankton (78-89%), microcystis equivalents (4-5%) and chlorophyll(a) (4%) were observed. In Willand Pond, separation efficiencies for macrozooplankton (69-83%), microcystis equivalents (4-6%) and chlorophyll(a) (3%) were observed. Two additional macrozooplankton were found in Lake Cochichewick in 2014, including *Daphnia ambigua* and *Daphnia mendotae*, while the macrozooplankton found in Willand Pond remained unchanged. The experiments confirmed that objectives have been met to reduce the variability in separation efficiency with an improved design of the device. Analysis of variance revealed that the zooplankton separation efficiencies were not significantly different from 2013 to 2014 for either lake. In Lake Cochichewick, the amount of chlorophyll(a) was significantly reduced at T=20 minutes (p=0.024) and T=30 minutes (p=0.049). In Willand Pond, the amount of microcystis equivalents was significantly reduced at T=30 minutes (p=0.018) and the amount of chlorophyll(a) was significantly reduced at T=20 minutes (p=0.009). The reduction in the variability of the data was evidenced by the decrease in the standard deviation for the microcystis equivalents and chlorophyll(a) values from 2013 to 2014.

Figure 9:
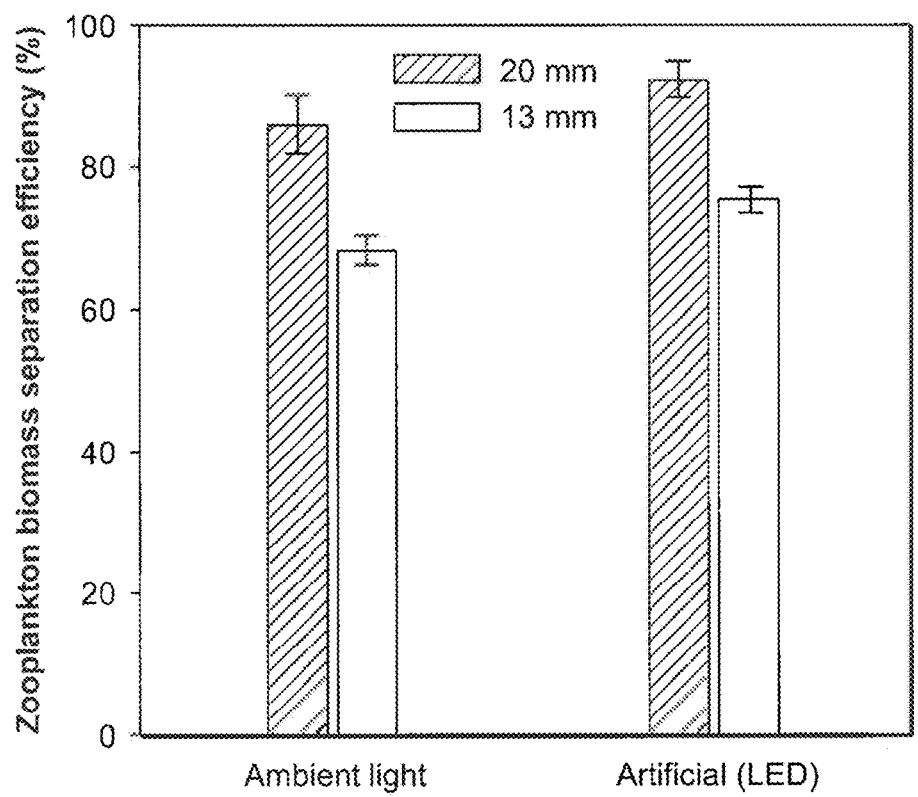
FIG. 9 is a graph depicting effect of minimum adapter diameter on separation efficiency. Macrozooplankton in Lake Cochichewick 29 Oct. 2014 with standard errors for each shown. Ambient (t-3.54, df-4, p-0.024), Artificial (t-4.90, df-4, p-0.008).

FIG. 9 provides evidence as to the importance of the spatial needs of the migrating zooplankton. This experiment evaluated the effect of the minimum diameter of the adapter that provided the temporary darkened physical separation. The experiments were conducted with ambient and artificial light, as well as adapters with minimum diameters of 20 mm and 13 mm. During the experiments with the 20 mm adapter, it was noted that the animals migrated freely, appearing in the collection cartridge within a minute of opening the ball valve. However, when the 13 mm adapter was used, 2 of the 3 collection cartridges did not have any zooplankton in them after as many as 5 minutes. The cartridges needed to be gently tapped to release the animals that were apparently clogging the opening. T-tests revealed that there was no significant difference in separation efficiency when using ambient light or artificial (LED) light for either the 20 mm or 13 mm adapter. However, the separation efficiency for the 20 mm adapter was significantly higher than the 13 mm adapter under ambient (t=3.54, df=4, p=0.024) and artificial (t=4.90, df=4, p=0.008) illumination.

Figure 10:
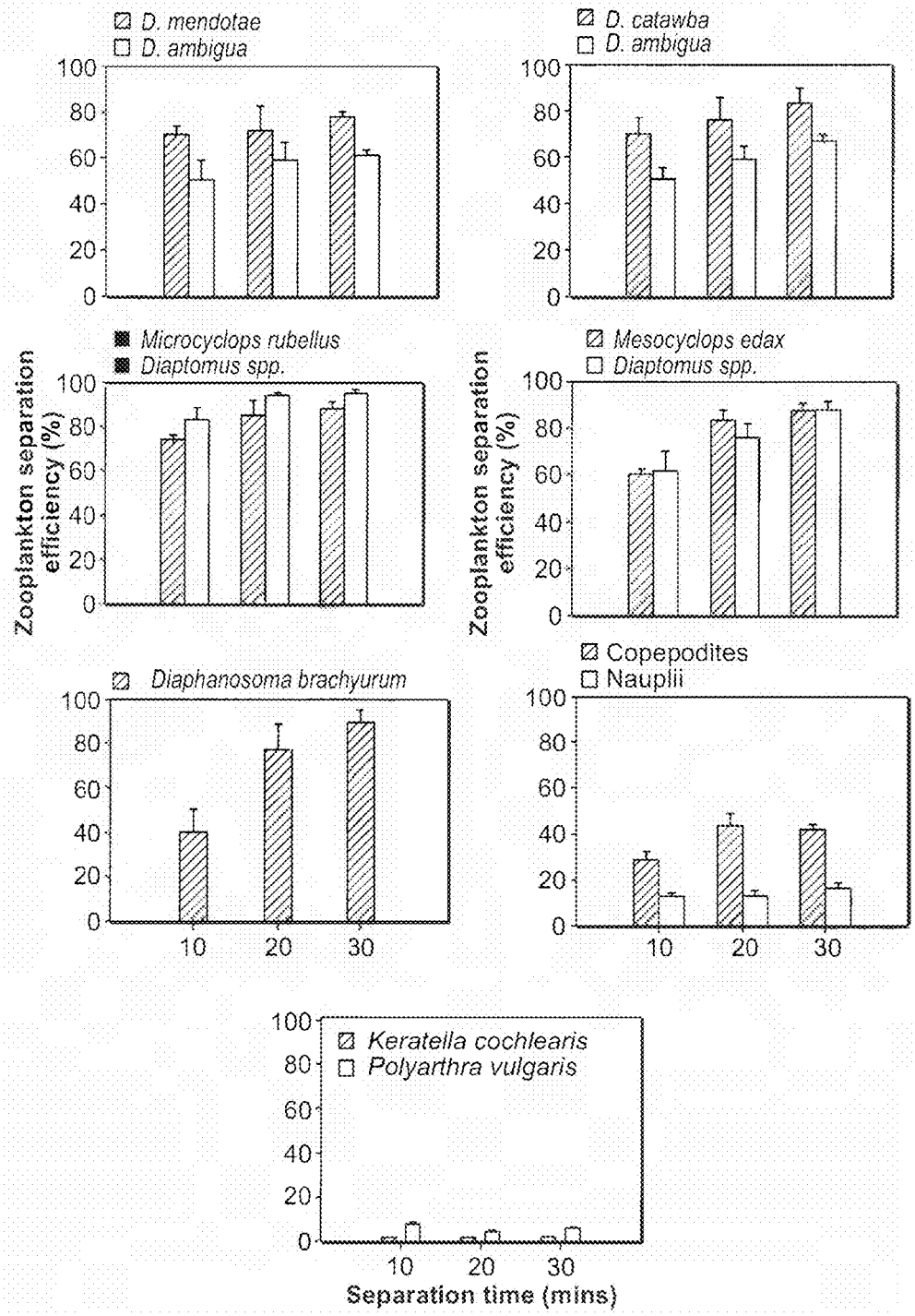
FIG. 10 are graphs showing separation efficiencies for individual zooplankters from Lake Cochichewick on Oct. 29, 2014 and Willand Pond on Sep. 6, 2014.
Figure 13:
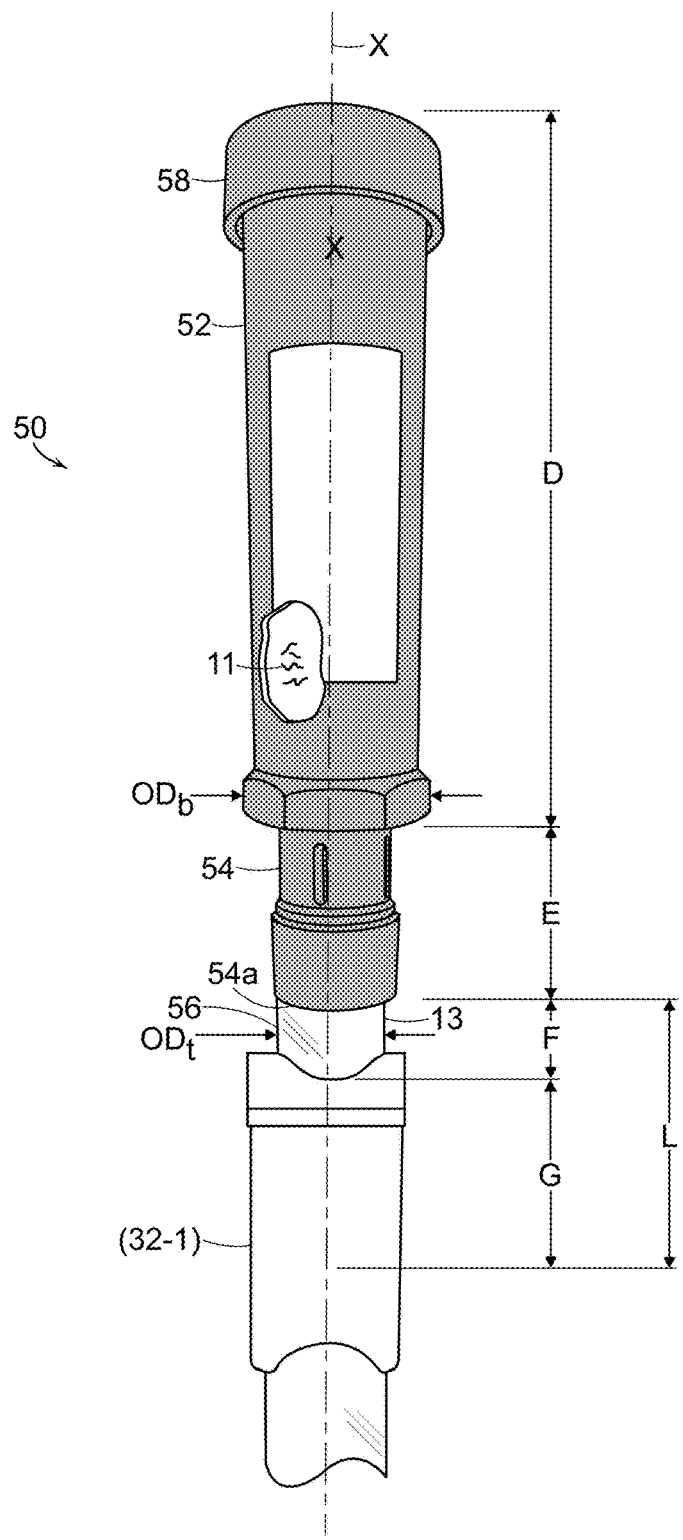
FIG. 13 is a front view of another embodiment of a plankton separation device in the present invention.
Figure 14:
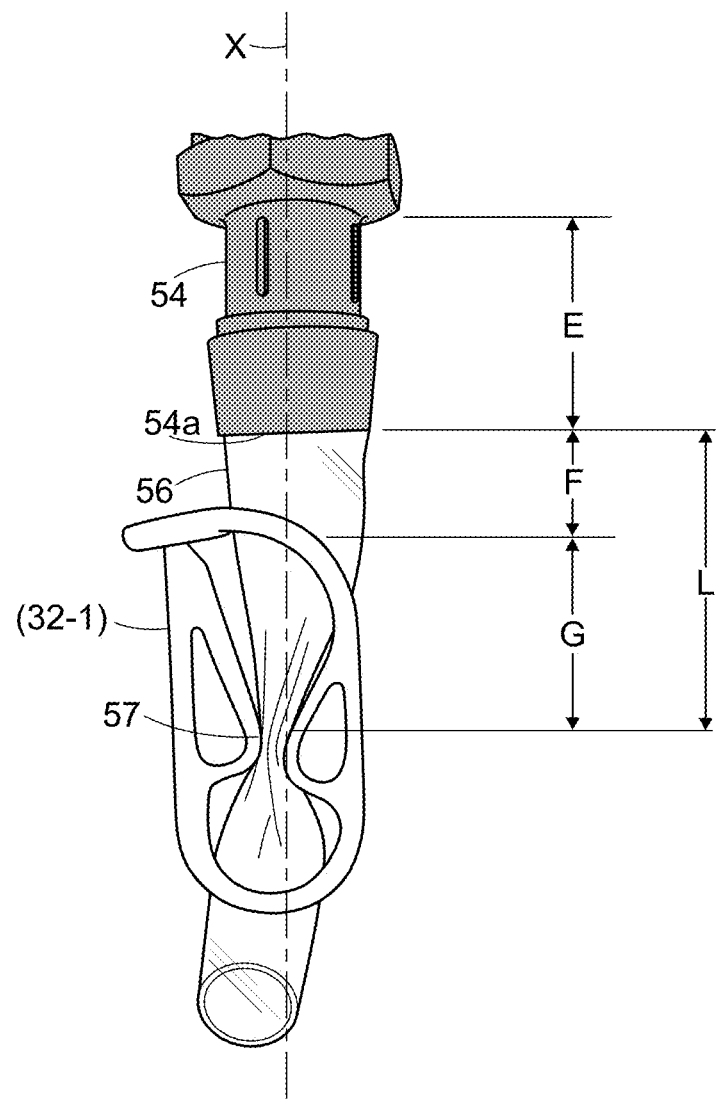
FIG. 14 is a side view of a lower portion of the plankton separation device thereof.
Figure 15:
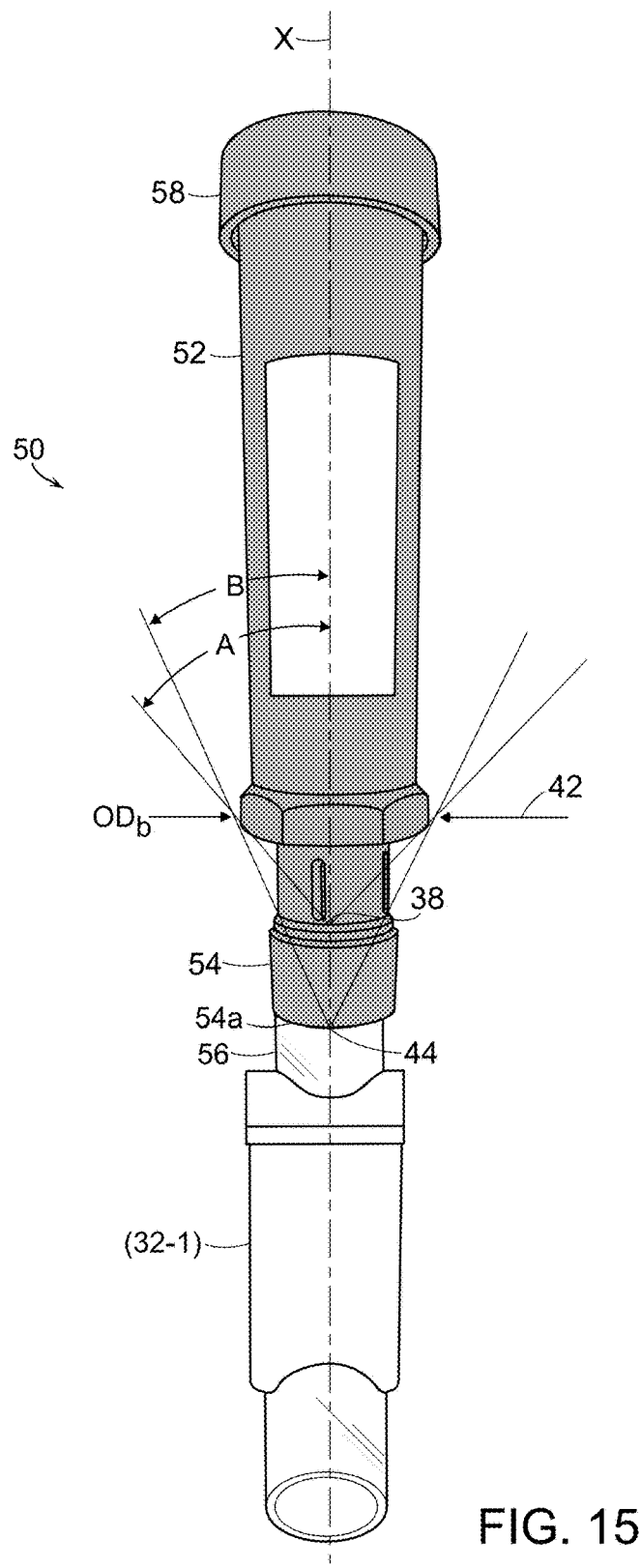
FIG. 15 is another front view thereof with additional annotation.
Figure 16:
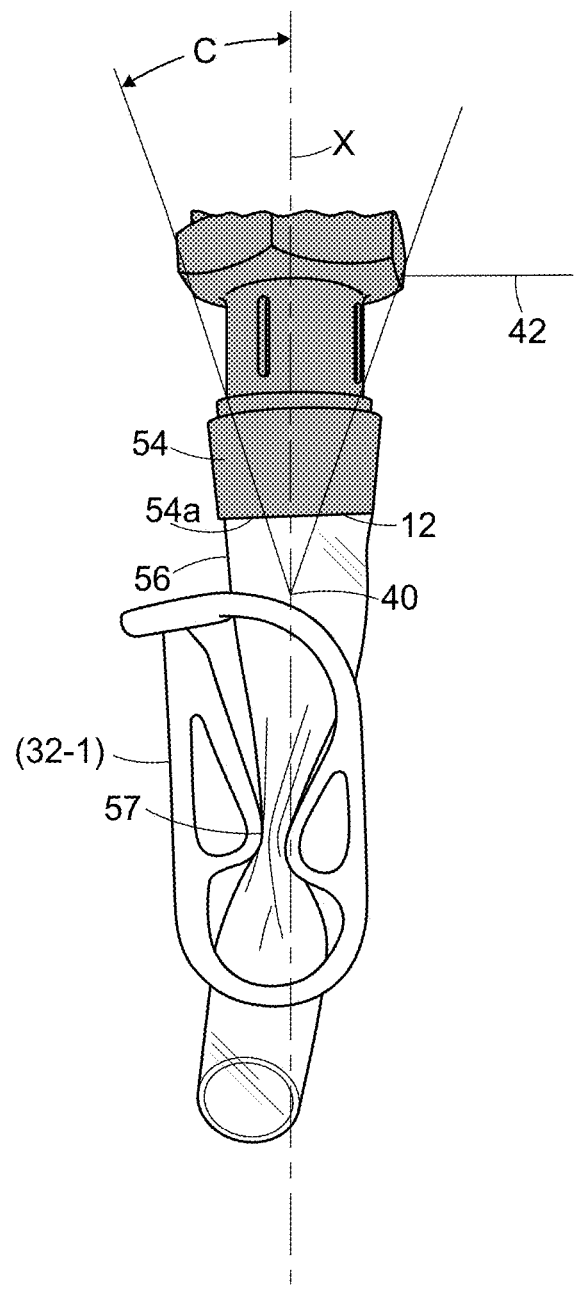
FIG. 16 is another side view of the lower portion with additional annotation.

The separation efficiencies provide greater insights into the phototactic behavior, under these conditions, of an in-situ zooplankton community taken from two distinct waterbodies. Although there was some overlap in the zooplankton community composition between the two lakes (e.g., *D. ambigua*, *Diaptomus* spp, copepodites, nauplii), there were distinct genus and species as well (e.g., *D. catawba*, *D. mendotae*, *Diaphanosoma brachyurum*, *Microcyclops rubellus* and *Mesocyclops edax*.). Community composition and distribution could ultimately influence the separation efficiencies that could be achieved for any given waterbody. Additionally, knowledge of the separation efficiencies of the individual zooplankters could potentially allow for the selection of a separation time based upon a target organism. FIG. 10 provides a summary of the individual zooplankter behavior that was observed in samples taken from Lake Cochichewick and Willand Pond in 2014. These are comparable to those previously observed as shown in Table 1 of FIG. 11 and Table 2 of FIG. 12, respectively.

The design of the separation device with a completely darkened chamber and transparent collection tube provides the conditions necessary to initiate a positive phototactic response to a sudden change in light intensity (Buchanan, C. B. Goldberg and R. McCartney, 1982, "A laboratory method for studying zooplankton swimming behaviors," *Hydrobiologic*, 94, 77-89). Although the light intensity was not measured during these experiments, it was assumed that the light intensity exceeded the threshold for instantaneous relative change in light intensity of 0.2 uE m-2 s-1 (the rheobase) necessary for photobehavior to occur (Ringelberg, J., 1964, "The positively phototactic reaction of *Daphnia magna* Straus: a contribution to the understanding of diurnal vertical migration," *Neth. J. Sea Res.*, 2:319-406, Daan, N. and J. Ringelberg, 1969, "Further studies on the positive and negative phototactic reaction of *Daphnia magna* Straus," *Neth. J. Zool.*, 19:525-540). A positive phototactic response could be anticipated as a result of exposure to a narrow stimulus beam (Forward, R. B. Jr., 1988, "Diel vertical migration: Zooplankton photobiology and behavior," *Oceanogr. Mar. Biol. Annu. Rev.*, 26: 361-393) (highly directional light) with an angular light distribution that approximates 0° (Schallek, W., 1942, "The vertical migration of the copepod *Acartia tonsa* under controlled illumination," *Biological Bulletin*, 84:98-106). Body axis orientation would result from dorsal beam contrast (45° or less) (Ringelberg, J., 1964, "The positively phototactic reaction of *Daphnia magna* Straus: a contribution to the understanding of diurnal vertical migration," *Neth. J. Sea Res.* 2:319-406) (Ringelberg, J., B. J. G. Flik and R. C. Buis, 1975, "Contrast orientation in *Daphnia magna* and its significance for vertical plane orientation in the pelagic biotope in general," *Neth. J. Zool.*, 25:454-475) that would control the direction of movement in the vertical plane. The orientation of the device (darkened above, light below) serves to reinforce body axis orientation as a flight response from predators.

An adapter with a minimum diameter of 20 mm was used as the temporary darkened physical separation. This was a diameter sufficient to allow for a narrow stimulus beam of light to be refracted at an angle approximating 45° (or less) to the vertical plane and to meet the spatial needs of the migrating zooplankton. A cylindrical collection tube (25 mm diameter) continuously assured that the spatial needs of the migrating zooplankton would be met. Although experiments were not conducted on the behavior of the migrating zooplankton in devices with other elements (i.e., rubber tubing) with small diameter (e.g., 13 mm or less), it is assumed that the response would be similar. Consequently, it is possible that elements of a separation device with diameters less than 13 mm may inhibit the movement of migrating zooplankton.

The volume of the zooplankton sample to be collected needed to consider migration potential and contrast orientation. By creating a sudden stimulus of dark to light to maximize migration rates, (Buchanan, Goldberg and McCartney 1982) it could be ensured that the maximum migration distance of 42 cms could be achieved within a specified time (Daan & Ringelberg 1969). Additionally, it was needed to leverage the influence of contrast orientation by driving the zooplankton past the angle of 48° to the normal. The optimum volume to be collected using a collection tube was determined to be 50 mls.

Favorable conditions were established for the response to occur by using ambient light to simulate the spectral distribution of irradiance in the natural system. Filtered lake water was used to address issues related to dissolved substances and response of the zooplankton to rapid changes in water temperature. (Buchanan, Goldberg and McCartney, 1982).

The device is easily assembled and can be used to obtain well separated in situ samples of phytoplankton and zooplankton. The samples can easily be processed on site, thereby reducing valuable time either in the field or in the laboratory. Issues related to sample handling and transport were considered, and how that might affect the design of the collection tubes. Collection tubes containing samples of live zooplankton can be sealed with a cap and easily transported. The phytoplankton can be easily transported by placing a cap on the darkened chamber. To simplify transport and reduce processing time in the lab, dried zooplankton and phytoplankton samples can be obtained while in the field. This would also reduce the possibility of bacterial contaminations of the samples. Filter cones and modified collection tubes were developed to allow for the discharge of water. The filter cones can be placed in drying chambers for 2-8 hours and then placed into desiccators. There are competing limitations to the device and the method that relate to a vacuum being created within the chamber and incremental clogging of the filter cone as the phytoplankton sample is being discharged. These limitation can be overcome by the sizing of the filter cones and including agitation ports in the collection tubes.

DISCUSSION

The experiments described herein provide novel data, using an in situ sample to quantify phototactic behavior under a controlled setting from two distinctly different water bodies. Although phototaxis has been previously used to separate plankton, there are no published studies that describe the actual separation efficiencies that could be achieved. From visual observations, phototactic behavior can be used to harvest zooplankton. The composition of the sample was unknown, however it was assumed that macrozooplankton would migrate more quickly than microzooplankton. Additionally, the amount of incidental capture of the phytoplankton portion was completely unknown. The harvest achieved for the zooplankton portion surpassed expectations and provided insight into the level of incidental phytoplankton capture that could be anticipated. Conversely, a phytoplankton portion can be harvested that would be relatively free of zooplankton biomass. The passive nature of the device proved to be of great value, as other tasks could be conducted while the sample was separating, thereby saving valuable time.

In regards to the zooplankton, it is possible that the composition and distribution of the biomass had an influence on the separation efficiencies that were observed. It is also possible that lake trophic status exerts a significant influence on separation efficiency. The level (5% or less) of incidental capture of the phytoplankton is puzzling, specifically the Cyanobacteria, in the zooplankton samples. It is assumed that what is observed as incidental capture is a result of depuration as the zooplankton move from an environment of high concentration of phytoplankton to a lower concentration.

It is anticipated that samples obtained after using the method and device would yield relatively precise measures of biomass and weight specific toxicity for zooplankton and phytoplankton. The phytoplankton information could be used to provide a profile of exposure potential across a range of waterbodies and to support decisions regarding use attainability. The zooplankton information could be used to quantify transfer between the two trophic levels and provide insight into the potential for further bioaccumulation.

Referring to FIGS. 13-16, plankton separating or separation device 50 is another embodiment of a separation device in the present invention which differs from separating devices 6 and 8 (FIGS. 1J and 1K) in that the darkened container or chamber 52 and transparent collection chamber, region, container, cartridge or tube 56 is much smaller, and can separate much smaller samples 11 of water and plankton. This can make the plankton collection process on a water body quicker and easier. The plankton separation device 50 is now described as shown in an upright orientation during use.

The darkened chamber 52 in one embodiment, can have a generally cylindrical darkened or light impervious tube member extending along a longitudinal central axis X having a maximum outer perimeter or diameter $OD_b$ portion of about 29 mm to 33 mm (1.14-1.3 inches), about a 26-28 mm (1-1.1 inch) inner width or diameter, a tube wall thickness of about a 0.9 mm (0.03 inches), a height D of about 109 mm (4.29 inches), and hold a volume of about 50 mls of liquid, which is much less (about 20 times less) than the 1 liter darkened chambers of separating devices 6 and 8. An openable cap 58 can be screwed onto the top or proximal end of the darkened chamber 52. A darkened transitional adapter or area 54 having a circular outer perimeter and an inner width or diameter that is narrowed from or smaller than the inner diameter of the darkened chamber 52 can be coupled or connected to, or extended from the bottom of or below the darkened chamber 52 along central axis X, such as to an exit port of the darkened chamber 52. The outer width or diameter of the darkened transitional adapter 54 can be smaller than that of the darkened chamber 52. The darkened transitional adapter 54 is also darkened or light impervious, and can have an inner diameter narrowing down to about 20 mm (0.78 inches)±2 mm (0.08 inches) such as about 19 mm (0.75 inches) but greater than 13 mm, a height E of about 30 mm (1.18 inches), and a volume of about 9 mls. The transparent collection tube 56 can be coupled or connected to, or extended from the bottom of or below the darkened transitional adapter 54 along central axis X, such as from the exit port 54a of the darkened transitional adapter 54 with a maximum tube outer diameter $OD_t$ of about 19 mm (¾ inches). The transparent collection tube 56 can be clear to allow light such as ambient light, to enter to cause plankton 15 such as zooplankton to migrate toward the light into the transparent collection tube 56. The exit port 54a of the darkened transitional adapter 54 can produce a narrow defined circular beam or spot of light with high contrast from the transparent collection tube 56 vertically upwardly from below along longitudinal central axis X into darkened chamber 52, which draws phototactic plankton 15 downwardly vertically into the transparent collection tube 56, such as previously described. An openable ratchet clamp or valve (32-1) can releasably pinch or compress the transparent collection tube 56 to fluidly close or seal the tube 56 below the darkened transitional adapter 54. The portion of the transparent collection tube 56 above the ratchet valve (32-1) can have an inner width or diameter $1D_t$ that is smaller than that of the darkened transitional adapter 54, such as about 16 mm (0.63 inches), a height F of about 12 mm (0.47 inches), and a volume of about 3 mls. The transparent collection tube 56 can have a generally annular cross section, being tubular above the ratchet valve (32-1). As the transparent collection tube 56 moves downwardly and enters the ratchet valve (32-1), the tube 56 becomes tapered until reaching the pinch or close off point 57 of the ratchet valve (32-1), which is a length or height G from the top of the ratchet valve (32-1) of about 32 mm (1¼ inches) that contains an additional volume of about 5 mls. As a result, the transparent collection tube 56 extending to point 57 can have a length L of about 44 mm (1.75 inches) and can hold a volume of about 8 mls which is more than 6 times less than the 50 ml capacity of the transparent collection tube (30-2) of separating device 8. The total volume capacity of the plankton separation device 50 can be about 70 mls or less, such as about 67 mls. The darkened outer perimeter or diameter $OD_b$ to transparent collection tube outer diameter $OD_t$ ratio can be about 1.4-1.7 to 1, the $OD_b$ to transparent collection tube inner diameter $ID_t$ ratio can be about 1.75-2 to 1, the transparent collection tube length L to $ID_t$ ratio can be about 2.5-2.9 to 1 such as 2.75 to 1, and the ratio of the dark region length to transparent collection tube length L can be about 3-3.4 to 1 such as 3.2 to 1. The ratio of liquid volume of the darkened areas 52 and 54 to the transparent collection tube 56 can be about 7.4 to 1.

Cone angle A, which can be 48° or less such as 46°, extends from a point 38 that is on central axis X within the darkened portions such as the darkened transitional adapter 54, and intersects or passes through lateral baseline 42 at about the widest maximum perimeter dimension or diameter of the darkened chamber 52 closest to the transparent collection tube 56. Cone angle B, such as 23°, which is less than 48° or 46°, extends from a point 44 along central axis X, at the transition between the darkened transitional adapter 54 and the transparent collection tube 56, to the outer perimeter dimension of darkened chamber 52 on baseline 42. Cone angle C which can be about 20°±2°, extends from a point 40 on central axis X within transparent collection tube 56 to the maximum outer perimeter dimension of darkened chamber 52 at baseline 42. Angles A, B and C can have the same function and the same or similar operation or effect as previously described, but are relative to a smaller sized darkened chamber 52 and transparent collection tube 56, with smaller diameters, lengths and volumes. For example, the shadow of darkened chamber 52 above plankton 15, such as zooplankton that have migrated towards light into transparent collection tube 56, past a cone angle of 48° or less, such as past cone angle B at 23°, can form a concentric contrast shadow relative to the plankton 15 within the interior of the transparent collection tube 56. The contrast shadow can simulate a predator to the plankton 15, which tends to cause the plankton 15 to swim downwardly within the transparent collection tube 56 away from the darkened chamber 52 to maintain separation of the plankton in separation device 50. The cone angle C of about 20°±2° can extend from point 40 along longitudinal axis X, that is within transparent collection tube 56 about ¼ the way down into tube 56. About ¾ of the length of transparent collection tube 56 can extend downwardly below the 20° cone angle C. This provides enough downwardly vertical space within transparent collection tube 56 where collected plankton 15 can swim downwardly far enough away from darkened chamber 52 past cone angle C in response to the simulated predatory contrast shadow produced, where the plankton 15 will not migrate back into the darkened chamber 52.

By having a 50 ml darkened chamber 52 with an inner diameter of about 26-28 mm, such as 28 mm (1.1 inches), not only is the liquid volume much smaller, but the outer perimeter or diameter dimension of the darkened chamber 52 is about three times smaller than the outer perimeter diameter of the 1 liter darkened chambers of separating devices 6 and 8. This in turn, results in the point 40 from which the 20°±2° cone angle C extends, being located about ⅓ the distance from baseline 42 than in separating devices 6 and 8. Consequently, not only is the plankton separation device 50 much narrower than separating devices 6 and 8 (about three times narrower), but it is also much shorter in length as well (about 2.5 times shorter). The small size and volume of plankton separation device 50 allows for easy filling, handling, use, storage and transportation of separation device 50, making it suitable for use in the field. Although the liquid volume of plankton separation device 50 is about 20 times smaller than devices 6 and 8, effective separation can still be obtained. The plankton does not have to swim as far when migrating. The furthest that plankton has to swim through the darkened chamber 52 and the darkened transitional adapter 54 before reaching the transparent collection tube 56 is about 139 mm. Although the transparent collection tube 56 at port 54a of the darkened transitional adapter 54 has an initial inner diameter of about 16 mm (0.63 inches) which is smaller than that in separating devices 6 and 8, this dimension is still large enough (larger than 13 mm) so that migration of phototactic plankton 15 is not hindered. In addition, the small narrow inner diameter of darkened chamber 52 can be vertically orientated to concentrate floating phytoplankton such as Cyanobacteria 15b (FIG. 17) into a narrow vertical water column at the top of the darkened chamber 52 to allow for consistent sample concentrations of Cyanobacteria 15b to be removed, such as by suction or hydraulic pressure. This allows the collection of floating Cyanobacteria 15b from a small 50 ml darkened chamber 52. Typically, Cyanobacteria 15b is attracted to the inner side walls of the darkened chamber 52, and if the inner diameter of the darkened chamber 52 is too wide or large, the floating Cyanobacteria 15b will form a thin floating ring on top of the water with little or no Cyanobacteria 15b in the center, which can make collected samples inconsistent in Cyanobacteria 15b concentration.

Figure 17:
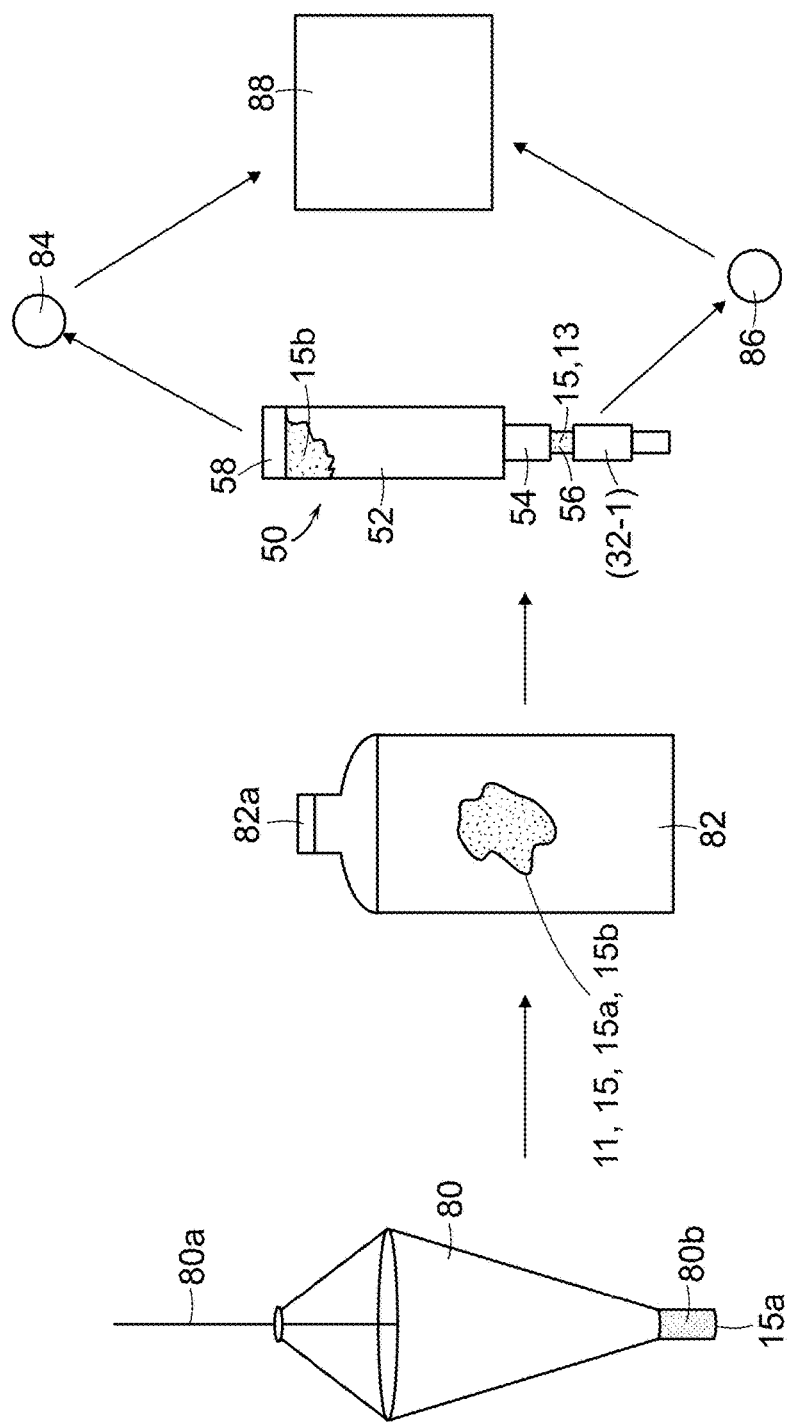
FIG. 17 is a flow chart of an embodiment of a plankton sampling and processing procedure in the present invention.

Referring to FIG. 17, for sampling and processing plankton, a plankton tow net 80 can be used to collect a concentrated sample of plankton 15a in a body of water such as a pond, lake or other bodies of water. The tow net 80 can have about a 50 um pore size (such as 53 um), a 15 cm opening and a 50 cm length. The tow net 80 can be lowered from a boat as a vertical tow to a depth of about 3 meters, and pulled upwardly with towline 80a at a rate of about 0.5 meters per second. If the tow net 80 is used from shore, the tow net 80 can be thrown out into the body of water a distance of about 5 meters, allowing the cod end 80b to submerge, and then be pulled to shore. After the tow net 80 is pulled in, the sides of the tow net 80 can be gently rinsed, for example with pond or lake water. The entire net sample can reduce to fill the cod end 80b with about 250 mls of a concentrated plankton sample 15a.

Figure 22:
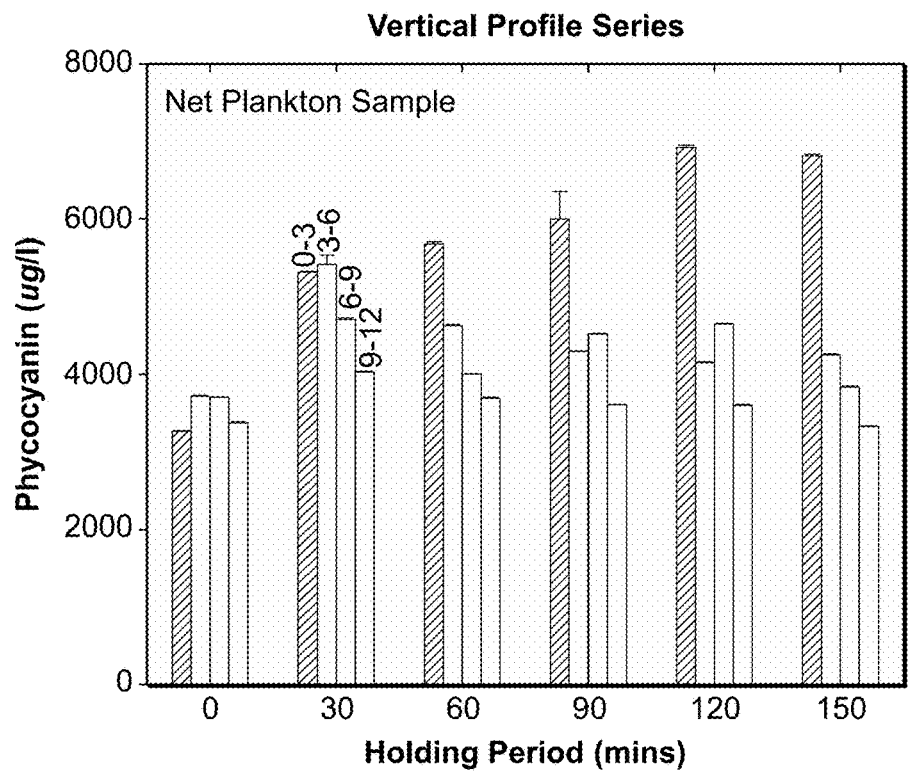
FIG. 22 is a graph depicting phycocyanin (ug/l) versus holding period time.

The concentrated sample of plankton 15a can be transferred into a darkened bottle or container 82, such as an amber bottle, which can have a removable cap 82a. The sample of plankton 15a can be kept dark and cool for a darkened holding time period of a minimum of about 2 hours to allow phytoplankton such as Cyanobacteria 15b to undergo a process of respiration. As seen in the graph of FIG. 22 depicting the level of accessory pigment phycocyanin (ug/l) detected versus holding period time, a holding period of 2 hours has the highest levels of phycocyanin and provides maximum results, but a holding period of 2 to 2½ hours (or at least two hours), or a holding period of about 1½-2½ hours, can be used as well. A holding period of 4 hours can also be possible in the field. The process of respiration allows the consumption of carbohydrates within the Cyanobacteria 15b, thereby decreasing the weight of the carbohydrate ballast within the cells. A decrease in the weight of the carbohydrate ballast increases the relative buoyancy of the Cyanobacteria 15b causing the Cyanobacteria 15b to float in water. After at least about 2 hours, the sample of plankton 15a can be gently mixed for about 30 seconds and can now be a sample 11 of water and plankton ready for separation.

Figure 18:
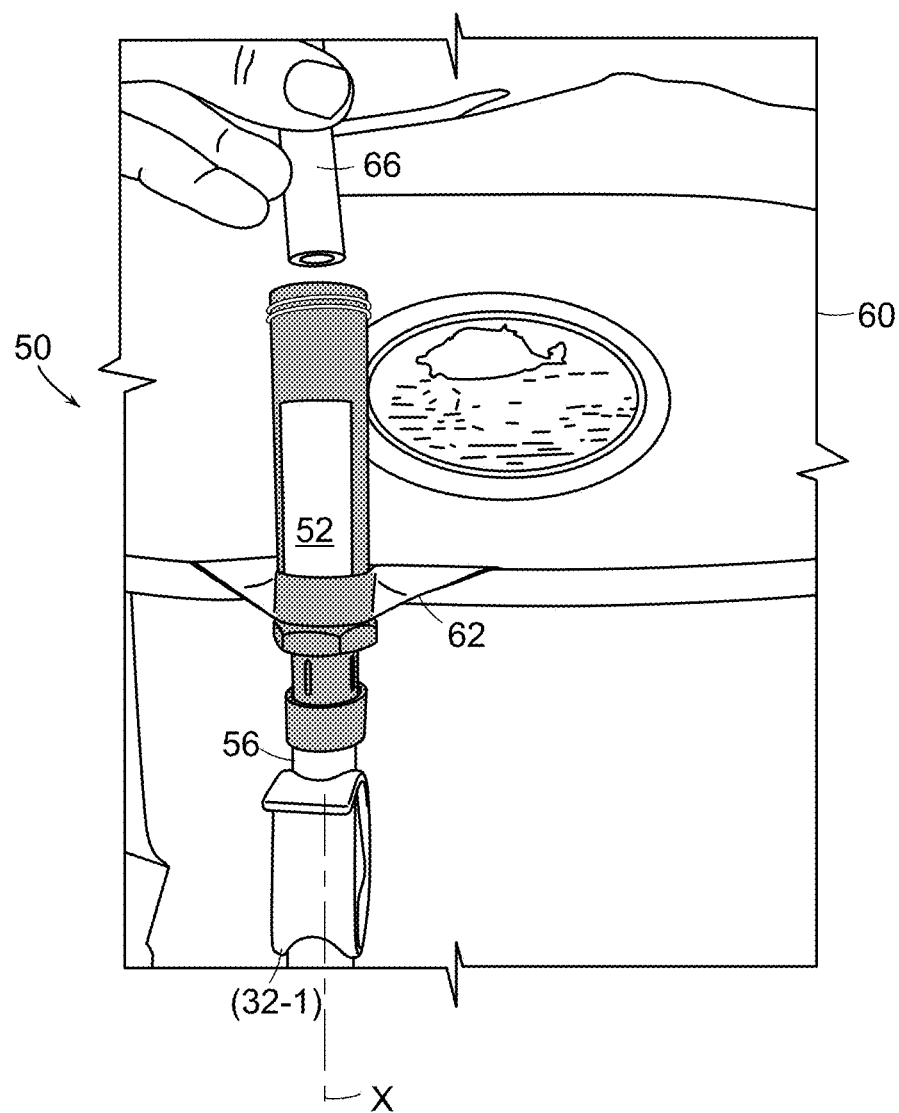
FIG. 18 is a front view of the plankton separation device of FIG. 13 being filled during use.
Figure 19:
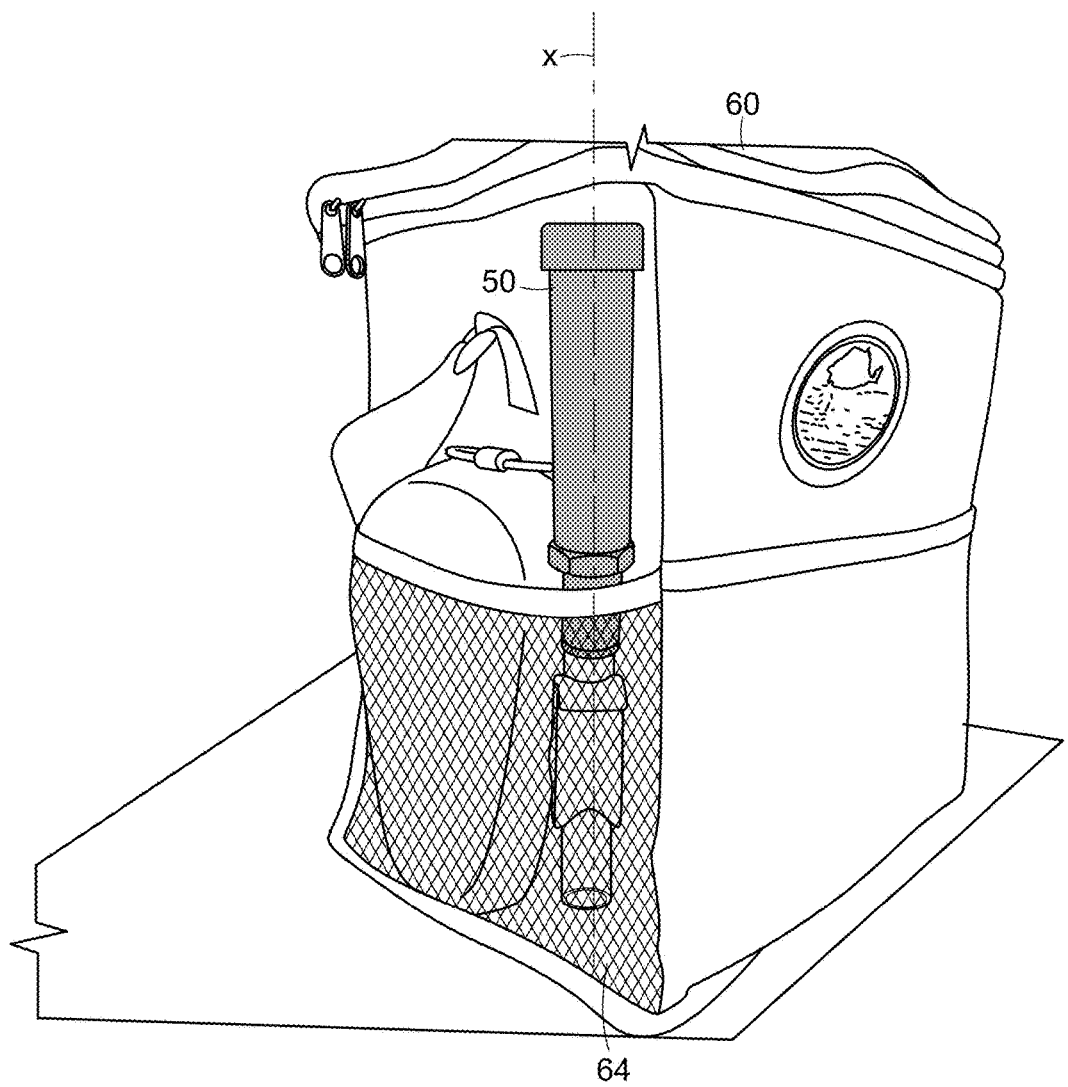
FIG. 19 is a front view of the plankton separation device thereof being restrained during use in an upright orientation by the webbing of a carrying pack.

Referring to FIG. 18, the plankton separation device 50 can be secured or held in a vertical or upright position with cap 58 removed, and ratchet clamp (32-1) tightly fluidly closing the end of transparent collection tube 56. The plankton separation device 50 can be secured by a fixture or strap 62 to a carrying pack 60 that is used for transporting and storing samples and equipment for the sampling and separation process. The sample 11 of water and plankton can be introduced into the top of the darkened chamber 52 by a rubber hose 66 (an amount close to about 70 mls), or decanted directly from the darkened bottle or container 82. By having a separation device 50 with a volume of about 70 mls, three devices 50 can be used with a single 250 ml concentrated plankton sample 15a from one tow of net 80, for processing in triplicate. The transparent collection tube 56 can be filled with filtered water 13, or alternatively, can be filled with the sample 11 of water and plankton. The cap 58 is then closed so that the darkened chamber 52 can be kept dark. The plankton separation device 50 can also be held in an upright orientation within a mesh pocket or webbing 64 on the outside of the carrying pack 60 as seen in FIG. 19.

Figure 20:
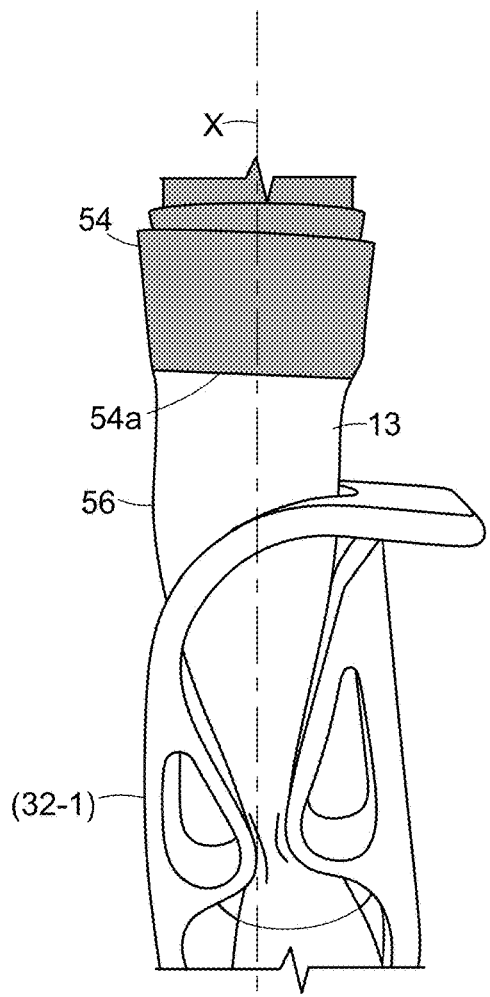
FIG. 20 is a side view of the transparent collection container tube at the start of the separation period.
Figure 21:
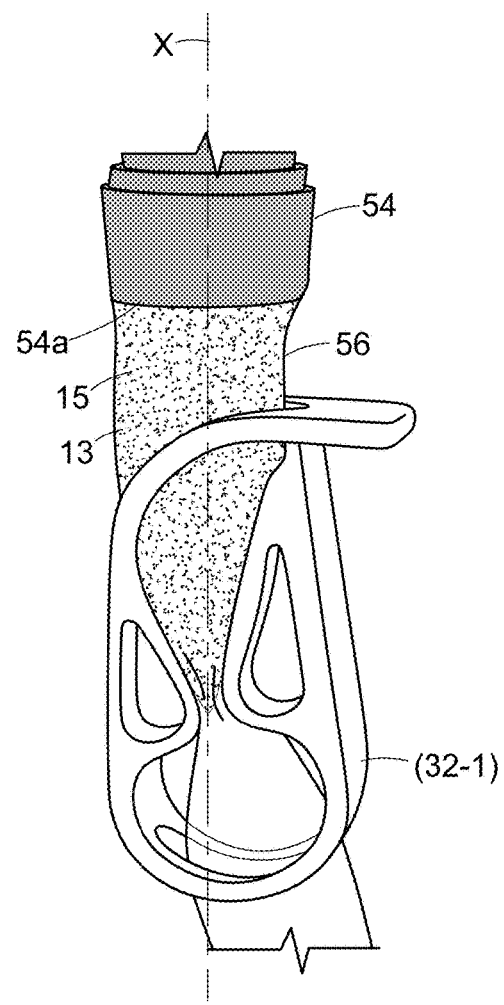
FIG. 21 is a side view of the transparent collection container tube at the end of the separation period.
Figure 23:
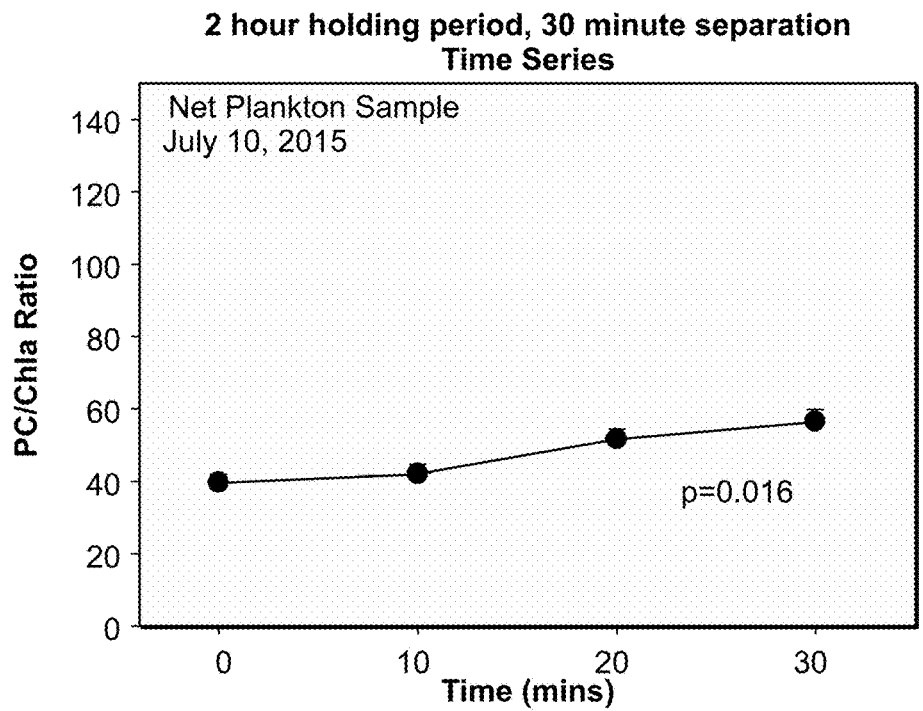
FIG. 23 is a graph depicting PC/Chla ratio versus separation time.

With the plankton separation device 50 being in an upright position and the darkened chamber 52 being on top or above the transparent collection tube 56 in alignment along longitudinal central axis X, the separation device 50 can be kept in this position unobstructed and still or motionless, for a separation time period of about 20-30 minutes, more preferably 30 minutes (or at least 30 minutes), as is advisable by the graph of FIG. 23, which depicts (phycocyanin to chlorophyll) PC/Chla ratio versus separation time being highest at 30 minutes. The separation device 50 can be secured to the carrying pack 60 to prevent tipping over for the separation time period (as shown in FIGS. 18 and 19), for directing or allowing ambient light to illuminate or shine into the transparent collection tube 56, but alternatively can be held upright by other suitable means known in the art, such as racks or clips that allow ambient light to reach or illuminate the transparent collection tube 56. FIG. 20 shows the transparent collection tube 56 at the start of the separation process T=0, before plankon 15 has migrated into the transparent collection tube 56. FIG. 21 shows the transparent collection tube 56 at the end of a T=30 minutes separation time period in which plankton 15, such as phototactic zooplankton has migrated into and concentrated within the transparent collection tube 56, and where the Cyanobacteria 15b has achieved positive buoyancy. As seen in the graphs of FIGS. 22 and 23, a period of about 2 hours for holding the sample 11 of plankton and water in the dark and separating in separation device 50 with light for about 30 min., has been found to optimize test results, which can be consistent and optimal for most test situations.

At the same time, referring back to FIG. 17, phytoplankton such as Cyanobacteria 15b can float or concentrate within the upper 3 mls, 5 mls or 3-5 mls of the narrow vertical water column in the darkened chamber 52. By causing phototactic plankton 15 such as zooplankton to migrate vertically downwardly towards light in the transparent collection tube 56, and floating the phytoplankton 15b or Cyanobacteria on top of the water column, better separation can be obtained for the Cyanobacteria for a better or more pure sample. The cap 58 is then unscrewed, and the top 3 mls, 5 mls or 3-5 mls of the water column within the darkened chamber 52 can be removed with suction or hydraulic pressure, such as with a 5 ml transfer pipette, and a sample 84 of Cyanobacteria 15b can be placed within a labeled 5 ml microvial. The sample 84 of Cyanobacteria 15b can be frozen for a minimum of about 4 hours and then thawed. The sample 84 of Cyanobacteria 15b can be analyzed in an analysis step or procedure 88, by placing the sample 84 in a cuvette and taking phycocyanin (PC) and chlorophyll-a (Chla) readings with a fluorometer when the sample is between about 20° to 24° C. (68° to 75° F.).

In addition, if desired, a sample 86 of plankton 15 such as the zooplankton can be removed from the transparent collection tube 56, such as by opening ratchet valve (32-1), and analyzed as desired in an analysis step or procedure 88, as known in the art, and which can be a different procedure than for Cyanobacteria 15b. Based on the analysis of samples of phytoplankton, Cyanobacteria, and/or zooplankton, the state or health of the body of water from which the samples were taken can be analyzed, and predictions may be made.

Figure 24:
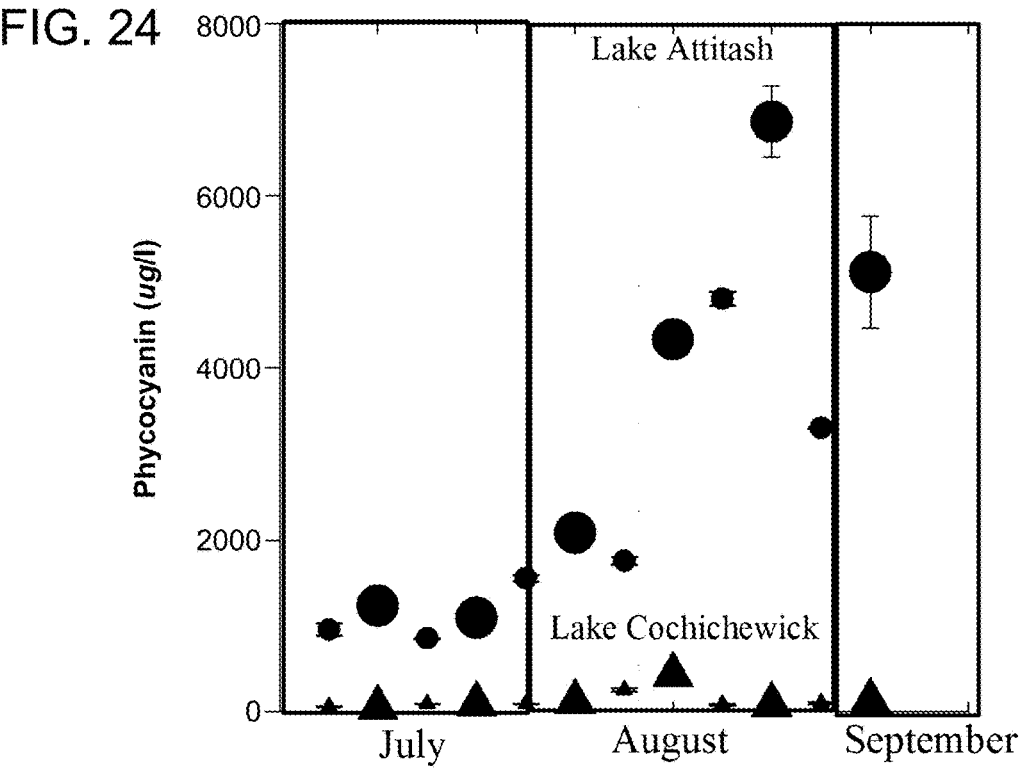
FIG. 24 is a graph showing phycocyanin (ug/l) versus July to September 2015 time period for Lake Attitash and Lake Chochichewick.
Figure 25:
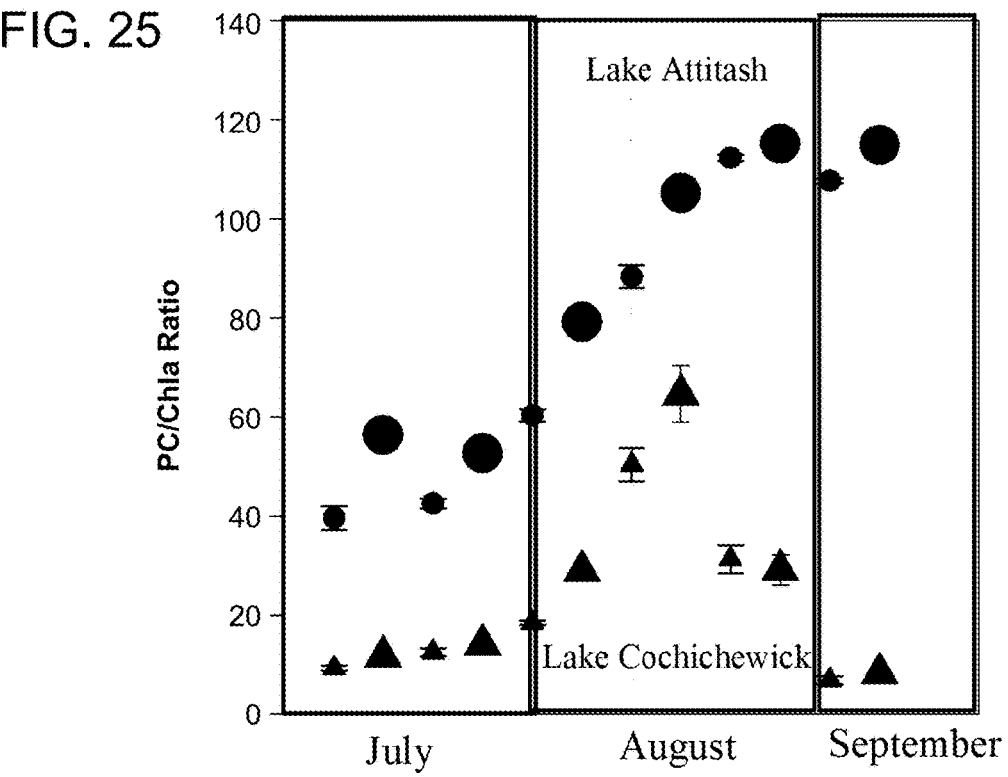
FIG. 25 is a graph showing PC/Chla ratio versus July to September 2015 time period for Lake Attitash and Lake Chochichewick.

FIG. 24 depicts a graph showing phycocyanin (ug/l) levels versus time period in July, August and September 2015 for Lake Attitash and Lake Cochichewick, which plankton separation device 50 was used to separate phytotactic plankton 15 and Cyanobacteria 15b. FIG. 25 depicts phycocyanin to chlorophyll PC/Chla ratio for the time period July, August and September 2015 for Lake Attitash and Lake Cochichewick. The PC/Chla ratio with regard to seasonal succession and biology of transition, can be analyzed, and increases or changes can be used in forecasting blooms or toxic levels from Cyanobacteria 15b. Dramatic increases and/or levels of PC/Chla ratios at particular times or dates in the season can be used to decide when to conduct toxic testing to determine Cyanobacteria toxin levels. Sampling, separation and analysis in the present invention using plankton separation device 50 can be relatively inexpensive, while toxin testing procedures for determining actual toxin levels can be costly. Therefore, using plankton separation device 50 and obtaining PC/Chla ratios can be used to forecast or determine when to conduct costly toxin testing.

Figure 26:
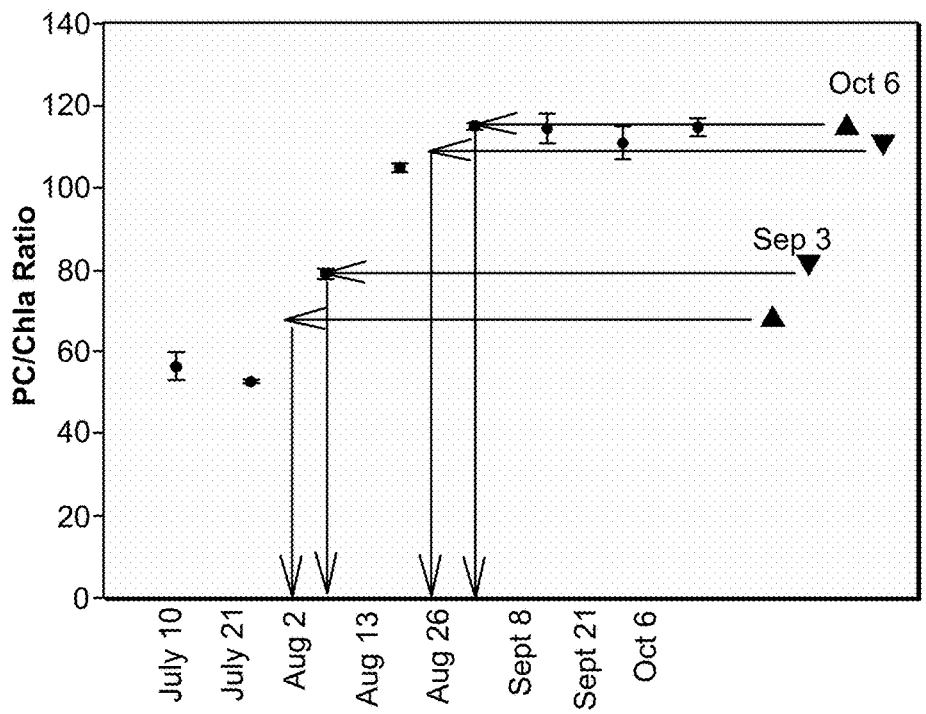
FIG. 26 is a graph showing PC/Chla ratio versus specific dates.

FIG. 26 depicts phycocyanin in to chlorophyll PC/Chla ratios for specific dates in July through October 2015 on lake Attitash, and includes dates of September 3 and October 6 indicated by the triangles of when a plankton bloom actually occurred which produced toxins. The arrows from the September 3 and October 6 dates horizontally point to specific PC/Chla ratios and the corresponding test or sampling day on August 2 and August 26, which corresponds to a dramatic PC/Chla ratio increase in the concentrated Cyanobacteria sample, that occurred 4-6 weeks or well before the actual bloom. Additional arrows are added to the graph to indicate interpolated data points and dates which would correspond with the actual blooms. In view of the graph of FIG. 26, and the analysis of the data, dramatic increases in PC/Chla ratio of the concentrated Cyanobacteria sample can be used to forecast potential plankton blooms that may occur about 4 to 6 weeks later.

Figure 27:
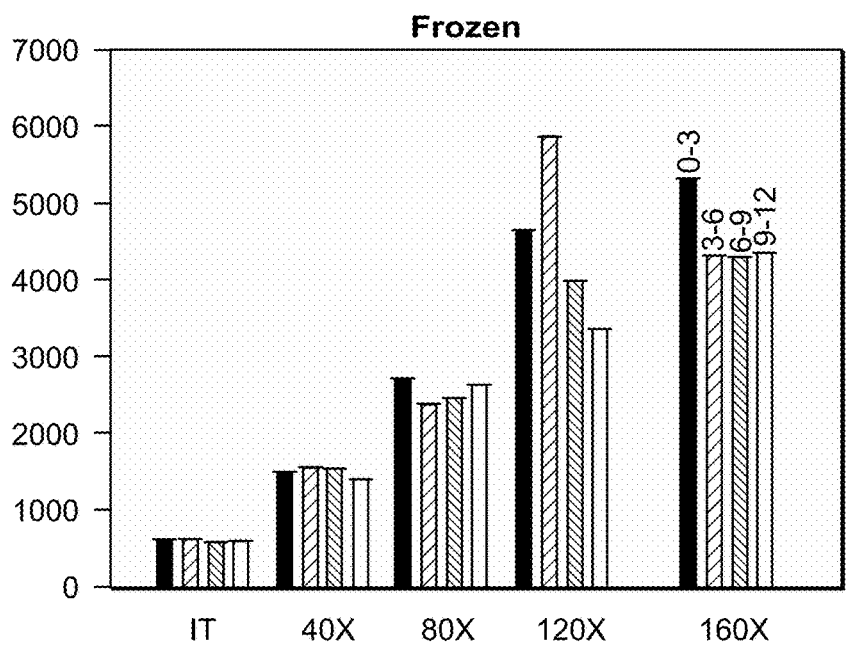
FIG. 27 is a graph showing different plankton concentration levels tested for Cyanobacteria floatation.

FIG. 27 is a graph showing different plankton sample 15*a* concentrations from Lake Attitash, which were tested for determining a concentration at which Cyanobacteria 15*b* can be visually observed to float after undergoing a process of respiration and separation. The least concentrated sample IT is a sample taken from the lake in a tube, and the most concentrated sample is 160× concentration, taken by a 50-53 um tow net 80. The 40×, 80× and 120× samples are concentrations that were diluted from a 160× concentration sample for testing purposes. It was determined that floating Cyanobacteria 15*b* was only visually observed in the 120× to 160× concentration plankton samples 15*a*, and which also provides a large enough level of plankton 15 and Cyanobacteria 15*b* to obtain consistent and accurate PC/Chla ratios. As a result, concentrated plankton samples 15*a* used with plankton separation device 50 are preferably obtained with a tow net 80 that concentrates plankton at least 120 to 160 times.

Figure 28:
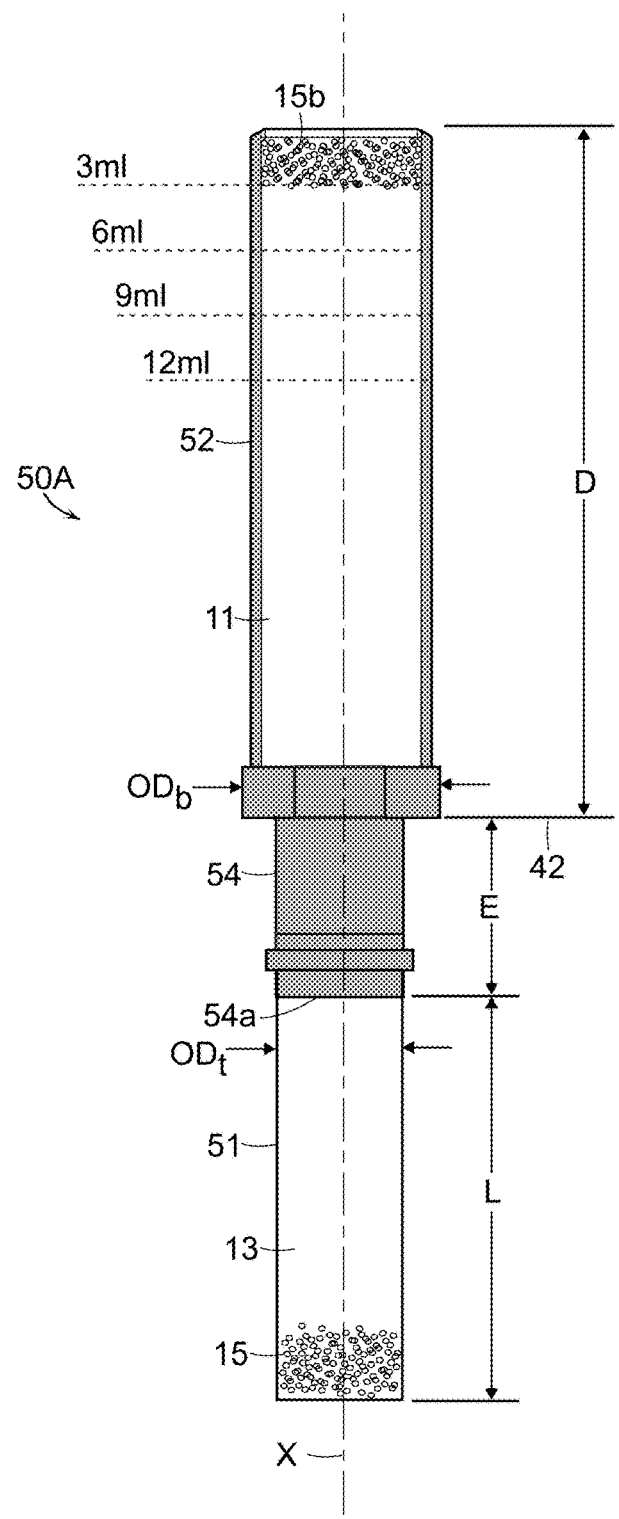
FIG. 28 is a front view of another embodiment of a plankton separation device in the present invention.

FIG. 28 depicts another embodiment of a plankton separating or separation device 58 in the present invention. Separation device 50A differs from separation device 50 in that instead of having a collection tube 56 that is pinched with a ratchet valve (32-1), a transparent collection, chamber, region, container or cartridge 51 can be attached, secured, connected or extended from darkened transitional adapter 54 for collecting migrated phototactic plankton 15, such as zooplankton. The transparent collection container 51 can be removably screwed, latched or press fitted to darkened transitional adapter 54 and can have a sealed bottom, such as in collection tube (30-2) in FIG. 1K. The length L and volume of transparent collection container 51 can be similar to that of collection tube 56. In general, separation of phototactic plankton 15 and phytoplankton or Cyanobacteria 15*b* with separation device 50A can be conducted in a similar manner as in separation device 50. Cyanobacteria 15*b* can float at the top of darkened chamber 52 in about the top 3 mls, 5 mls or 3-5 mls of a narrow water column therein.

Figure 29:
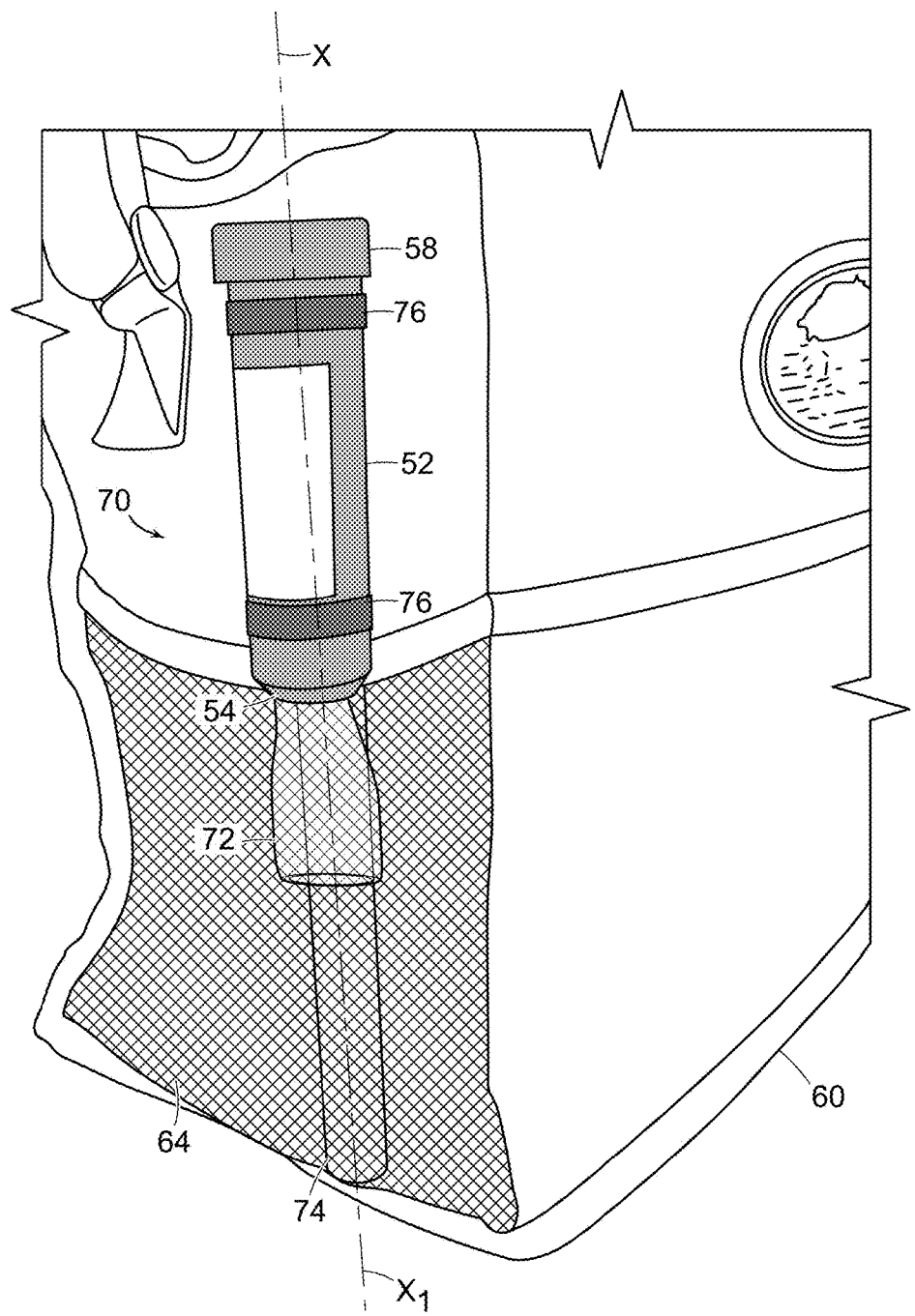
FIGS. 29 and 30 are perspective views of another embodiment of a plankton separation device in the present invention supported in an upright orientation by the webbing of a carrying pack.
Figure 30:
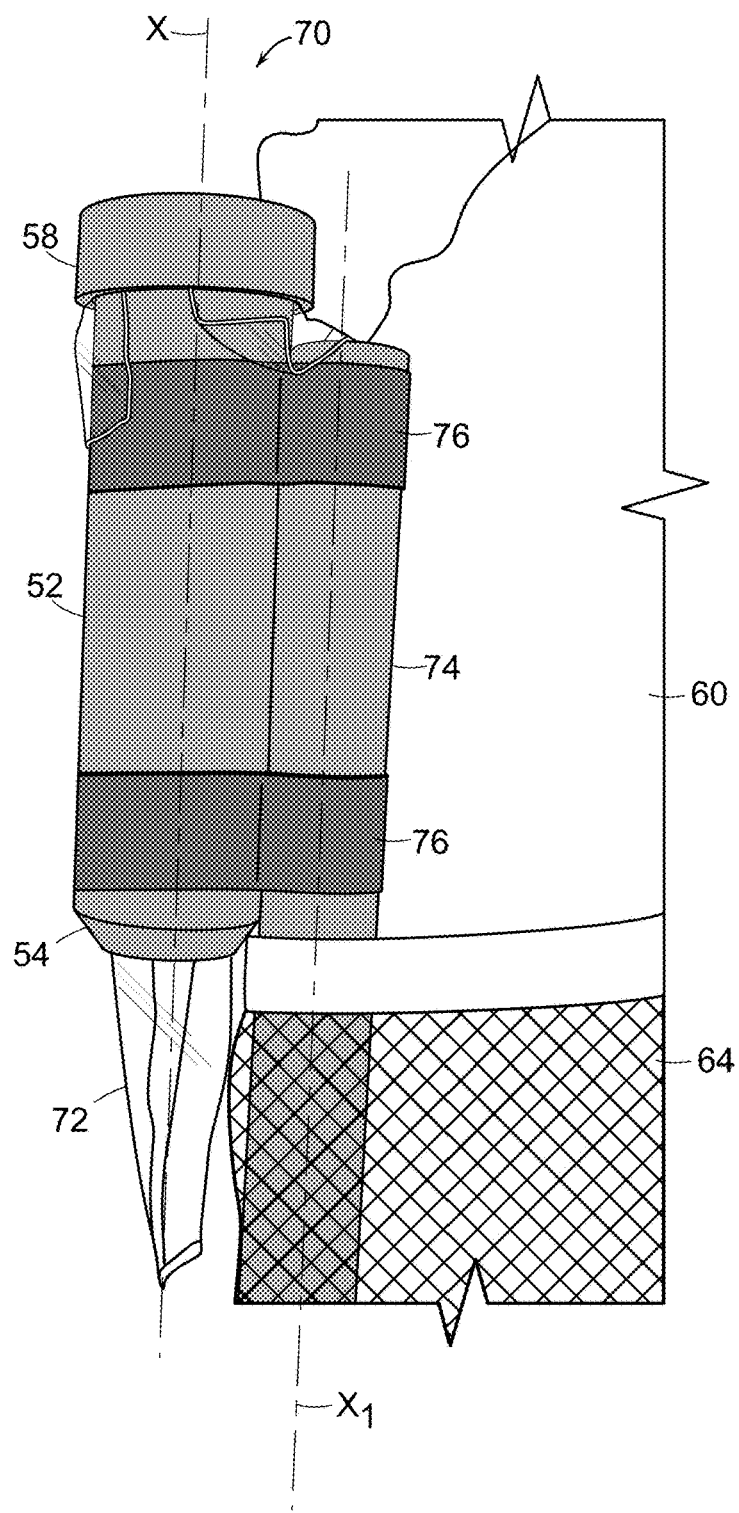
Figure 31:
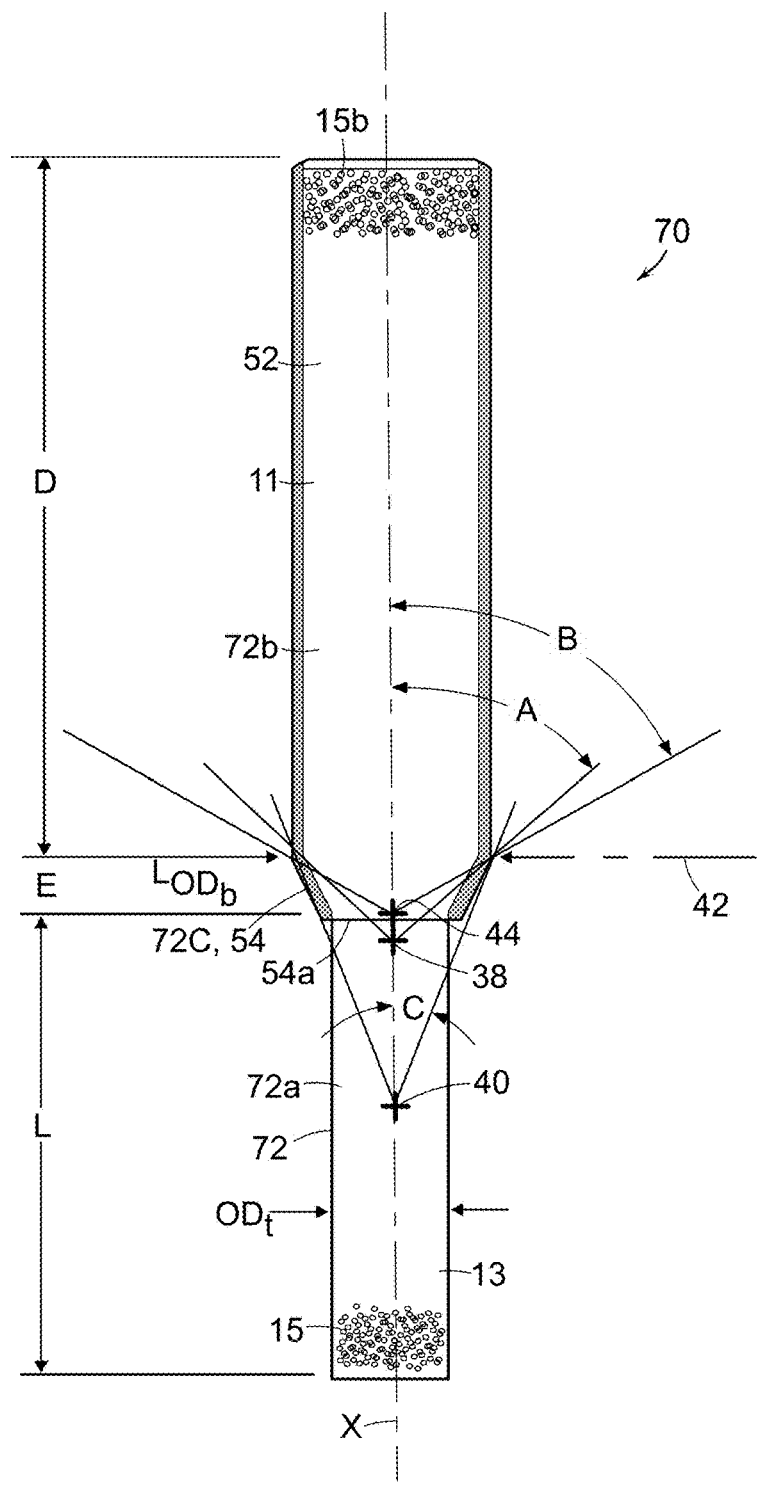
FIG. 31 is a front schematic view of the plankton separation device of FIG. 29.

Referring to FIGS. 29-31, plankton separating or separation device 70 is another embodiment of a separating device in the present invention. Separation device 70 differs from separation device 50 in that the construction of the darkened container or chamber 52, darkened transitional adapter or area 54, and transparent collection chamber, region, container or cartridge 72 can have some differences. The darkened chamber 52, darkened transitional area 54 and transparent collection cartridge 72 can be aligned along a longitudinal central axis X. The darkened chamber 52 can be generally cylindrical with a maximum outer perimeter or diameter portion $OD_b$ of about 28 mm to 30 mm (1.1 to 1.2 inches), an inner width or diameter of about 25 mm (0.98 inches) or 26 mm (1 inch) to 28 mm (1.1 inches), a tube wall thickness of about 0.9 mm (0.03 inches), a height D of about 100 mm (3.9 inches)+2 mm (0.08 inches), and a volume of about 50 mls. The darkened transitional area 54 can have an inner diameter narrowing down to about 20 mm±2 millimeters (0.78 inches±0.08 inches) such as about 19 mm (0.75 inches) but greater than 13 mm, a height E of about 5 mm (0.2 inches)+2 mm, and a volume of about 1 ml. The darkened transitional area 54 can be at the bottom or end of the darkened chamber 52 and can be connected to or extended therefrom. Transparent collection cartridge 72 can have a lower body portion that extends from the bottom or below the darkened transitional area 54 from exit port 54*a*, and can be a clear or transparent plastic container or a bag that is sealed at the bottom. The transparent collection cartridge 72 can extend below from the darkened transitional area 54 in a lower body collecting container portion, region or chamber 72*a*, with an initial outer diameter $OD_t$ or width and similar inner width or diameter $ID_t$ of about 20 mm+2 mm such as 19 mm that extends down to the sealed bottom for a length L of about 55 mm (2.2 inches) to 70 mm (2.75 inches), and have a volume below the darkened transitional area 54 of about 6 mls. The cartridge 72 can be thin-walled, so that the dimensions D, E and the inner diameters and volumes thereof, of the darkened chamber 52 and transitional area 54 generally correspond to cartridge 72.

Cone angle A, which can be 48° or less such as 46°, differs from separation device 50 in that point 38 can be slightly below the darkened transitional area 54. Cone angle B extends from point 44 at the transition between the darkened transitional area 54 and the transparent collection cartridge 72 and can be slightly above point 38. Cone angle B can range from about 60° to 80°, depending upon the size of the darkened transitional area 54. Cone angle C which can be about 20°±2°, can extend from a point 40 that can be within transparent collection cartridge 70 to about 40% down the length L of cartridge 72. The cone angles A and C can provide the same or similar function in operation as described above for causing phototactic plankton 15 such as zooplankton to swim downwardly into transparent collection cartridge 72 away from the darkened chamber 52. As a result, separation device 70 and/or cartridge 72 can have a liquid volume capacity of about 60 mls or less, such as 57 mls. The darkened outer perimeter or diameter $OD_b$ to transparent collection cartridge outer width or diameter $OD_t$ ratio can be about 1.2-1.7 to 1, the $OD_b$ to transparent collection cartridge inner diameter $ID_t$ ratio can be about 1.2-1.7 to 1, the transparent collection cartridge length L to $ID_t$ ratio can be about 2.5-3 to 1. The ratio of dark region length of darkened chamber 52 and transitional area 54 to transparent collection cartridge length L can be about 1.8-2 to 1. The ratio of liquid volume of the darkened areas 52 and 54 to the transparent collection cartridge 72 below area 54 can be about 8.5 to 1. In some embodiments, the transparent collection cartridge 72 can have an upper body portion 72*b* that can be extended, shaped, inserted, positioned, or fitted into or within the inner lengths/heights and diameters of the darkened chamber 52 and darkened transitional area 54 with a narrowing portion 72*c* in transitional area 54, and then the lower body portion 72*a* extends out of and below the inner diameter and port 54*a* of the darkened transitional area 54. The transparent collection cartridge 72 can be removably disposable, and thrown away after use, as part of personal protective equipment (PPE) requirements for handling samples with cyanotoxins. In other embodiments, the transparent collection cartridge can be extended, coupled or connected to the darkened transitional area 54 without being fitted and extending within the darkened chamber 52. The cartridge 72 in some embodiments can be a molded plastic container.

A round post 74 having a longitudinal axis $X_1$ can be secured to the side of the darkened chamber 52 by 2 spaced apart securement bands or members 76, with the axis $X_1$ being laterally offset and parallel to the longitudinal direction of the axis X of separation device 70. The post 74 can be used to support separation device 70 in an upright or vertical position along axis X by vertically inserting the post 74 into the inside of the mesh pocket 64 of carrying pack 60, with the darkened chamber 52, darkened transitional area 54 and transparent collection cartridge 72 being on the outside of the pocket 64, for providing good or unobstructed access to ambient light to the transparent collection cartridge 72.

The use and operation of plankton separation device 70 can be similar to that of separation device 50, including the collection of Cyanobacteria 15b. The removal of plankton 15, such as zooplankton in transparent collection cartridge 72 can be accomplished by cutting open or puncturing the bottom of the cartridge 72, and draining, or removing cartridge 72 from separation device 70.

Figure 32:
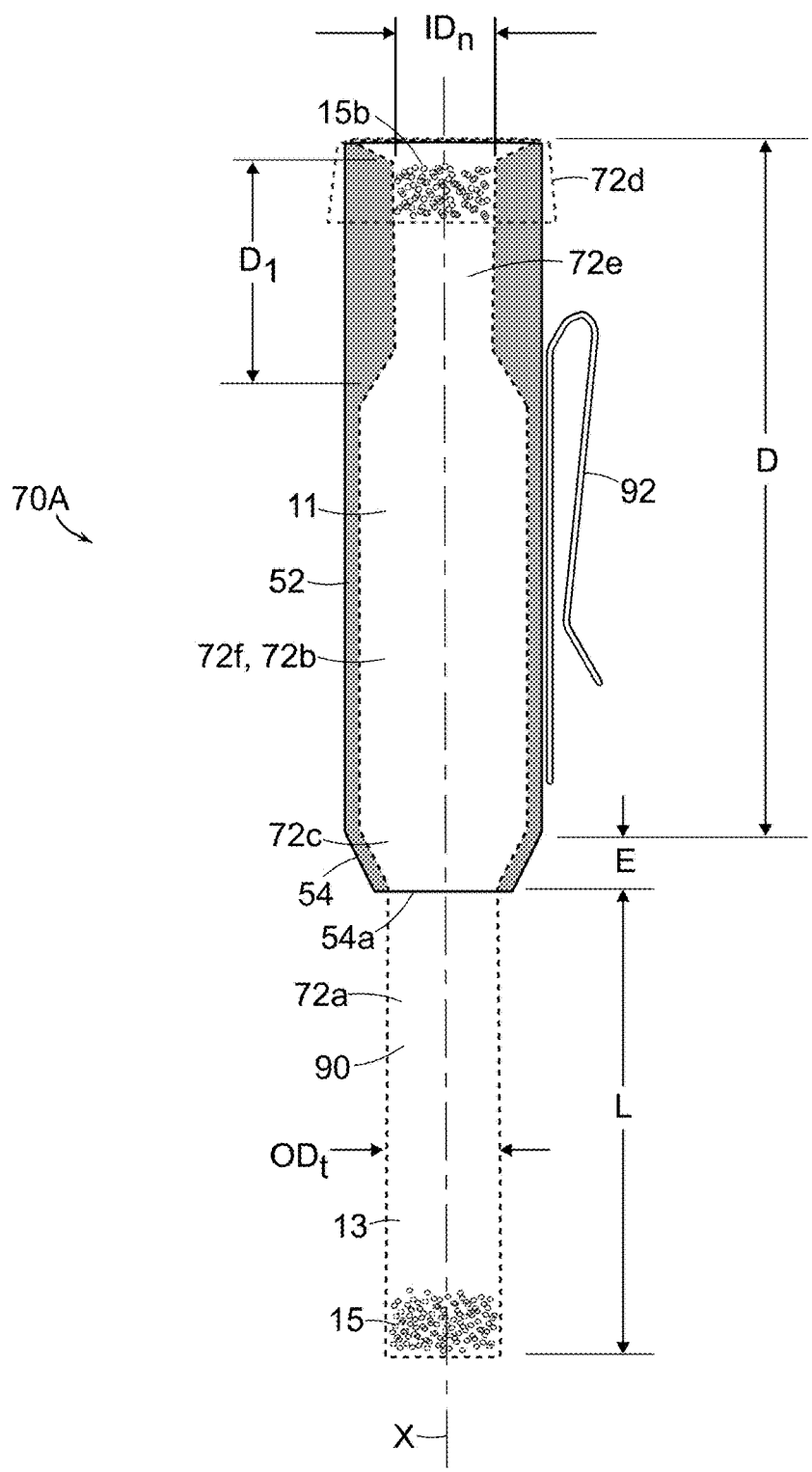
FIG. 32 is a front schematic view of another embodiment of a plankton separation device in the present invention.
Figure 33:
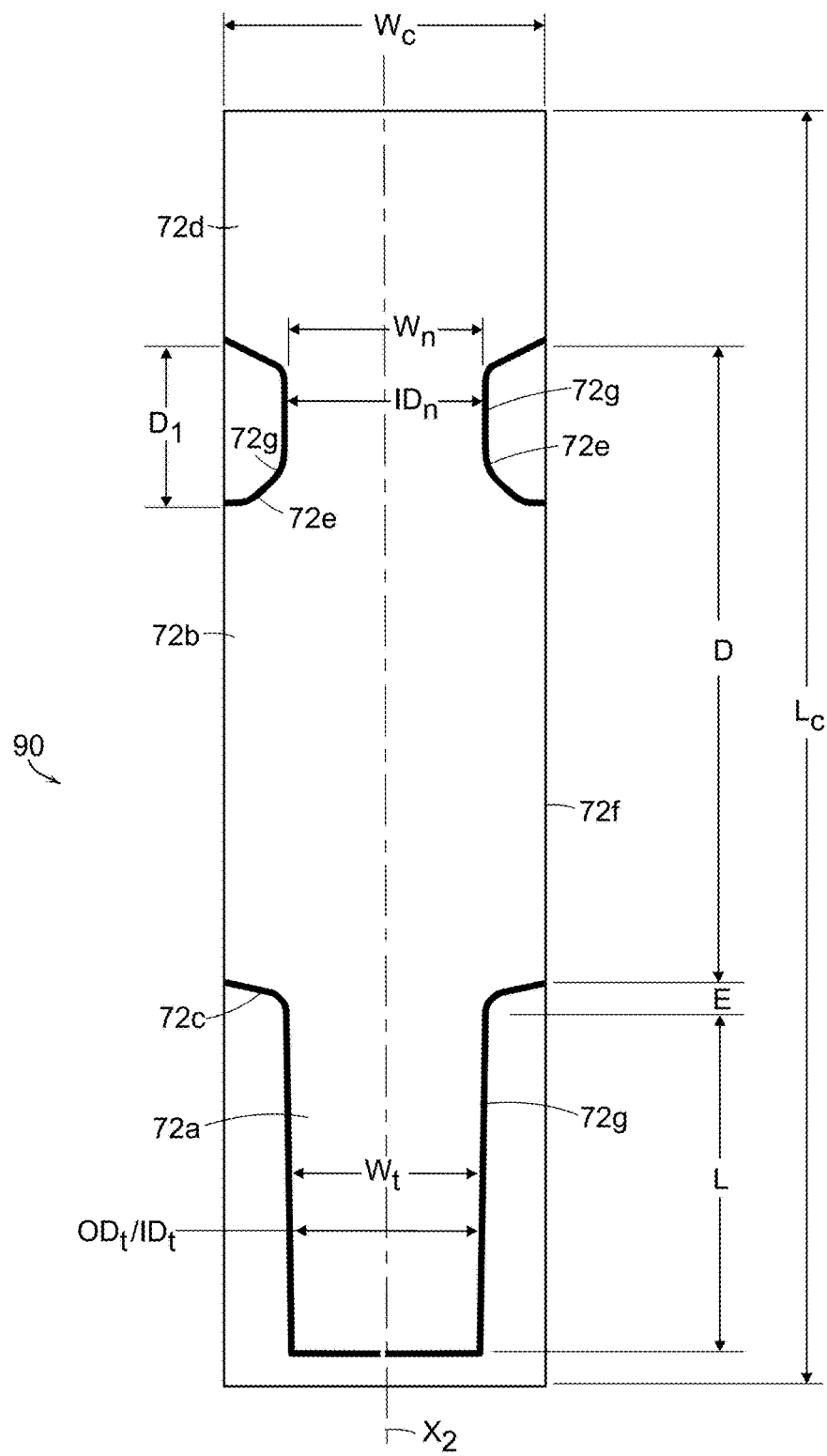
FIG. 33 is a front view of an embodiment of a transparent collection cartridge in the embodiment of FIG. 32.

Referring to FIG. 32, plankton separating or separation device 70A is another embodiment of a plankton separation device in the present invention. Separation device 70A differs from separation device 70 in that transparent collection chamber, region, container or cartridge 90 is used instead of cartridge 72. Transparent cartridge 90 can differ from cartridge 72 in that the upper body portion 72b can include a bottom larger diameter portion 72f that is fitted to the inner diameter of darkened chamber 52, a vertical or upright narrow elongate conduit, neck or column region, section or wall portion 72e can be above portion 72f at the top of darkened chamber 52 for concentrating and collimating floating phytoplankton such as Cyanobacteria 15b into a narrower vertical water column than the inner diameter of the darkened chamber 52, and a stop or lip 72d that can extend over the top of the darkened chamber 52 for attaching, securing or holding cartridge 90 in place within darkened chamber 52. Cap 58 can be secured over the stop or lip 72d to lock it in place. The narrowed neck 72e can have a length or height $D_1$ of about 20-30 mm (0.75-1.2 inches) an inner width or diameter $ID_n$ of about 16-18 mm (0.62 to 0.7 inches), which can form a narrowed conduit neck 72e that is coaxially positioned within the top of darkened chamber 52 and spaced apart from the walls thereof. This can concentrate floating Cyanobacteria 15b into a narrower and vertically longer column of water with more consistent concentration moving across the width diameter, so that it is easier for different people taking samples of Cyanobacteria 15b with suction or hydraulic pressure to more consistently remove samples with accurate and consistent concentration, minimizing human variation. Due to the narrow neck 72*e*, the volume of liquid held within the upper body portion 72*b* of cartridge 90 within darkened chamber 52 can be about 45 ml. The other dimensions of cartridge 90 can be similar to that described for cartridge 72. A clip 92 can be secured to the side darkened chamber 52 for use in securing in an upright position. Clip 92 can also be used for separation devices 50, 50A and 70. The cartridge 90 can be a molded polymer container, or can be a bag formed of polymer film.

FIG. 33 depicts an embodiment of transparent cartridge 90 that can be a clear polymer film bag. The cartridge 90 can be formed from a polymer film blank, tube or body extending along a central longitudinal axis $X_2$, with upper right and left heat seal lines 72*g* in the upper region of upper body portion 72*b* inwardly from the right and left sides of the polymer film tube to form the narrow neck 72*e*. The heat seal lines 72*g* can symmetrically extend inwardly from opposed outer edges, transition in a direction parallel to axis $X_2$ for about height $D_1$ and then extend outwardly back out to the opposed outer edges. The lip 72*d* can extend upwardly above narrowed neck 72*e* and can be folded over the top of the darkened chamber 52 as seen in FIG. 32. Lower right, bottom and left heat seal lines 72*g* in the lower transparent body portion 72*a* inwardly from the right, bottom and left outer edges of the polymer film tube can form the narrowed transparent collection container and the narrowing transition area 72*c*. When assembled within darkened chamber 52 as separation device 70A, the cartridge 90 can become circular, conforming to the circular boundaries of the darkened chamber 52, and can have the configuration and dimensions previously described. When the transparent cartridge 90 is formed of a polymer film and in a flattened state, in one embodiment, it can have a total cartridge length $L_c$ of about 203 mm (8 inches) and a flattened cartridge width $W_c$ of about 50 mm (2 inches). Heights D and E can match that of darkened chamber 52. The flattened width $W_t$ of transparent collection container 72*a* can be about 28 mm (1.1 inches) which can reduce to a diameter of about 20 mm±2 mm (about the same for both $OD_t$ and $ID_t$ due to thin-film thickness), when erected into circular shape during use. The length L of transparent collection container 72*a* can be about 55-70 mm long. The flattened width $W_n$ of narrowed neck 72*e* can be about 28 mm which can reduce to a neck diameter $ID_n$ of about 16-18 mm during use.

In embodiments of the present invention, a small volume plankton separating or separation device can have a total fluid capacity of about 55 to 75 mls. The darkened chamber 52 can have a volume capacity of about 45-50 mls, an inner diameter of about 25 to 30 mm, and a height D of about 100 to 110 mm. The darkened transitional adapter or area 54 can have an inner diameter narrowing down to about 20 mm±2 mm, such as about 19 mm (larger than 13 mm), a height E of about 3 or 5 to 30 mm, and a volume of about 1 to 10 mls. The transparent collection container can have an initial inner diameter of about 16 to 20 mm, a length L of about 44 mm-70 mm, and a volume of about 5 to 10 mls. The ratio of liquid volume of the darkened areas 52 and 54 to the transparent collection container 56 or 72 below area 54 can be about 7.4-8.5 to 1.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

For example, various features of the different embodiments can be combined together or omitted. In addition, although various directional terms have been used for components, this is not meant to limit the orientation for all situations.

What is claimed is:

1. A plankton separating device comprising:
a darkened chamber having an outer perimeter surrounding a central axis and a first inner width;
a darkened transitional area extending from the darkened chamber along the central axis having a second inner width that is smaller than the first inner width; and
a transparent collection container extending from the darkened transitional area along the central axis for allowing entrance of light therein, the transparent collection container of sufficient length to reinforce migration of plankton for separation, and extending beyond a point that makes about a 20°±2° angle to the central axis while extending to the nearest location of maximum outer perimeter dimension of the darkened chamber, the transparent collection container for collecting zooplankton so that samples of separated zooplankton and/or phytoplankton can be collected.

2. The device of claim 1 in which the darkened chamber has a port, the darkened transitional area being a darkened transitional adapter coupled to the port of the darkened chamber, the transparent collection container being a transparent collection tube coupled to the darkened transitional adapter and having a third inner width that is smaller than the second inner width.

3. The device of claim 2 in which the darkened chamber is generally cylindrical with about a 28 mm inner diameter, a height of about 109 mm, and a volume of about 50 mls, the darkened transitional adapter having about a 19 mm inner diameter, a height of about 30 mm, and a volume of about 9 mls, and the collection tube having an initial inner diameter of about 16 mm, and a volume of about 8 mls.

4. The device of claim 1 in which the transparent collection container is a transparent collection cartridge extending from the darkened transitional area.

5. The device in claim 4 in which the darkened chamber is generally cylindrical with about a 25 mm inner diameter, a height of about 100 mm, and a volume of about 50 mls, the darkened transitional area has about a 19 mm inner diameter, a height of about 5 mm, and a volume of about 1 ml, the transparent collection cartridge has an inner diameter extending from inside the inner diameter of the darkened transitional area, and a volume of about 6 mls.

6. The device of claim 4 in which the transparent collection cartridge is a disposable cartridge comprising a body extending along a central longitudinal axis comprising an upper body portion positioned in the darkened chamber, and a lower body portion extending from the upper body portion below the darkened chamber.

7. The device of claim 6 in which the transparent collection cartridge is formed of at least one of molded polymer and polymer film.

8. The device claim 7 in which the upper body portion includes a narrowed wall portion for concentrating floating Cyanobacteria into a narrow water column.

9. The device of claim 1 in which the darkened chamber is generally cylindrical with about a 25-30 mm inner diameter, and a height of about 100-110 mm, the darkened transitional area has about a 20 mm±2 mm inner diameter, and a height of about 3-30 mm, and the transparent collection container has an initial inner diameter about 16-20 mm and a length of about 44-70 mm.

* * * * *